(12) United States Patent
Uveges et al.

(10) Patent No.: US 12,343,446 B2
(45) Date of Patent: Jul. 1, 2025

(54) BONE REPAIR PRODUCT AND METHODS OF USE THEREOF

(71) Applicant: OSIRIS THERAPEUTICS, INC., Columbia, MD (US)

(72) Inventors: Thomas E. Uveges, Elkridge, MD (US); Jin-Qiang Kuang, Glenelg, MD (US); Alla Danilkovitch, Columbia, MD (US); S. Michael Sinclair, Ellicott City, MD (US); Sandra D. Geraghty, Elkridge, MD (US)

(73) Assignee: OSIRIS THERAPEUTICS, INC.

( * ) Notice: Subject to any disclaimer, the term of this patent is extended or adjusted under 35 U.S.C. 154(b) by 0 days.

(21) Appl. No.: 17/698,602

(22) Filed: Mar. 18, 2022

(65) Prior Publication Data

US 2022/0202991 A1 Jun. 30, 2022

Related U.S. Application Data

(60) Continuation of application No. 17/039,402, filed on Sep. 30, 2020, now abandoned, which is a continuation of application No. 15/298,142, filed on Oct. 19, 2016, now Pat. No. 10,828,395, which is a division of application No. 14/849,509, filed on Sep. 9, 2015, now Pat. No. 10,729,809.

(60) Provisional application No. 62/053,063, filed on Sep. 19, 2014.

(51) Int. Cl.
| | |
|---|---|
| *A61K 38/18* | (2006.01) |
| *A61L 27/36* | (2006.01) |
| *A61L 27/38* | (2006.01) |
| *A61L 27/40* | (2006.01) |
| *A61L 27/54* | (2006.01) |
| *A61P 19/08* | (2006.01) |

(52) U.S. Cl.
CPC .......... *A61L 27/3608* (2013.01); *A61K 38/18* (2013.01); *A61K 38/1825* (2013.01); *A61K 38/1841* (2013.01); *A61K 38/1866* (2013.01); *A61L 27/3604* (2013.01); *A61L 27/365* (2013.01); *A61L 27/3683* (2013.01); *A61L 27/3687* (2013.01); *A61L 27/3691* (2013.01); *A61L 27/3821* (2013.01); *A61L 27/3834* (2013.01); *A61L 27/3847* (2013.01); *A61L 27/40* (2013.01); *A61L 27/54* (2013.01); *A61P 19/08* (2018.01); *A61L 2300/414* (2013.01); *A61L 2300/64* (2013.01); *A61L 2430/02* (2013.01); *A61L 2430/40* (2013.01)

(58) Field of Classification Search
CPC . A61K 38/18; A61L 27/3608; A61L 27/3604; A61L 27/3821; A61L 27/3847
See application file for complete search history.

(56) References Cited

U.S. PATENT DOCUMENTS

| | | | |
|---|---|---|---|
| 5,641,518 A * | 6/1997 | Badylak | A61L 27/3683 424/551 |
| 5,827,740 A | 10/1998 | Pittenger | |
| 6,458,375 B1 | 10/2002 | Gertzman et al. | |
| 6,478,825 B1 | 11/2002 | Winterbottom et al. | |
| 6,835,377 B2 | 12/2004 | Goldberg et al. | |
| 8,435,566 B2 | 5/2013 | Behnam et al. | |
| 2003/0229400 A1 | 12/2003 | Masuda et al. | |
| 2004/0078090 A1 | 4/2004 | Binette et al. | |
| 2008/0262633 A1 * | 10/2008 | Williams | A61L 27/3687 623/23.63 |
| 2011/0008300 A1 * | 1/2011 | Wouters | A01N 1/0221 435/325 |
| 2011/0212064 A1 | 9/2011 | Jansen et al. | |
| 2011/0212065 A1 | 9/2011 | Jansen et al. | |
| 2014/0056857 A1 | 2/2014 | Williams et al. | |
| 2014/0212499 A1 * | 7/2014 | Cooper | A61L 27/365 424/489 |
| 2016/0082155 A1 | 3/2016 | Uveges et al. | |

FOREIGN PATENT DOCUMENTS

| | | |
|---|---|---|
| WO | WO 1998/032450 | 7/1998 |
| WO | WO 1998/051317 | 11/1998 |
| WO | WO 2002/000244 | 1/2002 |
| WO | WO 2002/036049 | 5/2002 |
| WO | WO 2007/133451 | 11/2007 |
| WO | WO 2014/011890 | 1/2014 |
| WO | WO 2016/044030 | 3/2016 |

OTHER PUBLICATIONS

"Safety Profile of Trinity® Evolution," [online] retrieved from<URL:orthofix.com/ftp/assets/Product/Product_Files/Trinity_Evolution/TE-0915_safetyPaper_NP.pdf, 8 pages.
Academy Medical: Bone Repair [online] retrieved from <URL: solutions.academymedical.net/?s=ovation [ retrieved on Dec. 10, 2015], 2 pages.
Albrektsson, T. and C. Johannsson, "Osteoinduction, osteoconduction, and osseointegration," European Spine Journal 10:S96-S101 (2001).
Allen et al., "Periosteum: biology, regulation, and response to osteoporosis therapies," Bone 35:1003-1012 (2004).
Allori et al., "Biological basis of bone formation, remodeling, and repair-part II: extracellular matrix," Tissue Eng Part B Rev 14(3):275-283 (2008).
Allori et al., "Biological basis of bone formation, remodeling, and repair-part I: biochemical signaling molecules," Tissue Eng Part B Rev 14(3):259-273 (2008).
ASTM Standard F2721, Standard Guide for Preclinical In Vivo Evaluation in Critical Size Segmental Bone Defects, ASTM International, West Conshohocken, Pa, USA, (2008), 13 pages.

(Continued)

*Primary Examiner* — Xiaozhen Xie
(74) *Attorney, Agent, or Firm* — Norton Rose Fulbright US LLC

(57) ABSTRACT

Provided herein is a bone repair composition that is composed of periosteum containing an angiogenic growth factor(s), cancellous bone chips containing viable osteogenic cells, and, optionally, demineralized bone matrix (DBM) chips. Also provided herein are articles of manufacture and methods of use thereof to treat bone defects.

25 Claims, No Drawings

(56) References Cited

OTHER PUBLICATIONS

Auerbach et al., "Angiogenesis assays: a critical overview," Clinical Chemistry 49( 1): 32-40 (2003).
Bagot et al., "Reconstructed human epidermis: absence of Langerhans cells and failure to stimulate allogeneic lymphocytes in vitro," Clin Exp Immunol 71(1): 138-143 (1988).
Baksh et al., "Adult mesenchymal stem cells: characterization, differentiation and application in cell and gene therapy," J Cell Mol Med 8:301-316 (2004).
Beamer et al., "Vascular endothelial growth factor: an essential component of angiogenesis and fracture healing," HSS J 6:85-94 (2010).
Blokhuis et al., "Resorbable calcium phosphate particles as a carrier material for bone marrow in an ovine segmental defect," Journal of Biomedical Materials Research 51:369-375 (2000).
Boskey, A. and P. Robey. The composition of bone. In: Rosen CJ, ed. Primer on the Metabolic Bone Diseases and Disorders of Mineral Metabolism, 8th ed. Scarborough, MA: Maine Medical Center Research Institute; 2013:49-58.
Bostrom et al., "Use of bone morphogenetic protein-2 in the rabbit ulnar nonunion model," Clinical Orthopedics & Related Research 327:272-282 (1996).
Brekke et al., "Principles of tissue engineering applied to programmable osteogenesis," Journal of Biomedical Materials Research 43:380-398 (1998).
Bruder et al., "The effect of implants loaded with autologous mesenchymal stem cells on the healing of canine segmental bone defects," Journal of Bone and Joint Surgery—American 80(7):985-996 (1998).
Buma et al., "Skeletal tissue engineering-from in vitro studies to large animal models," Biomaterials 25: 1487-1495 (2004).
Castro-Cesena et al., "Kinetics studies of bone demineralization at different HCl concentrations and temperatures," Materials Science and Engineering C31 :523-530 (2011).
Chen et al., "Osteogenic protein-1 induced bone formation in an infected segmental defect in the rat femur," Journal of Orthopaedic Research 20: 142-150 (2002).
Chen et al., "Strategies to enhance tendon graft-bone healing in anterior cruciate ligament reconstruction," Chang Gung Med J 32(5):483-492 (2009).
Cook et al., "Use of an osteoinductive biomaterial (rhOP-1) in healing large segmental bone defects," Journal of Orthopaedic Trauma 12:407-412 (1998).
Coultas et al., "Endothelial cells and VEGF in vascular development," Nature 438:937-945 (2005).
Dai et al., "Repairing of goat tibial bone defects with BMP-2 gene-modified tissue-engineered bone," Calcified Tissue International 77:55-61 (2005).
DePaula et al., "Effects of hydrogen peroxide cleaning procedures on bone graft osteoinductivity and mechanical properties," Cell and Tissue Banking 6:287-298 (2005).
Devescovi et al., "Growth Factors in Bone Repair," Chir Organi Mov 92(3): 161-168 (2008).
Dickinson et al., "Monoclonal anti-TNF-alpha suppresses graft vs host disease reactions in an in vitro human skin model," Cytokine 6(2): 141-146 (1994).
Duan-Arnold et al., "Angiogenic Potential of Cryopreserved Amniotic Membrane Is Enhanced Through Retention of All Tissue Components in Their Native State," Adv Wound Care 4(9): 513-522 (2015).
Duan-Arnold et al., "Retention of Endogenous Viable Cells Enhances the Anti-Inflammatory Activity of Cryopreserved Amnion," Adv Wound Care 4(9):523-533 (2015).
Duan-Arnold et al., "Soluble Factors Released by Endogenous Viable Cells Enhance the Antioxidant and Chemoattractive Activities of Cryopreserved Amniotic Membrane," Adv Wound Care 4(6):329-338 (2015).

Evans et al., "Elucidating multiscale periosteal mechanobiology: a key to unlocking the smart properties and regenerative capacity of the periosteum?" Tissue Engineering: Part B 19(2): 147-159 (2013).
Extended European Search Report issued in Corresponding Application No. 20155013.4, dated May 26, 2020.
Final Rejection was issued on Nov. 8, 2017 by the USPTO for U.S. Appl. No. 14/849,509, filed Sep. 9, 2015 and published as US 2016-0082155 A1 on Mar. 24, 2016 (Inventor—Thomas E. Uveges) (15 pages).
Gao et al., "Stabilization of an inserted tricalcium phosphate spacer enhances the healing of a segmental tibial defect in sheep," Arch Orthop Trauma Surg 116(5):290-294 (1997).
Geraghty et al., "A novel, cryopreserved, viable osteochondral allograft designed to augment marrow stimulation for articular cartilage repair," J Orthop Surg Res. 10: 66 (2015), 13 pages.
Grabowski et al., "Bone allograft with mesenchymal stem cells: A critical review of the literature," Hard Tissue 2(2) :20 (2013 ), 8 pages.
Gregory et al., "Non-hematopoietic bone marrow stem cells: molecular control of expansion and differentiation," Exp Cell Res 306:330-335 (2005).
Gruskin et al., "Demineralized bone matrix in bone repair: history and use," Advanced Drug Delivery Reviews 64: 1063-1077 (2012).
Gugala et al., "Regeneration of segmental diaphyseal defects in sheep tibiae using resorbable polymeric membranes: a preliminary study," Journal of orthopaedic Trauma 13:187-195 (1999).
International Preliminary Report on Patentability, issued Dec. 19, 2016, in connection with International Patent Application No. PCT/US2015/049248, 9 pages.
International Search Report and Written Opinion, issued Nov. 26, 2015, in connection with International Patent Application No. PCT/US2015/049248, 12 pages.
Ito et al., "Remodeling of cortical bone allografts mediated by adherent rAAV-RANKL and VEGF gene therapy," Nat Med 11:291-297 (2005).
Itoh et al., "Repair of ulnar segmental defect by recombinant human bone morphogenetic protein-2 in dogs," J Vet Med Sci 60:451-458 (1998).
IUPAC-IUB Commission on Bio-chemical Nomenclature Symbols for Amino-Acid Derivatives and Peptides, Biochemistry 11: 1726-1732 (1972).
Jahangir et al., "Bone-graft substitutes in orthopaedic surgery," Retrieved from URL:aaos.org/AAOSNow/2008/Jan/reimbursement/reimbursement2/?ssopc=1 [5 pages].
Kanczler, JM and O.O.C. Oreffo, "Osteogenesis and Angiogenesis: The potential for Engineering Bone," European Cells and Materials 15: 100-114 (2008).
Kigami et al., "Effect of basic fibroblast growth factor on angiogenesis and bone regeneration in non-critical-size bone defects in rat calvaria," J Oral Sci 56: 17-22 (2014).
Kim et al., "Characterization of Different Subpopulations from Bone Marrow-Derived Mesenchymal Stromal Cells by Alkaline Phosphatase Expression," Stem Cells and Development 21(16): 2958-2968 (2012).
Koretzky, GA, "Role of CD454 tyrosine phosphatase in signal transduction in the immune system," FASEB J 7: 420-426 (1993).
Laurencin et al., "Bone graft substitute materials," [online] [updated on Dec. 4, 2013] retrieved from <URL:emedicine.medscape.com/article/1230616-overview [retrieved on Aug. 21, 2014], 6 pages.
Lee et al., "Overproduction of recombinant human VEGF (vascular endothelial growth factor) in Chinese hamster ovary cells," J Microbiol Biotechnol 18(1): 183-187 (2008).
Letter/Written Disclosure of the Information Disclosure Statement for the above-referenced application, filed herewith on Jan. 10, 2017, 2 pages.
Lewandrowski et al., "An electron microscopic study on the process of acid demineralization of cortical bone," Cal Tiss Int 61:294-297 (1997).
Lewandrowski et al., "Improved osteoinduction of cortical bone allografts: a study of the effects of laser perforation and partial demineralization," J Orthop Res 15:748-756 (1997).

(56) References Cited

OTHER PUBLICATIONS

Lewandrowski et al., "Kinetics of cortical bone demineralization: controlled demineralization—a new method for modifying cortical bone allografts," J Biomed Mater Res 31:365-372 (1996).

Lieberman et al., "The effect of regional gene therapy with bone morphogenetic protein-2-producing bone-marrow cells on the repair of segmental femoral defects in rats," J Bone Joint Surg Am 81:905-917 (1999).

Lippross, S. and M. Alini, "Platelet-rich plasma for bone healing—to use or not to use," Published online at URL:aofoundation.org/Documents/platlet_plasma.pdf Retrived on Nov. 25, 2015, 5 pages.

Liu et al., "Experimental study of the osteogenic capacity of periosteal allografts: a preliminary report," Microsurgery 15:87-92 (1994).

Mara et al., "Periosteum as a source of mesenchymal stem cells: the effects of TGF-β3 on chondrogenesis" Clinics 2011, 66(3), 487-492.

Matrix Biosurgical Product Sheet for Grafix™ [online] retrieved from <URL:matrixbiosurgical.com/pages/products/cellular [retrieved on Dec. 10, 2015], 3 pages.

McBride et al., "Anisotropic mechanical properties of ovine femoral periosteum and the effects of cryopreservation," Journal of Biomechanics 44: 1954-1959 (2011).

Medtronic: Bone Grafting Options Categorization Guide [online] Retrieved from :<URL: infusebonegraft.com/wcm/groups/mdtcom_sg/@mdt/documents/documents/bone_graft_options_guide.pdf [retrieved on Dec. 10, 2015], 4 pages.

Moham, S. and C. Kesavan, "Role of insulin-like growth factor-1 in the regulation of skeletal growth," Curr Osteoporo Rep 10(2): 178-186 (2012).

Nandi et al., "Orthopaedic applications of bone graft & graft substitutes: a review," Indian Journal of Medical Research 132: 15-30(2010).

Neman et al., "Lineage mapping and characterization of the native proegnitor population in cellular allograft," Spine J 13(2): 162-174 (2013).

Non Final Rejection was issued on Jan. 26, 2017 by the USPTO for U.S. Appl. No. 14/849,509, filed Sep. 9, 2015 and published as US 2016/0082155 A1 on Mar. 24, 2016 (Inventor—Thomas E. Uveges) (8 pages).

Oakes et al., "An evaluation of human demineralized bone matrices in a rat femoral defect model," Clin Orthop Rel Res 413 :281-290 (2003).

Office Action issued on Apr. 13, 2018 by the Canadian Intellectual Property Office for Patent Application No. 2,961,715, which was filed on Mar. 17, 2017 (Inventor—Uveges et al.; Applicant—Osiris Therapeutics, Inc.; (4 pages).

Office Action was issued on Dec. 6, 2017 by the Canadian Patent Office for Canadian Application No. 2,961,715, which was filed on Sep. 9, 2015 and published as CA 2961715 on Mar. 24, 2016 (Applicant—Osiris Therapeutics, Inc.) (5 pages).

Ohashi et al., "Advanced glycation end products enhance monocyte activation during human mixed lymphocyte reaction," Clinical Immunology 134(31): 345-353 (2010).

Onishi et al., "Distinct and overlapping patterns of localization of bone morphogenic protein (BMP) family members and a BMP type II receptor during fracture healing in rats," Bone 22(6):605-612 (1988).

Ovation Multi potent Cellular Repair Suspension [online] retrieved from <URL:mimtb.com/images/Ovation_Sell_Sheets.pdf [retrieved on Dec. 10, 2015], 2 pages.

Petite et al., "Tissue-engineered bone regeneration," Nature Biotechnology 18: 959-963 (2000).

Pharmacopeia (USP) General Chapter <71>, "Sterility Testing" (United States Pharmacopeia General Chapter <71>, United States Pharmacopeial Convention: Rockville, MD, Dec. 2012, 35th revision), 6 pages.

Pietrzak et al., "BMP depletion occurs during prolonged acid demineralization of bone: characterization and implications for graft preparation," Cell Tissue Bank 12: 81-88 (2011).

Pittenger, M.F. and B.J. Martin, "Mesenchymal stem cells and their potential as cardiac therapeutics," Circ Res 95:9-20 (2004).

Pons et al., "VEGF improves survival of mesenchymal stem cells in infarcted hearts," Biochem Biophys Res Commun 376:419-422 (2008).

Reddi et al., "Biochemical sequences in the transformation of normal fibroblasts in adolescent rats," PNAS 69:1601-1605 (1972).

Response to Non Final Rejection was mailed on Jul. 31, 2017 to the USPTO for U.S. Appl. No. 14/849,509, filed Sep. 9, 2015 and published as US 2016/0082155 A1 on Mar. 24, 2016 (Inventor—Thomas E. Uveges) (8 pages).

Response to Restriction/Election was mailed on Oct. 10, 2016 to the USPTO for U.S. Appl. No. 14/849,509, filed Sep. 9, 2015 and published as US 2016/0082155 A1 on Mar. 24, 2016 (Inventor—Thomas E. Uveges) (5 pages).

Response, dated Jul. 19, 2016, to International Search Report and Written Opinion, issued Nov. 26, 2015, in connection with International Patent Application No. PCT/US2015/049248, 6 pages.

Response, mailed Nov. 18, 2016, to Written Opinion, issued Sep. 19, 2016, in connection with International Patent Application No. PCT/US2015/049248, 22 pages.

Restriction/Election was issued on Aug. 10, 2016 by the USPTO for U.S. Appl. No. 14/849,509, filed Sep. 9, 2015 and published as US 2016/0082155 A1 on Mar. 24, 2016 (Inventor—Thomas E. Uveges) (13 pages).

Rose ML, editor. The immune response to endothelial cells. Transplant-Associated Coronary Artery Vasculopathy, Chapter 3. Austin, TX: Landes Bioscience, Georgetown Texas USA; Eurekah.comp. 71-89 (2001).

Sakaguchi et al., "Comparison of human stem cells derived from various mesenchymal tissues," Arthritis and Rheumatism 52(8):2521-2529 (2005).

Sakaguchi et al., "Suspended cells from trabecular bone by collagenase digestion become virtually identical to mesenchymal stem cells obtained from marrow aspirates," Blood 104:2728-2735 (2004).

Sciadini, M.F. and K.D. Johnson, "Evaluation of recombinant human bone morphogenetic protein-2 as a bone-graft substitute in a canine segmental defect model," Journal of Orthopaedic Research 18:289-302 (2000).

Sekine et al., "Role of passenger leukocytes in allograft rejection: effect of depletion of donor alveolar macrophages on the local production of TNF-alpha, T helper I/T helper 2 cytokines, IgG subclasses, and pathology in a rat model of lung transplantation," J Immunol 159(8): 4084-4093 (1997).

Shen, H. and D .R. Goldstein, "IL-6 and TNF-alpha synergistically inhibit allograft acceptance," J Am Soc Nephrol 20(5): 1032-1040 (2009).

Smith et al., "Osseous regeneration in preclinical models using bioabsorbable delivery technology for recombinant human bone morphogenetic protein 2 (rhBMP-2)," Journal of Controlled Release 36: 183-195 (1995).

Spicer et al., "Evaluation of bone regeneration using the rat critical size calvarial defect," Nat Protoc 7:1918-1929 (2012).

Sruárez et al., "Alloimmunity to Human Endothelial Cells Derived from Cord Blood Progenitors," Journal of Immunology 179:7488-7496 (2007).

Staton et al., "A critical analysis of current in vitro and in vivo angiogenesis assays," Int J Exp Path 90: 195-221 (2009).

Staton et al., "Current methods for assaying angiogenesis in vitro and in vivo," Int J Exp Path 85:233-248 (2004).

Tadmori et al., "Suppression of the allogeneic response by human IL-10: a critical role for suppression of a synergy between IL-2 and TNF-alpha," Cytokine 6( 5) :462-4 71 (1994 ).

Taylor, M. J. and H.L. Bauk, "Function of Lymphocytes and Macrophages after Cryopreservation by Procedures for Pancreatic Islets: Potential for Reducing Tissue Immunogenicity," Cryobiology 25: 1-17 (1988).

Thitiset et al., "Development of collagent/demineralized bone powder scaffolds and periosteum-derived cells for bone tissue engineering application," Int J Mol Sci 14:2056-2071 (2013).

Toungouz et al., "Alloactivation Induced During Mixed-Lymphocyte Reaction Provokes Release of Tumor Necrosis Factor

(56) References Cited

OTHER PUBLICATIONS a and Interleukin 6 by Macrophages and Primer Them to Lipopolysaccharides," HumanImmunology 38: 221-225 (1993).

Trinity Evolution Brochure: Commercially available bone graft substitute options [online] retrieved on Jul. 16, 2014, 4 pages.

Trinity Evolution product description [online] retrieved from <URL:orthofix.com/products/trinity-evolution.asp [retrieved on Aug. 21, 2014], 2 pages.

Trinity Evolution Technical Brief: Allograft with viable cells: Redefining your bone grafting options through stem cell technology [online] retrieved on Oct. 21, 2014, 12 pages.

Tsuchida et al., "Engineered allogeneic mesenchymal stem cells repair femoral segmental defect in rats," Journal of Orthopaedic Research 21 :44-53 (2003).

Wang et al., "Interleukin-10 modulation of alloreactivity and graft-versushost reactions," Transplantation 74(6): 772-778 (2002).

Wheeler et al., "Radiomorphometry and biomechanical assessment of recombinant human bone morphogenetic protein 2 and polymer in rabbit radius ostectomy model," J Biomed Mater Res 43:365-373 (1998).

Wildemann et al., "Quantification of growth factors in allogenic bone grafts extracted with three different methods," Cell Tissue Bank 8: 107-114 (2007).

Willems, W. F. PhD Thesis Chapter 6 entitled "Induction of angiogenesis and osteogenesis in surgically revascularized frozen bone allografts by sustained delivery of FGF-2 and VEGF," Published Aug. 24, 2014 [online] Retrieved from: <URL:dare.uva.nl/document/2/139369, 14 pages.

Written Opinion, issued Sep. 19, 2016, in connection with International Patent Application No. PCT/US2015/049248, 7 pages.

Yasko et al., "The healing of segmental bone defects, induced by recombinant human bone morphogenetic protein (rhBMP-2). A radiographic, histological, and biomechanical study in rats," J Bone Joint Surg Am 74:659-670 (1992).

Yu et al., "Bone morphogenic protein 2 stimulates endochondral ossification by regulating periosteal cell fate during bone repair," Bone 47(1):65-73 (2010).

Zhang et al., "Periosteal Progenitor Cell Fate in Segmental Cortical Bone Graft Transplantations: Implications for Functional Tissue Engineering," J Bone Miner Res 20( 12) :2124-213 7 (2005).

Zuscik, M.J. "Skeletal Healing: In Primer on the Metabolic Bone Disease and Disorders of Minieral Metabolism," 8th Edition Editor: Rosen, CJ pp. 90-98 (2013 ).

\* cited by examiner

BONE REPAIR PRODUCT AND METHODS OF USE THEREOF

CROSS-REFERENCE TO RELATED APPLICATIONS

This application is a continuation of U.S. patent application Ser. No. 17/039,402 filed Sep. 30, 2020 (now abandoned), which is a continuation of U.S. patent application Ser. No. 15/298,142, filed Oct. 19, 2016 (now U.S. Pat. No. 10,828,395), which is a divisional of U.S. patent application Ser. No. 14/849,509, filed on Sep. 9, 2015 (now U.S. Pat. No. 10,729,809), which claims the benefit of priority to U.S. Provisional Pat. App. No. 62/053,063, filed Sep. 19, 2014. The contents of the referenced applications are incorporated into the present application by reference.

FIELD OF THE INVENTION

Provided herein is a bone repair composition that is composed of periosteum containing an angiogenic growth factor(s), cancellous bone chips and, optionally, demineralized bone matrix (DBM) chips. Also provided herein are articles of manufacture and methods of use thereof to treat bone defects.

BACKGROUND

Bone grafts, including autografts, allografts and other types of grafts, such as xenografts, synthetic and bioengineered grafts, have been used in a variety of procedures and treatments, including bone fusions such as spine fusions, disc augmentations in the spine, and bone fill applications employed in the treatment of disease, disorders or injuries including, but not limited to avascular osteonecrosis, osteosarcoma, acute fractures and non-unions, as well as for bone regeneration for orthopedic implants. Limitations exist with respect to treating subjects with existing bone graft options. For example, while autografts possess physiologic properties for bone healing, they require a second procedure to harvest bone that can result in donor site morbidity, limited supply of harvested bone and other limitations. Hence, there is a need for improved bone graft materials.

SUMMARY

Provided herein is a bone repair composition, also called a bone repair product (BRP) that is composed of: a) cancellous bone chips; and b) periosteum containing one or more biologically active angiogenic growth factor(s), whereby the composition mediates angiogenesis. In examples of the bone repair composition or BRP, the cancellous bone chips can contain viable osteogenic cells. Also provided herein is bone repair composition or BRP that is composed of: a) cancellous bone chips containing viable osteogenic cells; and b) periosteum containing one or more biologically active angiogenic growth factor(s), whereby the composition mediates angiogenesis. In the composition, the cancellous bone chips are from or from about 125 µm to 3 mm or 4 mm in size, such as from or from about 400 µm to 3 mm or 4 mm in size, for example, from or from about 600 µm to 2 mm in size.

In any of the examples of the bone repair composition, the composition can contain demineralized bone matrix (DBM) chips. The DBM can be demineralized cortical bone or can be demineralized cancellous bone. In any of such examples, the DBM chips are 4 mm or less than 4 mm in size, such as less than 600 µm in size, for example, from or from about 100 µm to 600 µm or 100 µm to 4 mm.

In any of the examples of the bone repair composition, the periosteum can be from long bone. In any of the examples of the bone repair composition, the cancellous bone chips, including cancellous bone chips containing viable osteogenic cells, can be from cancellous bone selected from among long bone, ileum, talus and calcaneus. In the above examples, the long bone can be the femur, tibia, fibula or humerus.

In any of the examples of the bone repair composition, the periosteum component is made up of periosteum pieces that are sticky, and the periosteum pieces self-adhere and adhere to the bone chips, thereby forming the composition. The periosteum is prepared to produce periosteum pieces by processing in the presence of a physiologic solution, whereby the periosteum retains a biologically active angiogenic growth factor(s). In any of the examples, the periosteum is present from or from about 1% to 50%, 2% to 40%, 3% to 30%, 4% to 25% or 5% to 20% by weight (mass/mass) of the composition.

In any of the examples of the bone repair composition containing DBM chips, the DBM is present at no more than 45% by weight (mass/mass) of the cancellous bone chips comprising osteogenic cells. For example, the DBM is present from or from about 1% to 45% by weight of the cancellous bone chips, such as from or from about 25% to 45% by weight of the cancellous bone chips.

In any of the examples of the bone repair composition, the biologically active angiogenic growth factor(s) present in the periosteum component can be one or more of vascular endothelial growth factor (VEGF), platelet derived growth factor (PDGF), basic fibroblast growth factor (bFGF) or insulin-like growth factor-I (IGF-I). In any of the examples of the bone repair composition provided herein, the composition exhibits angiogenic activity that is at least 0.5-fold, 1-fold, 2-fold, 3-fold, 4-fold, 5-fold, 6-fold, 7-fold, 8-fold, 9-fold, 10-fold, 15-fold, 20-fold, 30-fold, 40-fold, 50-fold, 60-fold, 70-fold, 80-fold, 90-fold, 100-fold or more greater than the angiogenic activity of a corresponding bone graft not containing periosteum or containing periosteum prepared or processed in the presence of a protein denaturing condition. In any of the examples of the bone repair composition provided herein, the specific activity of the composition for mediating angiogenesis can be at least 0.5-fold, 1-fold, 2-fold, 3-fold, 4-fold, 5-fold, 6-fold, 7-fold, 8-fold, 9-fold, 10-fold, 15-fold, 20-fold, 30-fold, 40-fold, 50-fold, 60-fold, 70-fold, 80-fold, 90-fold, 100-fold or more greater than the specific activity of a corresponding bone graft containing periosteum prepared or processed in the presence of a protein denaturing condition.

In any of the examples of a bone repair composition provided herein, the composition contains at least 0.5-fold, 1-fold, 1.5-fold, 2-fold, 2.5-fold, 3-fold, 3.5-fold, 4-fold, 4.5-fold, 5-fold, 6-fold, 7-fold, 8-fold, 9-fold, 10-fold or greater concentration of an angiogenic growth factor(s) than the concentration of the same angiogenic growth factor(s) in a corresponding bone graft not containing periosteum or containing periosteum prepared or processed in the presence of a protein denaturing condition. For example, the composition can contain one or more angiogenic growth factors that is a VEGF, bFGF, PDGF or IGF-1, and the concentration of each angiogenic growth factor in the composition can independently be at least 1 pg/mL, 5 pg/mL, 10 pg/mL, 20 pg/mL, 30 pg/mL, 40 pg/mL, 50 pg/mL, 60 pg/mL, 70 pg/mL, 80 pg/mL, 90 pg/mL, 100 pg/mL, 150 pg/mL, 200 pg/mL, 250 pg/mL, 300 pg/mL, 350 pg/mL, 400 pg/mL, 450 pg/mL, 500 pg/mL, 1000 pg/mL, 2000 pg/mL, 3000 pg/mL, 4000 pg/mL, 5000 pg/mL, 10000 pg/mL, 20000 pg/mL, 30000 pg/mL, 40000 pg/mL, 50000 pg/mL or more of the composition. For example, the concentration of each angiogenic growth factor can independently be from or from about 1 pg/mL to 50000 pg/mL, 1 pg/mL to 10000 pg/mL, 1 pg/mL to 5000 pg/mL, 1 pg/mL to 1000 pg/mL, 5 pg/mL to 50000 pg/mL, 5 pg/mL to 10000 pg/mL, 5 pg/mL to 5000 pg/mL, 5 pg/mL to 1000 pg/mL, 10 pg/mL to 50000 pg/mL, 10 pg/mL to 10000 pg/mL, 10 pg/mL to 5000 pg/mL, 10 pg/mL to 1000 pg/mL, 100 pg/mL to 50000 pg/mL, 100 pg/mL to 10000 pg/mL, 100 pg/mL to 5000 pg/mL, 100 pg/mL to 1000 pg/mL, 100 pg/mL to 800 pg/mL, 100 pg/mL to 600 pg/mL, 100 pg/mL to 400 pg/mL, 100 pg/mL to 200 pg/mL, 200 pg/mL to 1000 pg/mL, 200 pg/mL to 800 pg/mL, 200 pg to 600 pg/mL, 200 pg/mL to 400 pg/mL, 400 pg/mL to 1000 pg/mL, 400 pg/mL to 800 pg/mL, 400 pg/mL to 600 pg/mL, 600 pg/mL to 1000 pg/mL, 600 pg/mL to 800 pg/mL or 800 pg/mL to 1000 pg/mL of the composition.

In any of the examples of the bone repair composition provided herein, in addition to the angiogenic activity, the composition exhibits one or more further activity that is an osteoconductive, osteoinductive or osteogenic activity. For example, the compositions exhibit angiogenic, osteoinductive and osteoconductive activity. In another example, the composition exhibits angiogenic, osteoinductive, osteoconductive and osteogenic activity.

In any of the examples of the bone repair composition provided herein composed of cancellous bone containing viable osteogenic cells, the osteogenic cells can be mesenchymal stem cells, osteoprogenitor cells, osteoblasts, or osteocytes. For example, the osteogenic cells can be mesenchymal stem cells that are $CD105^+$ and/or CD166+. In other examples, the osteogenic cells can be osteoprogenitor cells that are tissue non-specific alkaline phosphatase positive ($TNAP^+$).

In any of the examples of the bone repair composition provided herein composed of cancellous bone containing viable osteogenic cells, the composition contains at least one viable cell. For example, cell viability in the composition is greater than or equal to 1%, 5%, 10%, 20%, 30%, 40%, 50%, 60%, 70%, 80%, 90%, 95% or more, such as generally greater than or equal to 70%, 75%, 80%, 85%, 86%, 87%, 88%, 89%, 90%, 91%, 92%, 93%, 94%, 95%, 96%, 97%, 98%, 99% or more. In any of the bone repair compositions provided herein, the composition can contain at least $1\times10^3$ cells/cc, $1\times10^4$ cells/cc, $1\times10^5$ cells/cc, at least $2\times10^5$ cells/cc, $3\times10^5$ cells/cc, $4\times10^5$ cells/cc, $5\times10^5$ cells/cc, $6\times10^5$ cells/cc, $7\times10^5$ cells/cc, $8\times10^5$ cells/cc, $9\times10^5$ cells/cc, $1\times10^6$ cells/cc, $1.5\times10^6$ cells/cc, $2\times10^6$ cells/cc, $3\times10^6$ cells/cc, $4\times10^6$ cells/cc, $5\times10^6$ cells/cc, $6\times10^6$ cells/cc, $7\times10^6$ cells/cc, $8\times10^6$ cells/cc, $9\times10^6$ cells/cc, $1\times10^7$ cells/cc or more. For example, the composition can contain from or from about $1\times10^3$ cells/cc to $1\times10^7$ cells/cc, $1\times10^4$ cells/cc to $1\times10^7$ cells/cc, $1\times10^5$ cells/cc to $1\times10^7$ cells/cc, $2\times10^5$ cells/cc to $8\times10^6$ cells/cc, $5\times10^5$ cells/cc to $6\times10^6$ cells/cc or $7\times10^5$ cells/cc to $5\times10^6$ cells/cc.

In any of the examples of the bone repair composition provided herein, the periosteum can be devitalized. In any of the examples of the bone repair composition provided herein, the composition can be essentially free of blood cells, such as endothelial cells and/or hematopoietic cells. For example, the composition is substantially free of $CD31^+$ and $CD45^+$ cells.

In any of the examples of the bone repair compositions provided herein, the volume of the composition is 0.2 cc to 100 cc, for example, at least 0.2 cc, 0.3 cc, 0.4 cc, 0.5 cc, 0.6 cc, 0.7 cc, 0.8 cc, 0.9 cc, 1 cc, 1.5 cc, 2 cc, 2.5 cc, 3 cc, 3.5 cc, 4 cc, 4.5 cc, 5 cc, 6 cc, 7 cc, 8 cc, 9 cc, 10 cc, 20 cc, 30 cc, 40 cc or 50 cc. In any of the examples of the bone repair composition provided herein, the composition can be cryopreserved.

Also provided herein is a package or container or other article of manufacture that contains any of the above bone repair compositions or BRPs. The container can be straight sided jar. The container can be a tray.

Also provided herein is a method of repairing a bone defect in a subject by administering to the site of the defect any of the above bone repair compositions or BRPs. For example, the composition can be administered by filling a bony void at the site of the defect. In any of such examples, the bone defect can be one that results from a developmental failure, degeneration or trauma. The method of repairing a bone defect can be associated with a procedure that includes induction of bone formation for hip replacement operations, knee replacement operations, foot and ankle surgeries, spinal fusion procedures, repair of periodontal defects, treatment of osteoporosis, repair of bone tumor defects, dental procedures, repair of cranial maxilla facial defects or repair of bone fractures or defects. In any of the above methods, the defect can be a simple fracture, compound fracture, external fixation, internal fixation, joint reconstruction, arthroplasty, degenerative disc disease, avascular osteonecrosis, osteosarcoma fracture, fracture non-unions, spinal fusion, disc augmentation, or bone regeneration in orthopedic implants.

Also provided herein is a method of preparing a bone repair compositions, such as any of the bone repair compositions provided above and herein. For example, provided herein is a method of preparing a bone repair composition, by combining isolated periosteum containing one or more biologically active angiogenic growth factor(s) and isolated cancellous bone chips, wherein the periosteum is made up of pieces that are sticky, such that the periosteum pieces self-adhere and adhere to the bone chips, thereby preparing the bone repair composition. In such an example of the method, the cancellous bone chips can be isolated or prepared to contain viable osteogenic cells. In any of the above methods, the composition that is prepared further contains demineralized bone matrix (DBM) chips, and the method includes combining the periosteum, cancellous bone chips, and DBM. In such an example, the periosteum is made up of pieces that are sticky, such that the periosteum pieces self-adhere and adhere the bone chips, thereby preparing the bone repair composition.

Also provided herein is a method of preparing a bone repair composition that includes: a) processing periosteum to produce periosteum pieces that are sticky, wherein the periosteum contains one or more biologically active angiogenic growth factor(s); b) processing cancellous bone to produce cancellous bone chips; and c) combining periosteum and cancellous bone chips, wherein the periosteum is processed to be made up of pieces that are sticky such that the periosteum pieces adhere to themselves and the bone chips, thereby preparing the bone repair composition. In such a method, the cancellous bone chips can be processed to contain viable osteogenic cells. Also, in such a method, processing periosteum to produce periosteum pieces that are sticky can be achieved by mincing or cutting isolated periosteum. In the above examples of the method, prior to step c), the method can include preparing demineralized bone matrix (DBM) chips; and in step c), combining periosteum, cancellous bone chips, and DBM, wherein the periosteum is processed to be made up of pieces that are sticky, such that the periosteum pieces adhere to themselves and the bone chips, thereby preparing the bone repair composition.

In any of the above methods of preparing a bone repair composition, the cancellous bone chips are processed from cancellous bone using a method selected from among blending, milling, grating, and grinding to produce the bone chips. For example, the cancellous bone chips are processed from cancellous bone by blending to produce the bone chips. In any of such examples, the method can include selecting cancellous bone chips that are from or from about 125 µm to 3 mm in size, for example, 400 µm to 3 mm in size, such as from or from about 600 µm to 2 mm in size, wherein the selected bone chips are combined in the method.

In any of the above methods of preparing a bone repair composition provided herein, DBM is prepared by acid extraction of bone chips. The DBM bone chips can be produced from cancellous bone or from cortical bone. The DBM bone chips can be produced using a method selected from among blending, milling, grating, or grinding. In any of such examples, the method can include selecting bone chips that are less than 4 mm in size, such as less than 600 µm in size, for example, from or from about 100 µm to 600 µm in size. The DBM can be prepared from the selected bone chips 4 mm or less than 4 mm in size, such as less than 600 µm in size or from about 100 µm to 600 µm in size or 100 µm to 4 mm. For example, DBM can be prepared using acid extraction by incubation of bone chips with an acid that is hydrochloric acid or citric acid. The concentration of acid can be 0.1 N to 3 N or 0.1 N to 1 N.

In any of the above methods of preparing a bone repair composition provided herein, in step a), processing is performed in the presence of a physiologic solution. For example, the physiologic solution can be physiologic saline or phosphate buffered saline (PBS). Hence, in practice of any of the methods provided herein, the processed periosteum contains biologically active angiogenic growth factor(s), whereby the bone repair composition mediates angiogenesis. For example, the angiogenic growth factor(s) can be one or more of vascular endothelial growth factor (VEGF), platelet derived growth factor (PDGF), basic fibroblast growth factor (bFGF) or insulin-like growth factor-I (IGF-I).

In any of the above methods of preparing a bone repair composition, the cancellous bone chips can be processed or derived from cancellous bone selected from among ileum, long bone, talus or calcaneus. In any of the above methods, the periosteum can be derived or processed from long bone. In such examples, the long bone can be the tibia, fibula, femur or humerus. In any of the above methods of preparing a bone repair composition, all combined components can be processed from the same donor.

In any of the above methods of preparing a bone repair composition, the method can include treating the bone repair composition with a solution containing an antibiotic(s), antimyotic(s) or a combination thereof. In any of the above methods, the method can include storing the composition at a temperature of from or from about 0° C. to 30° C., for example, 2° C. to 25° C., such as from or from about 2° C. to 8° C. or 18° C. to 25° C., each inclusive. In other examples of any of the above methods of preparing a bone repair composition, the method can include performing a cryopreservation process, wherein the method includes storing the composition at a temperature of −20° C. to −196° C. In examples of such methods, the viability of osteogenic cells is retained. For example, the method can include storing the composition, such as in the presence of a cryopreservation solution, at about or up to −80° C.±5° prior to use. In such examples, the method can include thawing the prepared bone repair composition under conditions to retain its handling properties. This can be performed prior to use of the composition in a method to repair a bone defect. In such an example, cell viability of osteogenic cells is retained post-thaw.

Also provided herein is a bone repair composition that is produced by any of the above methods.

DETAILED DESCRIPTION

Outline
  A. Definitions
  B. Bone Grafts and Mechanisms of Bone Repair and Healing
    1. Bone Repair and Regeneration
    2. Properties of Bone Graft Supporting Bone Repair
      a. Osteoconduction
      b. Osteoinduction
      c. Osteogenesis
      d. Angiogenesis
    3. Bone Grafts and Bone-Graft Substitutes
  C. Bone Repair Product Compositions and Formulations
    1. Components of Bone Repair Product (BRP)
      a. Periosteum
      b. Cancellous Bone Matrix
      c. Demineralized Bone
    2. Packaging and Articles of Manufacture
  D. Method of Preparing Bone Repair Product Composition
    1. Processing and Preparing Bone Components
      a. Processing Periosteum
      b. Processing Cancellous Bone Containing Osteogenic Cells
      c. Processing Demineralized Bone (DBM)
    2. Combining Components to Produce Bone Repair Product (BRP)
    3. Sterilization and Preservation of Bone Repair Product (BRP)
  E. Method of Assessing Properties and Activities of Bone Repair Product (BRP)
  F. Method of Use of Bone Repair Product (BRP)
  G. Examples A. Definitions Unless defined otherwise, all technical and scientific terms used herein have the same meaning as is commonly understood by one of skill in the art to which the invention(s) belong. All patents, patent applications, published applications and publications, GenBank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

As used herein, "bone repair composition" or "bone repair product" or "BRP," which are used interchangeably, refer to a bone repair composition that is composed of periosteum, cancellous bone chips and, optionally, demineralized bone matrix (DBM) chips. The periosteum provides angiogenic and osteoinductive growth factors and other proteins, and hence ensures that BRP exhibits angiogenic properties. For inclusion in BRP, the components of BRP, including periosteum, are produced or prepared in the presence of physiologic solution in order to retain biologically active growth factors and other proteins. For example, for inclusion in BRP, the periosteum component is prepared by processing periosteum into pieces in the presence of a physiologic solution (e.g. physiologic saline), whereby the periosteum retains biologically active angiogenic growth factor(s) and other proteins. Also, in the composition, the periosteum pieces are sticky and adhere to themselves and to the bone chips to produce a uniform composition that exhibits handling properties so that the product is malleable, shapeable and packable. In addition to angiogenic properties, the presence of growth factors and other proteins and extracellular matrix (ECM) present in the bone chips (cancellous and/or DBM) means that BRP also can exhibit osteoconductive and osteoinductive properties. Further, cancellous bone chips can contain viable osteogenic cells. Hence, BRP provided herein can exhibit osteoconduction, osteoinductive, osteogenic and angiogenic properties. In some examples, BRP is an allograft derived from human donor tissue.

As used herein, "physiologic solution" refers to a solution that contains a salt composition and osmotic pressure similar to blood plasma. Hence, it is isotonic with normal body fluids. For example, a physiologic solution is a solution that can contain about or approximately 0.90% w/v of sodium chloride and a tonicity of from about or approximately 250 mOsm/L to 375 mOsm/L. Exemplary of physiologic solutions include, but are not limited to, physiologic saline, phosphate buffered saline (PBS), Ringer's solution, and Lactated Ringer's solution.

As used herein, "handling properties" refers to the capability of BRP to be manipulated for packaging, application or for any other suitable manner. The handling properties are achieved because the composition of the bone repair product ensures that the bone fragments and periosteum are adhered together so that bones are not separated or lost. This means that BRP retains its ability to mold into different shapes, such that it is shapeable and malleable. Generally, for purposes of the product provided herein, the handling properties are provided by the periosteum component of the product, which is sticky so that periosteum pieces self-adhere and adhere to the bone chips. The handling properties also can be provided by incorporation of another biocompatible component that exhibits adhesive or sticky properties, such as any described herein or known in the art.

As used herein, "periosteum" or "periosteal tissue" refers to the membrane of tissue that lines the outer surface of bones.

As used herein, "cancellous bone" refers to the meshwork of spongy tissue (trabeculae) of mature bone typically found at the core of vertebral bones in the spine and the epiphysis of the long bones.

As used herein, "cancellous bone containing viable osteogenic cells" refers to cancellous bone that contains osteogenic cells embedded in the bone where there is at least one viable cell. For example, cell viability can range from or from about 1% to 100%, such as greater than or equal to 1%, 5%, 10%, 20%, 30%, 40%, 50%, 60%, 70%, 80%, 90% or more of the cells are viable. In particular examples, 70% or greater of the cells are viable, such as greater than or equal to 75%, 80%, 85%, 86%, 87%, 88%, 89%, 90%, 91%, 92%, 93%, 94%, 95%, 96%, 97%, 98%, 99% or more of the cells are viable. The presence of osteogenic cells and viable cells contained in cancellous bone can be determined by procedures known in the art, such as any described herein. For example, cells can be isolated from bone, such as by enzymatic treatment (e.g. collagenase treatment). Cells can be assessed for known markers of osteogenic cells, including but not limited to, CD105, CD166 or TNAP. Cells also can be assessed for viability using various procedures in the art, such as trypan blue staining. Viability also can be assessed on the bone fragments using a LIVE/DEAD Viability/Cytotoxicity Kit by measuring changes in fluorescence of cells in bone upon staining with the acetomethoxy derivative of calcein known as calcein-AM (live) or ethidium bromide (dead).

As used herein, "cortical bone" (also called compact bone) refers to the dense outer surface of bone that forms a protective layer around the internal cavity.

As used herein, "demineralized" refers to any material generated by removing mineral material from tissue, such as bone tissue. Typically, a material is demineralized if it exhibits less than 8% calcium, such as less than 7%, 6%, 5%, 4%, 3%, 2%, 1% or less calcium. Demineralization can be achieved by methods known in the art, such as by using acids, chelating agents or electrolysis. For example, acid extraction methods can be employed, for example, using hydrochloric acid, citric acid or other suitable acids.

As used herein, "demineralized bone matrix" or "DBM" refers to any bone material that has been demineralized to remove mineral material from bone tissue. Typically, DBM is a bone tissue preparation that exhibits less than 8% calcium, such as less than 7%, 6%, 5%, 4%, 3%, 2%, 1% or less calcium.

As used herein, "long bone" refers to hard, dense bones that provide strength, structure, and mobility. A long bone has a shaft and two ends. Long bones typically are longer than they are wide. Examples of long bones include the femur, fibula, humerus, and tibia.

As used herein, "bone particle" or "bone fragment" or "bone chip" refers to a piece of particulated bone ranging in size, in any direction, from about 100 µm to 10 mm, and generally from 100 µm to 5 mm. Various size bone fragments as described herein can be employed in the product. The bone fragments can be any suitable shape or configuration, such as round, elongated or can have an irregular shape or other suitable shape or configuration.

As used herein, a "bone graft" refers to an implanted material that promotes bone healing alone or in combination with other materials, through osteogenesis, osteoinduction, osteoconduction, and also angiogenesis in combination or alone.

As used herein, "allograft" refers to a tissue graft from a donor of the same species as the recipient but not genetically identical.

As used herein, "osteogenic cells" refers to cells that support bone growth or are capable of differentiating into cells supporting bone growth. Such cells include mesenchymal stem cells (MSCs) capable of differentiating into bone cells, osteoprogenitor cells (OPCs), osteoblasts and osteocytes.

As used herein, "osteoprogenitor cells" refer to relatively undifferentiated cells found on or near all of the free surfaces of bone, which, under certain circumstances, undergo division and transform into osteoblasts or coalesce to give rise to osteocytes. Osteoprogenitor cells are positive for tissue-nonspecific alkaline phosphatase (TNAP).

As used herein, "mesenchymal stem cell (MSC)" refers to multipotent stromal cells that can differentiate into a variety of cells types, including osteoblasts (bone cells), chondrocytes (cartilage cells), and adipocytes (fat cells). MSCs can be distinguished by cell surface markers, including but not limited to, CD166 (ALCAM, SB10), CD90 (Thy-1), CD44 (hyaluronan receptor), CD105 (SH2), CD147 (neuroregulin), Stro-1, CD54 (intercellular adhesion molecule 1), or combinations thereof.

As used herein, "osteoblast" refers to cells that are derived from osteoprogenitor cells and are responsible for the synthesis of the organic components of bone matrix, i.e. osteoid. Osteoblasts are positive for tissue-nonspecific alkaline phosphatase (TNAP). Osteoblasts also are positive for osteocalcin, which is a marker for osteoblast lineage cells.

As used herein, "osteocytes" refer to a mature osteoblast that is generated when an osteoblast has completely surrounded itself and its cytoplasmic processes with matrix.

As used herein, "osteoconductive" or "mediates osteoconduction" refers to a scaffold property of a bone graft allowing for the ingrowth of neovasculature and the migration of osteoprogenitors into the graft site.

As used herein, "osteoinductive" or "mediates osteoinduction" refers to the ability of bone graft material to induce cell migration, proliferation, and/or differentiation of stem cells, osteoprogenitor cells, osteoblasts or osteocytes into mature bone cells. This process is mediated by bone growth factors or osteoinductive growth factors within the graft material.

As used herein, "bone growth factor" or "osteoinductive growth factor" refers to a growth factor or other proteins that supports osteoinduction. Examples of such growth factors include, but are not limited to, bone morphogenic proteins (e.g. BMP-2, -4, -6, -7 or -9), basic fibroblast growth factor (bFGF), insulin-like growth factor-I and -II (IGF-I and IGF-II), platelet derived growth factor (PDGF) and transforming growth factor-betas (TGF-βs).

As used herein, "osteogenic" or "mediates osteogenesis" refers to the ability of a bone graft to produce new bone, which is a process that is dependent on the presence of live osteogenic bone cells in the graft. Hence, it is a property of bone grafts that contain osteogenic cells.

As used herein, "angiogenic" or "mediates angiogenesis" refers to the ability of the graft to induce migration, proliferation and/or differentiation of endothelial cells leading to new blood vessel formation. This process is mediated by angiogenic growth factors and other proteins within the graft material. As is known by a skilled artisan, the presence of angiogenic factors alone may not promote blood vessel formation; rather, a mixture or cocktail of such factors along with an appropriate scaffold can be required to mediate angiogenesis. A graft, such as the bone repair composition provided herein, mediates angiogenesis if it contains angiogenic growth factors and induces migration, proliferation and/or differentiation of endothelial cells or induces blood vessel formation. In particular, a graft, such as the bone repair composition provided herein, mediates angiogenesis if it contains growth factors and induces blood vessel formation. Migration, proliferation, differentiation and/or blood vessel formation can be assessed by in vivo, ex vivo or in vitro assays known to a skilled artisan (see e.g. Staton et al. (2009) *Int. J. Exp. Path.*, 90:195-221; Staton et al. (2004) *Int. J. Exp. Path.*, 85:233-248; Auerbach et al. (2003) *Clinical Chemistry*, 49:32-40). Such assays can be performed with endothelial cells, such as human umbilical vein endothelial cells (HUVEC). In one example, proliferation of HUVECs can be assessed by monitoring cell number directly or indirectly, such as by measuring DNA synthesis by measuring the incorporation of [3H]thymidine into cells. In another example, blood vessel formation can be assessed in an in vitro endothelial tube formation assay using HUVECs such as described in the Examples herein. For example, as demonstrated herein BRP that contains periosteum mediates angiogenesis, whereas the corresponding product not containing periosteum does not mediate angiogenesis (see, Example 11).

As used herein, an "angiogenic growth factor" refers to a growth factor and other proteins that participate in processes that mediate angiogenesis. Examples of such growth factors include, but are not limited to, vascular endothelial growth factor (VEGF), platelet derived growth factor (PDGF), basic fibroblast growth factor (bFGF) and insulin-like growth factor-I (IGF-I).

As used herein, "biologically active" with reference to angiogenic growth factor(s) contained in the periosteum refers the presence of one or more active angiogenic growth factors in the periosteum that is/are capable of mediating angiogenesis of BRP. Whether periosteum or BRP containing periosteum contains a biologically active growth factor(s) need not require determination of the exact growth factors or amount of growth factors, but can be evaluated by assessing the biological activity of protein extracts of BRP to mediate angiogenesis. The presence of biologically active growth factor(s) in the periosteum can be determined by preparation of protein extracts of a composition containing periosteum, and assessing the protein extract for angiogenic activity using any of the assays described above or known in the art. For example, angiogenic activity can be assessed using an endothelial tube formation assay or a HUVEC proliferation assay. In one example, periosteum can be processed as described herein, protein extracts prepared, and the protein extract from the periosteum assessed for angiogenic activity. In another example, BRP containing periosteum can be prepared as described herein, protein extracts prepared, the protein extract from BRP assessed for angiogenic activity, and activity compared to a corresponding bone graft that contains the same components but does not contain periosteum. In such an example, biologically active growth factor(s) are present in the periosteum if the angiogenic activity is greater for protein extracts from BRP containing periosteum than a corresponding bone graft not containing periosteum, such as if the angiogenic activity is greater than 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or more greater than the angiogenic activity of protein extracts from a corresponding bone graft composition not containing periosteum. Typically, a biologically active amount of angiogenic growth factor(s) means that a sufficient amount of one or more angiogenic growth factor, and typically a cocktail or mixture of angiogenic growth factors, is present to exhibit a direct physiologic effect to play a role in mediating angiogenesis, such that the growth factor is not denatured or otherwise incapable of participating in mediating angiogenesis. For example, a sufficient amount of an angiogenic growth factor (e.g. VEGF, PDGF, bFGF and/or IGF-1) to have a direct physiologic effect to play a role or participate in mediating angiogenesis can be at least 1 pg/mL, such as at least 2 pg/mL, 5 pg/mL, 10 pg/mL, 20 pg/mL, 30 pg/mL, 40 pg/mL, 50 pg/mL, 60 pg/mL, 70 pg/mL, 80 pg/mL, 90 pg/mL, 100 pg/mL, 200 pg/mL, 300 pg/mL, 400 pg/mL, 500 pg/mL, 600 pg/mL, 700 pg/mL, 800 pg/mL, 900 pg/mL, 1000 pg/mL, 2000 pg/mL, 3000 pg/mL, 4000 pg/mL, 5000 pg/mL, 6000 pg/mL, 7000 pg/mL, 8000 pg/mL, 9000 pg/mL, 10000 pg/mL, 20000 pg/mL, 30000 pg/mL, 40000 pg/mL, 50000 pg/mL or more.

As used herein, "Unit" or "Units of activity" refers to the concentration of protein required to induce half maximal activity or 50% effective dose ($ED_{50}$) (e.g. in pg/mL or ng/mL), For example, a Unit of activity of a protein extract or protein with reference to angiogenic activity is measured from a dose response curve of the protein extract or protein to stimulate angiogenesis, typically in an in vitro HUVEC proliferation assay. The method of expressing the "Unit" potency generally is measured from a dose response curve of a protein or protein extract that is sigmoidal in shape.

As used herein, "specific activity" refers to Units of activity per mg protein. For purposes herein, reference to specific activity is typically with reference to angiogenic activity. For example, the formula for converting the activity as an ED50 in ng/mL to a specific activity in Units/mg is: Specific Activity (Units/mg)=10e6/ED50 (ng/mL).

As used herein, "corresponding bone graft that does not contain periosteum" or "corresponding bone graft containing periosteum processed under denaturing conditions" or variations thereof, refers to a bone graft material that is substantially the same in most respects to BRP, but it differs in the periosteum component of BRP. Hence, it contains the same components as a BRP, including components provided in the same amounts, but differs in the periosteum component of BRP. For example, it is a BRP that contains cancellous bone chips or cancellous bone chips and DBM, provided in the same amounts, but differs in the periosteum component of BRP. In one example, it is a graft that lacks the periosteum component. In another example, it is a graft that contains the periosteum component, but the periosteum component is processed under protein denaturing conditions. Typically, except for the difference in the periosteum component, the methods used to prepare the components of a graft that corresponds to BRP are the same or substantially the same as provided herein.

As used herein, "periosteum processed under denaturing condition or agent" refers to any periosteum that is processed in the presence of a protein denaturing condition or agent. The protein denaturing condition or agent is any that, when exposed to periosteum, affects or influences the degradation or denaturation of protein(s) therein, generally as a result of a loss or partial loss of the tertiary or secondary structure of the protein. The denaturing condition or agent need not be one that is completely deadly to the protein(s), but nevertheless is one that leads to a reduction in the activity of the protein(s) over time. Thus, a condition is denaturing if the activity of the protein(s) is reduced by at least 10%, 20%, 30%, 40%, 50%, 60%, 70%, 80%, 90%, 95% or more in the presence of the condition than in its absence. For example, a condition is denaturing if protein or a protein extract prepared from periosteum exposed to the denaturing condition or agent have a specific activity for mediating angiogenesis that is reduced by at least 10%, 20%, 30%, 40%, 50%, 60%, 70%, 80%, 90%, 95% or more in the presence of the condition than in its absence. A denaturing condition can be due to an external stress or physical condition (e.g., agitation, temperature, time of storage) or can be due to the presence of a denaturing agent. For example, the denaturing condition can be caused by heat, acid or a chemical denaturant. Exemplary denaturing conditions include, but are not limited to, the presence of a strong acid or base, a concentrated inorganic salt (e.g. NaCl, KCl, $MgCl$, $CaCl_2$, $BaCl_2$, $Al_2SO_4$), an organic solvent (e.g., alcohol or chloroform), urea, high or low pH (extremes of pH), elevated temperature (e.g., heat), and/or the presence of excipients that can be denaturing (e.g., phenolic preservatives or detergent). For example, protein denaturation can occur in the presence of high NaCl concentrations, such as concentrations greater than 0.5 M, 1 M, 2 M, 3 M, 4 M, 5 M or greater.

As used herein, "cryopreserved" or "cryopreservation" refers to the process of cooling and storing cells, tissue or organs, such as BRP described herein, at very low temperatures to maintain their viability, for example, at sub-zero temperatures, such as −20° C. to −196° C., inclusive, such as −80±5° C. Cryopreservation can be achieved by methods well known to a skilled artisan. For example, cryopreservation can be achieved by controlled rate and slow freezing or by vitrification methods. Typically, a cryopreservation or vitrification medium containing cryoprotectant is employed prior to storage at the low temperature. For example, a cryopreservation solution can contain dimethyl sulfoxide (DMSO).

As used herein, "immunogenicity" is the ability of a particular substance to provoke an immune response in the body of a human or animal, typically a humoral or cell-mediated immune response.

As used herein, an "immune response" is how a human or animal subject uses its immune system to protect the body from possibly harmful substances by recognizing and responding to antigens. For example, an immune response includes the response generated by an animal subject when lymphocytes identify an antigenic molecule as foreign and induce the formation of antibodies and lymphocytes capable of reacting with the foreign antigen and acting to remove the antigen.

As used herein, "devitalized" with reference to the periosteum refers to periosteum that lacks viable cells. For purposes herein, the processing of the periosteum tissue from the donor subject more than 24 hours post-mortem can result in loss of cell viability. For example, the periosteum component of bone repair product/composition (BRP) provided herein generally contains less than 10%, and generally less than 9%, 8%, 7%, 6%, 5%, 4%, 3%, 2%, 1% or less viable cells.

As used herein, "isolated" or "purified" with reference to a bone component means it is substantially free of tissue material, such as fat and muscle, from the tissue from which the bone is derived.

As used herein, "essentially free" or "substantially free" of endothelial cells or hematopoietic cells with reference to the bone repair composition refers to preparations that are separated from endothelial or hematopoietic cells. In one example, the term essentially free of endothelial cells or hematopoietic cells means that less than 5%, and generally less than 4%, 3%, 2% or 1% of the cells are endothelial cells or hematopoietic cells.

As used herein, the term "assessing" is intended to include quantitative and qualitative determination in the sense of obtaining an absolute value for a characteristic (e.g. property or activity) of a component present in the composition, and also of obtaining an index, ratio, percentage, visual or other value indicative of the level of the property or activity. Assessment can be direct or indirect.

As used herein, a "composition" refers to any mixture. It can be a solution, suspension, liquid, powder, paste, aqueous, non-aqueous or any combination thereof.

As used herein, a "bone disease, disorder, defect or injury" refers to any bone condition in a subject organism resulting from cause or condition including, but not limited to, infections, acquired conditions, genetic conditions, or trauma and characterized by identifiable symptoms. A disease, disorder, defect or injury of interest herein includes any in need of bone growth and/or remodeling.

As used herein, "treating" a subject with a defect, injury, disorder, disease or condition means that the subject's symptoms are partially or totally alleviated, or remain static following treatment. Hence treatment encompasses prophylaxis, therapy and/or cure. Prophylaxis refers to prevention of a potential disease and/or a prevention of worsening of symptoms or progression of a disease.

As used herein, "treatment" means any manner in which the symptoms of a defect, condition, disorder or disease or other indication, are ameliorated or otherwise beneficially altered.

As used herein, the term "subject" refers to an animal, including a mammal, such as a human being.

As used herein, "biocompatible" refers to materials that are not harmful to living tissue or cells. Hence, it is a material that, upon administration in vivo, does not induce undesirable or harmful effects.

As used herein, an "article of manufacture" is a product that is made and sold. As used throughout this application, the term is intended to encompass bone repair compositions contained in articles of packaging.

As used herein, a "kit" refers to a combination of components, such as a combination of the compositions herein and another item for a purpose including, but not limited to, reconstitution, activation, and instruments/devices for delivery, administration, diagnosis, and assessment of a biological activity or property. Kits optionally include instructions for use.

As used herein, the singular forms "a," "an" and "the" include plural referents unless the context clearly dictates otherwise. Thus, for example, reference to a compound comprising or containing "an extracellular domain" includes compounds with one or a plurality of extracellular domains.

As used herein, ranges and amounts can be expressed as "about" a particular value or range. About also includes the exact amount. Hence, "about 5 bases" means "about 5 bases" and also "5 bases."

As used herein, "about" means within an amount that one of skill in the art would consider to be the same or to be within an acceptable range of error. For example, typically, for pharmaceutical compositions, within at least 1%, 2%, 3%, 4%, 5% or 10% is considered about the same. Such amount can vary depending upon the tolerance for variation in the particular composition by subjects.

As used herein, "optional" or "optionally" means that the subsequently described event or circumstance does or does not occur, and that the description includes instances where said event or circumstance occurs and instances where it does not. For example, an optionally substituted group means that the group is unsubstituted or is substituted.

As used herein, the abbreviations for any protective groups, amino acids and other compounds, are, unless indicated otherwise, in accord with their common usage, recognized abbreviations, or the IUPAC-IUB. Commission on Biochemical Nomenclature (see, (1972) *Biochem.* 11:1726).

B. Bone Grafts and Mechanisms of Bone Repair and Healing

Provided herein is a bone repair product (BRP) that is a viable bone matrix containing structural biological matrix, osteoinductive and angiogenic growth factors and endogenous bone cells (i.e. mesenchymal stem cells, osteoprogenitors, osteoblasts, and osteocytes). In particular, BRP provided herein is composed of periosteum, cancellous bone and, optionally, demineralized bone matrix (DBM). In particular examples, the cancellous bone contains viable osteogenic cells. The BRP provided herein exhibits angiogenic properties and can also exhibit one or more osteoconductive, osteoinductive or osteogenic property or properties. For example, BRP provided herein exhibits osteoconductive, osteoinductive, osteogenic and angiogenic properties required for successful bone repair. It does not contain immunogenic components. The BRP provided herein exhibits handling properties so that it is malleable and easy to shape, resulting in a user-friendly product. No additional materials, steps, or washing are required for the product preparation prior to use.

1. Bone Repair and Regeneration

Long bones are composed of a dense outer cortical bone (also called compact bone), which encloses an irregular medullary space or cavity containing cancellous bone. The cortical bone is a dense and compact bone that generally has a higher mineral content than cancellous bone and higher stiffness and strength. The primary structural unit of the cortical bone is the osteon or haversian system, which is made up of cylindrical shaped lamellar bone that surrounds vascular channels called haversian canals. The outer cortical surface is enveloped in the periosteum, which is a connective tissue that contains blood vessels, sensory nerves and dense fibrous tissue and cells that maintain, change and repair the external cortical surface. The cancellous bone (also called spongy bone or trabecular bone) is composed of a branching network of interconnecting bony trabecular elements and contains cells that have osteogenic potential. Osteoprogenitor cells are present in the endosteum that lines the inner surface of the bone and covers the trabeculae of the cancellous bone, and also in the periosteum.

The bones are continually being remodeled by the coordinated actions of osteoclasts and osteoblasts on trabecular and cortical surfaces and in Haversian systems. Remodeling occurs by osteoclastic bone resorption followed by osteoblastic bone formation. First, osteoclasts, which are cells differentiated from hematopoietic stem cells, are activated and excavate a tunnel that runs the length of the long bone. Osteoprogenitors and osteoblast cells closely follows the osteoclasts. Osteoblasts, which are differentiated from mesenchymal stem cells, are attracted to the site and deposit layers of osteoid centripidally along the bone surface of the formed tunnel. Osteoid is the unmineralized organic matrix that subsequently undergoes mineralization by inorganic mineral salts, thereby giving the bone its strength and rigidity. Mature osteoblasts, trapped within the bone matrix as osteoid mineralizes, become osteocytes. Osteocytes are involved in the control of extracellular concentration of calcium and phosphorus, and in other adaptive remodeling processes. The bone first formed by the osteoblasts is woven in nature, but is later replaced by lamellar bone. Eventually, the tunnel constricts as more concentric lamellae are deposited, until only a Haversian canal is left in the center of the new osteon.

In response to injury, bone is able to regenerate and remodel to heal itself. For example, uncomplicated fractures are able to heal without surgical intervention in 6 months or less. The process of healing includes endochrondral or intramembranous ossification. In general, in response to injury, mesenchymal stem cells from the surrounding tissue migrate into the wound site and differentiate into cartilage or bone cells (i.e. osteoblasts). A typical sequence of events includes: hemorrhage; clot formation; dissolution of the clot with concurrent removal of damaged tissues; ingrowth of granulation tissue; formation of cartilage; capillary ingrowth and cartilage turnover; rapid bone formation (bony callus);

and, finally, remodeling of the callus into cortical and trabecular bone. Bone repair, therefore, is a complex process that involves many cell types and regulatory molecules. The diverse cell populations involved in fracture repair include stem cells, macrophages, fibroblasts, vascular cells, osteoblasts, chondroblasts, and osteoclasts.

Thus, the bone healing process occurs by a process involving migration, differentiation and activation of various tissues and cells. While osteogenesis is an important component of bone repair, bone also is highly vascular and bone healing requires the development of microvasculature and microcirculation. Angiogenesis temporally precedes osteogenesis, whereby osteogenesis takes place near newly formed vessels that mediate delivery of osteoprogenitor cells, secrete mitogens for osteoblasts and transport nutrients and oxygen. Thus, in mechanisms of bone healing, angiogenesis play a role in the homeostasis and regeneration of bone tissue (Kanczler and Oreffo (2008) European Cells and Materials, 15:100-114). Many angiogenic growth factors that are involved in forming new vessels are involved in the regeneration process. These include, for example, basic fibroblast growth factor (bFGF), platelet-derived growth factor (PDGF), vascular endothelial growth factor (VEGF), and transforming growth factor betas (TGF-βs).

2. Properties of Bone Graft Supporting Bone Repair

While many bone injuries and fractures can be repaired by the natural ability of bone to regenerate and repair itself, more serious bone defects of fractures require bone grafting methods that mimic the natural processes of bone repair. For example, bone defects caused by trauma, tumor resection, pathological degeneration or congenital deformations can require bone grafting to repair or replace bone defects. Like the natural processes for bone remodeling, bone repair, and regeneration induced by a graft also involves a complex interaction between cells, growth factors, and extracellular matrix.

Thus, for successful bone repair, the graft material should contain all components for natural bone healing. These include components that provide osteoconductive, osteoinductive, osteogenic, and angiogenic properties. These properties can be provided by the particular scaffold and extracellular matrix (ECM) components, bone or progenitor cells provided by the graft, and growth factors and cytokines. Table 1 describes the role of various exemplary growth factors in these processes (see Devescovi et al. (2008) *Chri Organi Mov.*, 92:161-168).

TABLE 1

Growth Factors Involved in Bone Repair

| Growth Factor | Role in Bone Repair |
|---|---|
| BMPs (2, 4, 6, 7) | Osteogenesis/Osteoinduction |
| bFGF | Angiogenesis/Osteogenesis |
| PDGF | Angiogenesis/Osteoconduction |
| VEGF | Angiogenesis/Osteogenesis |
| IGF-1 | Osteogenesis/Osteoinduction/Angiogenesis |
| TGF-β | Angiogenesis/EM synthesis/MSC proliferation | a. Osteoconduction

Osteoconduction is the physical property of a graft to serve as a scaffold to permit bone healing to occur. For example, osteoconduction stimulates the attachment, migration, and distribution of vascular and osteogenic cells within the graft material. Thus, the osteoconductive properties of a graft allows for the ingrowth of a neovasculature and the infiltration of osteogenic precursor cells into the graft site. To be osteoconductive, the material should be biocompatible and the three dimensional structure should provide a physical structure into and along which bone can grow. Examples of materials with osteoconductive properties include bone matrix, such as cancellous or cortical bone grafts. Several bone graft substitutes also exhibit osteoconductive properties, such as coralline hydroxyapatite, collagen-based matrices, calcium phosphate, calcium sulfate, and tricalcium phosphate.

In particular, bone extracellular matrix (ECM), such as provided from cancellous or cortical bone grafts, can provide the osteoconductive scaffold for osseous ingrowth. Bone extracellular matrix is composed of fibrous and non-fibrous proteins, enzymes and minerals that provide bone strength and scaffolding to support cell attachment and sequestering of growth factors. Collagen, a fibrous protein, is the most abundant component (>90%) of bone ECM. Collagen fibrils are essential for hydroxyapatite formation. Over 20 types of collagens are known, and many types are tissue specific. Bone contains almost exclusively Type I collagen with trace amounts of collagen Type III and Type V. Collagens play a role in bone healing. For example, collagens form early bone spicules extending from the fracture edges toward the center of the interfragmental gap. These spicules form the primary mineralization front associated with successful osseous union. Type I collagen fibrils also provide and align factors necessary for cell migration and attachment (Allori et al. (2008) *Tissue Eng. Part B Rev.*, 14:275-283; Boskey and Robey. The composition of bone. In: Rosen C J, ed. *Primer on the Metabolic Bone Diseases and Disorders of Mineral Metabolism*, $8^{th}$ ed. Scarborough, MA: Maine Medical Center Research Institute; 2013:49-58).

Although collagen makes up the majority of the bone matrix, there are more than 160 different non-fibrous ECM proteins that are also present in bone. These include proteoglycans and glycoproteins. Proteoglycans (e.g. decorin and hyaluronan) represent 10% of non-collagenous bone ECM proteins. Structurally, proteoglycans contain a protein core covalently linked to sulfated glycosaminoglycans. During bone repair, proteoglycans are generally aligned with the collagen fibrils and play a role in the mineralization process. Glycoproteins, including fibronectin, contain Arg-Gly-Asp (RGD) sequence that promotes cell adhesion. Fibronectin is detected in the initial fibrin matrix and remains upregulated in the enchondral ossification/osteoid and woven bone stages of bone healing. Fibronectin is localized with osteoblastic cells present at the margins of woven bone (Allori et al. (2008) *Tissue Eng. Part B Rev.*, 14:275-283).

Types and functionality of exemplary bone ECM proteins are summarized in Table 2.

TABLE 2

ECM proteins in Bone

| ECM Protein Family | Functions |
|---|---|
| Collagens (Type I, III, V) | Bone strength, scaffolding, hydroxyapatite formation, matrix organization, cell attachment and migration |
| Proteoglycans (Decorin, Biglycan, Hyaluronan, Aggrecan) | Matrix organization, mineral metabolism/retention, growth factor reservoir |
| Glycoproteins (fibronectin, thrombospondin, osteonectin, bone sialoprotein) | Cell attachment and migration, mineralization initiation/inhibition, mineral metabolism/retention | b. Osteoinduction

Growth factors and cytokines interact with cells during each stage of bone repair to modulate cell migration (chemotaxis), proliferation, and differentiation of various cell types. The presence of bone supportive growth factors that regulates the activity of a bone cell makes bone graft material osteoinductive. In particular, osteoinduction is the ability to recruit host mesenchymal stem cells (MSCs), osteoprogenitors and other bone forming cells to the site of the bone graft or injury, and induce MSCs and osteoprogenitors differentiation into osteoblastic lineage and proliferation.

MSCs have the capacity for self-renewal and are multipotential with the capacity to differentiate into bone, cartilage, adipose, muscle, tendon, and other lineages. In intramembranous bone formation, the stem cells differentiate directly into osteoblasts, which form bone through direct mechanisms. In endochondral bone formation, stem cells differentiate into chondroblasts and chondrocytes, subsequently lay down a cartilaginous extracellular matrix, which then calcifies and remodels into lamellar bone. MSCs are positive for markers CD105, CD146, CD166, CD90, CD73, CD29 and CD44, but do not display expression of markers of hematopoietic origin (CD45, CD14 and CD34), the stem cell marker CD133 or the endothelial cell marker CD144 or CD31 (Baksh (2004); Geregory et al. (2005)).

Osteoinduction is routinely stimulated by osteogenic growth factors that are present in the graft material. Growth factors can signal and promote osteoinduction, and hence bone growth, by recruiting endogenous mesenchymal stem cells (MSCs) to the site of injury or graft and stimulating their bone-forming activity. In particular, bone morphogenic proteins (e.g. BMP-2, -4, -6, -7 or -9), which are part of the transforming growth factor-beta (TGF-β) superfamily, regulate the growth and differentiation of cells in the osteoblast lineage. BMP-2, BMP-6, and BMP-9 possess the greatest osteoinductive activity on MSCs, but BMP-4 and BMP-7 also exhibit limited inductive properties. BMP-2 is one of the earliest genes induced in fracture healing, and plays a role in inducing differentiation of osteoblastic precursors and inhibits myogenic differentiation. BMP-2 has been shown to direct cell fate by regulating different pathways in the periosteum (Yu et al. (2010) Bone, 47:65-73). BMP-7 also stimulates osteo- and chondral-proliferation and differentiation (Onishi et al. (1998) Bone, 22:605-612). BMPs bind to receptors on the membrane of mesenchymal stem cells, which trigger an intracellular signaling pathway, resulting in the transformation of the stem cells into tissue-specific progenitor cells.

In addition to BMPs, other growth factors have been shown to demonstrate osteoinductive activity. Unlike BMPs, these other proteins generally are not osteoinductive alone, but still contribute to bone growth. Such growth factors include, but are not limited to, basic fibroblast growth factor (bFGF), insulin-like growth factor-I and -II (IGF-I and IGF-II), platelet derived growth factor (PDGF) and transforming growth factor-betas (TGF-βs) (Devescovi et al. (2008) Chri Organi Mov., 92:161-168). For example, TGF-β is a family of molecules that are widely expressed, but have their highest levels in bone and platelets. Studies have demonstrated that PDGF stimulates recruitment and proliferation of MSCs, IGF-1 modulates endocrine hormones and growth factor activity of osteoblast precursor cell proliferation and differentiation, and TGF-β1 modulates extracellular matrix secretion of fibrous and non-fibrous proteins and growth factor synthesis (Allori et al. (2008) Tissue Eng Part B Rev., 14:259-273; Mohan and Kesavan (2012) Curr. Osteoporos Rep., 10:178-186). The angiogenic factor, vascular endothelial growth factor (VEGF), discussed further below, also exhibits osteoinductive activity. For example, VEGF can increase MSC proliferation on its own (Pons et al. (2008) Biochem Biophys Res Commun., 376:419-422).

c. Osteogenesis

Osteogenesis is the process of new bone formation by cells from the bone graft material. Osteogenic cells are an integral part of any bone tissue engineering strategy. In addition to attracting these cells by osteoinductive factors as discussed above, these cells can be transplanted into the bone defect. The presence of osteogenic cells means that the graft already contains the cells required to produce bone. The osteogenic component of the graft enhances or accelerates the growth of new bone tissue at the site, and therefore participates in the early stages of the repair or healing process.

Osteogenic cells include mesenchymal stem cells, osteoprogenitor cells and osteoblasts. Osteoprogenitor cells, or preosteoblasts, are stem cells that are alkaline phosphatase (ALP) positive and differentiate into osteoblasts. By virtue of their multipotent capacity, MSCs also have the potential to differentiate into bone cells, which can be induced at the bone graft by the presence of the osteoinductive factors discussed above. Hence, such growth factors also have osteogenic activity. Thus, once implanted, MSCs can differentiate into osteoblasts, which produce new bone matrix. MSCs also naturally secrete bone-inducing growth factors that signal the patient's endogenous cells to migrate and participate in the bone formation process.

The osteogenic property of a bone graft provides the ability of the graft to produce bone independently by virtue of the living cellular components that directly induce bone formation. Both cancellous and cortical grafts can provide cells capable of producing bone, but cancellous autografts with their trabecular structure lined with osteoblasts and large surface area provide for much more potent osteogenesis.

d. Angiogenesis

Angiogenesis is the property of the bone graft to send signals to cells that form the vascular networks of the bone and signal to them to start forming blood vessels. Angiogenic growth factors are necessary for incorporation of a graft. VEGF is one of the predominant growth factors involved in angiogenesis. In addition to its osteoinductive/osteogenic effect, VEGF recruits and promotes proliferation of endothelial cells and endothelial progenitor cells, and promotes new blood vessel formation (Allori et al. (2008) Tissue Eng Part B Rev., 14:259-273; Coultas et al. (2005) Nature, 438:937-945). VEGF recruits endothelial cells to promote blood flow to the avascular tissue graft which provides a route for delivery of osteoprogenitor cells. High levels of VEGF are identified early on in bone healing, such as in the initial hematoma (Beamer et al. (2010) HSS J., 6:85-94). A study has demonstrated that adsorption of VEGF onto a bone graft enhances vascularization and remodeling in a mouse model, and inhibition of VEGF activity inhibits graft incorporation (Ito et al. (2005) Nat. Med., 11:291-297).

Other growth factors also have angiogenic activity. In addition to VEGF, bFGF, PDGF, and IGF-1 are angiogenic growth factors that play roles in tissue revascularization post injury (Coultas et al. (2005) Nature, 438:937-945). For example, basic FGF (bFGF, also called FGF-2) stimulates angiogenesis by promoting proliferation and differentiation of endothelial cells. For example, bFGF induces angiogenesis and stimulates regenerative bone repair when added exogenously to the bone defect (Kigami et al. (2014) J. Oral. Sci., 56:17-22). As indicated above, both VEGF, bFGF and other angiogenic growth factors also have osteoinductive activity to stimulate osteoblastic differentiation.

3. Bone Grafts and Bone-Graft Substitutes

A number of bone grafts or bone-graft substitutes are available and marketed, although only the bone autograft possesses all of the physiological properties (i.e. osteoconduction, osteoinduction, osteogenic and angiogenic) for natural bone healing. Autograft bone is typically recovered from the subject at the time of surgery, typically from the iliac crest, and during a second surgical procedure placed into the site where new bone formation is desired. An autograft includes the osteoconductive, osteoinductive, osteogenic, and angiogenic properties required for bone healing. In particular, an autograft includes living cells, such as viable MSCs that reside within the tissue, the presence of osteoinductive and angiogenic growth factors, and a three-dimensional matrix scaffold. Thus, the bone autograft is the gold standard for bone repair (Nandi et al. (2010) Indian J Med. Res., 132:15-30).

Bone autograft, however, requires a second procedure to harvest the graft that can result in pain and donor site morbidity, extend healing time, and lead to other complications. For example, surgery risks can result from the harvesting procedure, such as major vessel or visceral injuries. Moreover, the amount of harvested bone is limited and often is not sufficient to cover surgical needs. Finally, the quality of bone autograft is often compromised by underlying co-morbidities, such as diabetes, arterial or venous insufficiency, heart disease, renal failure, osteoporosis, or smoking (Zuscik M J (2013) Skeletal Healing. In Primer on the Metabolic Bone Diseases and Disorders of Mineral Metabolism, $8^{th}$ Edition Editor: Rosen, C J 90-98). Therefore, alternatives to a bone autograft have been employed.

No other products for bone repair, however, possess osteoconductive, osteoinductive, osteogenic, and angiogenic properties. For example, other materials used in bone grafting include traditional allografts and xenografts, which are bone grafts from a human or animal tissue donor, respectively. Allografts exhibit osteoconductive properties provided by bone matrix, usually cortical or cancellous bone chips. Traditional allografts are prepared from demineralized bone matrix (DBM) by acid extraction, typically of cortical bone. This extraction results in a DBM in which the inorganic mineral component is removed, leaving a collagen matrix enriched in biologically active osteoinductive proteins. DBM is known to contain a variety of osteoinductive and other bone supportive growth factors, including BMPs, bFGF, IGF-I and II, PDGF and TGF-βs. Thus, DBM allografts provide osteoconduction and osteoinduction properties.

Unlike autografts, traditional allograft materials lack the osteogenic properties relevant for bone healing because they do not contain living osteoprogenitor cells. Advanced allografts have been developed that contain living bone cells and other osteogenic signals. Such products are typically prepared using cancellous bone, which contains multipotent and osteoprogenitor cells within trabeculae. In such allografts, the bone chips containing cells are mixed with demineralized bone.

A problem with existing allograft and other bone graft substitute treatments is that they fail to provide the angiogenic components in a biologically effective amount required for bone healing, and in a manner that simulates natural bone healing processes. Although some angiogenic growth factors are present in the bone matrix, the growth factors generally are not sufficient for angiogenesis for bone healing, in part, because they are sequestered in the bone matrix. It is found herein that high levels of angiogenic growth factors can be provided by the periosteum, which plays a role in facilitating revascularization of the bone after injury. The periosteum is an especially rich source of angiogenic factors necessary to support new blood vessel formation. One mechanism of periosteal response to injury is the release of angiogenic growth factors, including VEGF and bFGF. VEGF and bFGF play a role in blood vessel formation (Coultas et al. (2005) Nature, 15:937-45). Since, the angiogenic growth factors (and other bone growth factors) present in the periosteum are ready for immediate release, the growth factors are more readily available to support angiogenesis for bone healing.

As demonstrated herein, periosteum has been prepared that retains beneficial bone repair angiogenic growth factors, which are naturally present in the periosteum. As shown, the procedures for preparing the periosteum employ minimal manipulation of the material to ensure proteins are not denatured. For example, Example 1 demonstrates that both VEGF and bFGF are expressed in high levels in the isolated and processed periosteum. As shown herein, the levels of various angiogenic growth factors (e.g. VEGF, bFGF or PDGF) are 2- to 5-fold more or greater than levels present in a viable bone allograft control lacking periosteum. These growth factors are stable upon freezing and thawing of BRP as demonstrated in Example 9. The higher amounts of angiogenic growth factors, and presence in periosteum, also correlate with the ability of BRP to induce blood vessel formation as assessed in an in vitro tube formation assay. In contrast, viable bone allograft control lacking periosteum was insufficient to induce tube formation. In addition, periosteum also contains additional matrix and growth factors necessary for bone healing.

The periosteum, however, is a highly cellularized, vascularized and innervated tissue. The high levels of vascularization and presence of neuronal tissue correlates with a high level of immunogenic material. For example, the use of allogenic cellular periosteum requires the use of immunosuppressants because of the immunogenic activity (Liu et al. (1994) Microsurgery, 15:87-92). Thus, in BRP provided herein, devitalized periosteum is provided that does not contain any immunogenic cells. Thus, the periosteum, and resulting BRP, is not immunogenic.

In addition to the biochemical properties of the periosteum that provide a source of angiogenic growth factors to support bone repair, it was also found that the natural physical properties of the periosteum support the handling of BRP. For example, the periosteum swells once isolated from the bone and when placed in a physiologic solution, and exhibits a sticky consistency after mincing. The stickiness allows the periosteum pieces to adhere to themselves and to the bone fragments in BRP. In particular, it is found herein that this property is provided by the periosteum from the long bone, but not from the flat bone (see Example 1). Thus, in particular examples of BRP provided herein, the product contains periosteum from the long bone, which exhibits a stickiness after isolation and mincing. In other examples, periosteum from the flat bone can be used as a source of angiogenic growth factors and other proteins that support bone repair. In such examples, additional biocompatible materials that support the handling properties can be included in BRP as described herein.

Hence, provided herein is a BRP that contains isolated periosteum containing biologically active angiogenic growth factor(s) and cancellous bone matrix fragments containing viable osteogenic cells. In some cases, DBM also can be included in the product, which is enriched for matrix proteins and growth factors for osteoconductive and osteoinductive activities, respectively. By virtue of the sticky periosteum component, and/or presence of other biocompatible components to achieve desired handling properties, the resulting BRP is malleable and shapeable so that the periosteum and bone fragments are adhered. The cancellous bone contains viable cells that support new osteogenesis. The cancellous bone, and optionally DBM, contain osteoconductive matrix and osteoinductive growth factors. The inclusion of the periosteum provides angiogenic growth factors necessary to support new blood vessel formation, as well as other matrix and growth factors that support bone healing. The BRP exhibits all of the physiological properties (i.e. osteoconductive, osteoinductive, osteogenic and angiogenic) for natural bone healing. Thus, the BRP provided herein is a replacement for autograft, and eliminates the requirement for a second surgical procedure and associated risks and limitations of autografts.

C. Bone Repair Product Composition and Formulations

Provided herein is a bone repair product (BRP) composition that contains cancellous bone fragments and periosteum containing angiogenic growth factor(s). The angiogenic growth factors are biologically active. Thus, BRP provided herein is an angiogenic viable bone matrix, such that the resulting BRP mediates angiogenesis. Without angiogenesis, revascularization cannot occur and bone repair can be delayed or compromised. In addition, the cancellous bone fragments can contain viable osteogenic cells so that BRP contains all the elements to be osteogenic. The BRP can optionally contain fragments of demineralized bone matrix (DBM). Thus, in examples provided herein, BRP can contain cancellous bone fragments containing viable osteogenic cells, DBM fragments, and periosteum containing angiogenic growth factor(s). The DBM can be from cancellous or cortical bone. In addition to the angiogenic properties, the resulting BRP can provide all of the properties required for bone healing, such that the BRP promotes or supports osteogenesis, osteoinduction, osteoconduction, and angiogenesis.

In BRP product provided herein, the ratio of periosteum to bone matrix (cancellous bone or cancellous/DBM) can be provided at any ratio in order to achieve a product that is malleable and shapeable, such that bone fragments and periosteum are adhered together, bones are not separated or lost, and BRP retains its ability to mold into different shapes. Methods of combining the components are described further below in Section D. In some examples, the periosteum is present as a weight percentage (mass/mass) in the product of 1% to 75%, such as 1% to 50%, 2% to 40%, 3% to 30%, 4% to 25% or 5% to 20%, each inclusive, such as at least 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75% or more. For example, the weight ratio (grams/grams) of periosteum to bone matrix (cancellous bone or cancellous bone/DBM) is greater than or is about 0.05:4, 0.05:3, 0.05:2, 0.05:1.5, 0.05:1, 0.1:4, 0.1:3, 0.1:2, 0.1:1.5, 0.2 to 4, 0.2:3, 0.2:2, 0.2:1.5, 0.2:1, 0.3:4, 0.3:3, 0.3:2, 0.3:1.5, 0.3:1, 0.4:4, 0.4:3, 0.4:2, 0.4:1, 0.5:4, 0:5:3, 0.5:2, 0.5:1.5 0.5:1 or more. For example, the product can contain 0.1 g to 0.5 g, inclusive (5% to 20%, inclusive) periosteum and about 1 g to 2 g, inclusive, bone matrix (cancellous bone or cancellous bone/DBM).

In some examples, in addition to the periosteum and cancellous bone, such as cancellous bone containing viable osteogenic cells, BRP contains DBM. The DBM can be from cancellous or cortical bone. In such examples, the DBM does not exceed 45% by weight of the cancellous bone. For example, the DBM component in BRP is present as a weight percent of the cancellous bone of less than or about less than 45%, such as less than 44%, 43%, 42%, 41%, 40%, 39%, 38%, 37%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1% or less. Typically, the DBM component in BRP is present as a weight percent of the cancellous bone of 1% to 45%, for example, 5% to 45%, 5% to 40%, 5% to 30%, 5% to 25%, 10% to 45%, 10% to 40%, 10% to 30%, 10% to 25%, 15% to 45%, 20% to 45%, 20% to 40%, 20% to 30%, 20% to 25%, 25% to 45%, 25% to 40%, 25% to 30%, 30% to 45%, 30% to 40% or 40% to 45%, each inclusive.

By virtue of the combination of bone matrix and periosteum, BRP contains angiogenic and osteoinductive growth factors that are biologically active. The presence of growth factors in BRP represents the natural combination or cocktail of growth factors that are present in the bone, including periosteum, that contribute to bone healing. Indeed, overexpression of a single growth factor does not result in bone repair (Lieberman et al. (1999) *J Bone Joint Surg. Am.*, 81:905-917), pointing to the requirement for a cocktail of growth factors that complement and enhance each other's activity to achieve complete bone repair. Growth factors present in BRP include, but are not limited to, one or more of VEGF, PDGF, bFGF, IGF-1, IGF-2, TGF-β1, BMP-2 and BMP-7. For example, the Examples demonstrate that protein extracts of BRP contain the exemplary bone reparative growth factors set forth in Table 2, as assessed by Enzyme-Linked Immunosorbent Assay (ELISA). Thus, BRP provided herein contains a number of exemplary bone reparative growth factors, including osteogenic/osteoinductive and angiogenic growth factors. The presence of these growth factors indicate that BRP has osteoinductive and angiogenic properties.

It is understood that the growth factors represent growth factors naturally present in the periosteum and bone. Thus, BRP contains a combination of more than one growth factor. The growth factors, including angiogenic growth factors, in BRP retain their biologic activity. For example, as described in Section D below, the components of BRP, such as periosteum and bone, are prepared by processing in physiologic solution and under conditions whereby the tissue retains biologically active growth factors. These growth factors can work in synergy in BRP to effect the angiogenic and osteoinductive properties of BRP. Since the growth factors present in the bone component are sequestered and not readily available, it is the presence of biologically active bioavailable growth factors, including angiogenic growth factors, provided from the periosteum component that ensure their immediate release at the site of implantation and injury to promote the angiogenic processes for bone healing.

BRP provided herein containing periosteum with biologically active growth factor(s) exhibits greater angiogenic activity than a corresponding bone graft that does not contain periosteum or that contains periosteum prepared or processed in the presence of a denaturing condition or agent. For example, BRP provided herein exhibits at least 0.5-fold, 1-fold, 2-fold, 3-fold. 4-fold, 5-fold, 10-fold, 20-fold, 30-fold, 40-fold, 50-fold, 60-fold, 70-fold, 80-fold, 90-fold, 100-fold, 500-fold, 1000-fold or more angiogenic activity to mediate angiogenesis than a corresponding bone graft that does not contain periosteum or that contains periosteum prepared or processed in the presence of a denaturing condition or agent. For example, the specific activity for mediating angiogenesis of protein extracts from BRP provided herein is at least 0.5-fold, 1-fold, 2-fold, 3-fold. 4-fold, 5-fold, 10-fold, 20-fold, 30-fold, 40-fold, 50-fold, 60-fold, 70-fold, 80-fold, 90-fold, 100-fold, 500-fold, 1000-fold or more than the specific activity for mediating angiogenesis of protein extracts from a corresponding bone graft that does not contain periosteum or that contains periosteum prepared or processed in the presence of a denaturing condition or agent.

The particular types and concentration of the growth factor(s) in the product will depend on the particular donor. Typically, the concentrations of each growth factor can independently be at least 1 pg/mL, such as at least 2 pg/mL, 5 pg/mL, 10 pg/mL, 30 pg/mL, 40 pg/mL, 50 pg/mL, 60 pg/mL, 70 pg/mL, 80 pg/mL, 90 pg/mL, 100 pg/mL, 200 pg/mL, 300 pg/mL, 400 pg/mL, 500 pg/mL, 600 pg/mL, 700 pg/mL, 800 pg/mL, 900 pg/mL, 1000 pg/mL, 2000 pg/mL, 3000 pg/mL, 4000 pg/mL, 5000 pg/mL, 6000 pg/mL, 7000 pg/mL, 8000 pg/mL, 9000 pg/mL, 10000 pg/mL, 20000 pg/mL, 30000 pg/mL, 40000 pg/mL, 50000 pg/mL or more and each will generally independently vary from or from about 1 pg/mL to 50000 pg/mL, such as 10 pg/mL to 10000 pg/mL or 50 pg/mL to 5000 pg/mL, such as from or from about 100 pg/mL to 1000 pg/mL, 100 pg/mL to 800 pg/mL, 100 pg/mL to 600 pg/mL, 100 pg/mL to 400 pg/mL, 100 pg/mL to 200 pg/mL, 200 pg/mL to 1000 pg/mL, 200 pg/mL to 800 pg/mL, 200 pg to 600 pg/mL, 200 pg/mL to 400 pg/mL, 400 pg/mL to 1000 pg/mL, 400 pg/mL to 800 pg/mL, 400 pg/mL to 600 pg/mL, 600 pg/mL to 1000 pg/mL, 600 pg/mL to 800 pg/mL or 800 pg/mL to 1000 pg/mL of BRP. The growth factors present in the product include, for example, VEGF, bFGF, PDGF, IGF-1, IGF-2, TGF-β1, BMP-2 and/or BMP-7, and each can be present in a concentration range as set forth above. As an example, BRP provided herein can contain VEGF and the concentration of VEGF can be at least 1 pg/mL, such as at least 2 pg/mL, 5 pg/mL, 10 pg/mL, 30 pg/mL, 40 pg/mL, 50 pg/mL, 60 pg/mL, 70 pg/mL, 80 pg/mL, 90 pg/mL, 100 pg/mL, 200 pg/mL, 300 pg/mL, 400 pg/mL, 500 pg/mL, 600 pg/mL, 700 pg/mL, 800 pg/mL, 900 pg/mL, 1000 pg/mL, 2000 pg/mL, 3000 pg/mL, 4000 pg/mL, 5000 pg/mL, 6000 pg/mL, 7000 pg/mL, 8000 pg/mL, 9000 pg/mL, 10000 pg/mL, 20000 pg/mL, 30000 pg/mL, 40000 pg/mL, 50000 pg/mL or more, and generally will vary from or from about 50 pg/mL to 5000 pg/mL, such as from or from about 100 pg/mL to 1000 pg/mL, 100 pg/mL to 800 pg/mL, 100 pg/mL to 600 pg/mL, 100 pg/mL to 400 pg/mL, 100 pg/mL to 200 pg/mL, 200 pg/mL to 1000 pg/mL, 200 pg/mL to 800 pg/mL, 200 pg to 600 pg/mL, 200 pg/mL to 400 pg/mL, 400 pg/mL to 1000 pg/mL, 400 pg/mL to 800 pg/mL, 400 pg/mL to 600 pg/mL, 600 pg/mL to 1000 pg/mL, 600 pg/mL to 800 pg/mL or 800 pg/mL to 1000 pg/mL of BRP. It is understood that these levels are just provided as examples, and that the exact levels will depend on the particular growth factor, the particular donor, the method used for protein extraction (e.g. lysis method), the method used to quantify protein levels and other factors within the level of the skilled artisan.

By virtue of the presence of biologically active growth factors provided by the periosteum and bone component, BRP provided herein contains a greater concentration of a growth factor (e.g. angiogenic growth factors) than the concentration of the same growth factor in a corresponding product that does not contain periosteum (e.g. a product containing cancellous bone matrix only or cancellous/DBM only). In particular, BRP provided herein contains a greater concentration of an angiogenic growth factor (e.g. VEGF, bFGF, PDGF, or IGF-1) than the concentration of the same growth factor in a corresponding product that does not contain periosteum. For example, BRP contains a concentration of angiogenic growth factor (e.g. VEGF, bFGF, PDGF, or IGF-1) that is at least 0.1-fold, 0.5-fold, 1-fold, 1.5-fold, 2-fold, 2.5-fold, 3-fold, 3.5-fold, 4-fold, 4.5-fold, 5-fold, 6-fold, 7-fold, 8-fold, 9-fold, 10-fold or more greater than the concentration of the same angiogenic growth factor in a corresponding bone graft not containing periosteum. Any one or more, two or more, three or more, or four or more of VEGF, bFGF, PDGF and/or IGF-1 or other angiogenic growth factor can be present in the increased amount compared to a corresponding product that does not contain periosteum. As an example, BRP contains VEGF in a concentration that is at least 0.1-fold, 0.5-fold, 1-fold, 1.5-fold, 2-fold, 2.5-fold, 3-fold, 3.5-fold, 4-fold, 4.5-fold, 5-fold, 6-fold, 7-fold, 8-fold, 9-fold, 10-fold or more greater than the concentration of the same growth factor in a corresponding bone graft not containing periosteum. It is understood that in such examples, the cancellous bone and DBM in the compared products are substantially the same, but the products differ in the periosteal component of the bone and DBM (e.g. lacks the periosteum). In such examples, the presence of growth factors is assessed under substantially the same conditions. Due to the increased levels of angiogenic growth factors in BRP, BRP exhibits angiogenic activity to induce angiogenesis, which is not achieved by a corresponding bone graft prepared using the same procedure but not containing periosteum.

In examples of BRP provided herein, in addition to providing angiogenic growth factors and other growth factors and matrix components, the periosteum in BRP composition can be sticky. As discussed elsewhere herein, the stickiness is a natural quality of periosteum, particularly from the long bone, when it swells in a physiologic solution and is minced or cut into smaller pieces. When combined with bone fragments, the bone fragments are held together by the periosteum, providing a uniform and packable material. This means that no other wetting agents or materials are required in order to generate a uniform and shapeable material that can be packed into bony voids. In some examples, further wetting agents or materials can be added to the composition provided herein to contribute to the handling properties if desired or necessary.

The BRP provided herein is not immunogenic. In particular, BRP is substantially free of endothelial cells or hematopoietic cells and other immunogenic components. For example, BRP product is substantially free of cells that are positive for the marker CD31, which is a marker for endothelial cells (Suarez et al. (2007) *Journal of Immunology*, 179:7488-7496). Endothelial cells can initiate an immune response, and are associated with tissue rejection (Marlene L. Rose (2001). The Immune Response to Endothelial Cells. Marlene L. Rose (Ed.) In *Transplant-Associated Coronary Artery Vaculopathy* (Chapter 3, pages 71-89)). Also, BRP is substantially free of cells that are positive for the marker CD45, which is a marker present on all hematopoietic cells, including hematopoietic stem cells (HSCs) and osteoclasts that are of hematopoietic origin (Koretzky (1993) *FAES Journal*, 7:420-426; and Taylor and Bank (1988) *Cryobiology*, 25:1-17). For example, BRP is substantially free of hematopoietic cells of the myeloid or lymphoid lineage, for example, as detected by markers CD34 (hematopoietic stem cell), CD33 (myeloid), CD19 or CD20 (B cells), CD14 or CD33 (macrophage), CD11c or CD123 (dendritic cells), CD56 (NK cells), CD66b (granulocyte), CD235a (erythrocyte), or CD3, CD4 or CD8 (T cell). Macrophages and other hematopoietic immune cells can secrete inflammatory cytokines, such as TNF-α, which can contribute to tissue immunogenicity. For example, the addition of exogenous TNF-α triggers allograft rejection (Shen and Glostein (2009) *J Am. Soc. Nephrol.*, 20:1032-1040), and reduction of TNF-α by depletion with anti-TNFα antibodies or suppression of TNF-α secretion can reduce tissue immunogenicity (Dickinson et al. (1994) *Cytokine*, 6:141-6; Wang et al. (2002) *Transplantation*, 74:772-8). The presence of macrophages plays a role in allograft rejection (Bajot et al. (1988) *Clin. Exp. Immunol.*, 71:138-43 and Sekine et al. (1997) *J Immunol.*, 159:4084-93), and depletion of allogenic donor tissue macrophages decreases the level of inflammatory cytokine secretion, such as TNF-α (Sekine et al. (1997) *J Immunol.*, 159:4084-93).

The BRP can be formulated in any form suitable for implantation onto bone. The BRP composition can contain a biocompatible carrier or physiologically acceptable liquid or solution. Examples of suitable pharmaceutical carriers are described in "Remington's Pharmaceutical Sciences" by E. W. Martin. For example, such carriers and liquids include, but are not limited to, saline, phosphate buffered saline (PBS), lactated Ringer's PlasmaLyte® A, aqueous dextrose and glycerol solutions, waters and oils (e.g. those of petroleum, animal, vegetable or synthetic origin, such as peanut oil, soybean oil, mineral oil and sesame oil). Examples of aqueous liquids include Sodium Chloride Injection, Ringers Injection, Isotonic Dextrose Injection, Sterile Water Injection, Dextrose and Lactated Ringers Injection. Typically, the composition contains physiological saline solution. In addition, BRP also can be optionally formulated with other biocompatible excipients as desired depending on the particular application. For example, BRP can contain human serum albumin (HSA). In other examples, BRP does not contain or is essentially free of carriers, liquids or other excipients.

The amount or volume of carrier, liquid or excipient that is contained in BRP composition is an amount or volume that does not affect the properties of BRP to be malleable and shapeable, such that the bone fragments and periosteum remain adhered together, bones are not separated or lost and BRP retains its ability to mold into different shapes. For example, the amount of a physiologically acceptable liquid, such as a physiological saline solution, is an amount that only just covers BRP so that BRP is submerged in the liquid, but otherwise excess liquid is removed. Hence, BRP contains a minimal volume of liquid sufficient to coat or saturate the product.

In particular examples, BRP product contains a cryoprotectant for cryopreservation of the product, which is used for storage of BRP so that it can be preserved and stored while retaining its viability (e.g. viability of osteogenic cells). For example, BRP can contain a cryopreservation or vitrification medium or solution containing the cryoprotectant. Suitable cryoprotectants include, but are not limited to, dimethy sulfoxide (DMSO), glycerol, a glycol, a propylene glycol, an ethylene glycol, propanediol, polyethylene glycol (PEG), 1,2-propanediol (PROH) or a mixture thereof. In some examples, the cryopreservation solution can contain one or more non-cell permeating cryopreservative, including but not limited to, polyvinyl pyrrolidone, a hydroxyethyl starch, a polysaccharide, a monosaccharide, an alginate, trehalose, raffinose, dextran, human serum albumin, Ficoll, lipoproteins, polyvinyl pyrrolidone, hydroxyethyl starch, autologous plasma or a mixture thereof.

It is understood that the cryoprotectant, and amount or volume of cryoprotectant solution, is therapeutically acceptable for pharmaceutical use. A suitable cryopreservation solution contains a cryopreservative in an amount of at least about 0.001% to 100%, by volume, such as an amount from or from about 2% to about 20%, 5% to about 10% by volume, each inclusive, and generally at least 2%, at least 5%, at least 10% or more by volume. For example, the cryopreservative can be DMSO and the cryopreservation solution can contain DMSO at a concentration of at least 2% by volume, at least 5% by volume, at least 10% by volume or more. Further, the cryopreservation solution can contain serum albumin or other suitable proteins to stabilize the membrane during the freeze-thaw process and to reduce the damage to cells, thereby maintaining viability. Serum albumin can be human serum albumin or bovine serum albumin. In some examples, the cryopreservation solution can contain from or from about 1% to about 20% serum albumin or other suitable proteins, such as 1% to 10%, 1% to 5%, 5% to 20% or 5% to 10% serum albumin or other suitable proteins. In addition, the cryopreservation solution can contain a physiological solution, such as a physiological buffer or saline, for example phosphate buffer saline. It is understood that the cyropreservation solution, including the amount or volume of cyropreservation solution, is such that it does not affect the properties of BRP to be malleable and shapeable, such that the bone fragments and periosteum remain adhered together, bones are not separated or lost and BRP retains its ability to mold into different shapes. For example, BRP contains a minimal volume of cryopreservation or vitrification medium or solution that only just covers, coats or saturates the product. As discussed in Section D, if desired, BRP can be washed prior to use, such as in a physiologic solution (e.g. physiologic saline or phosphate buffered saline), to remove residual cryoprotectant.

A description of the components in BRP, and their properties or characteristics, are described in the following subsections.

1. Components of Bone Repair Product (BRP)

a. Periosteum

BRP contains periosteum, which is a source of angiogenic growth factors and other growth factors and matrix proteins. Hence, the periosteum is a rich source of osteoinductive and angiogenic growth factors, which play a role in bone repair (Devescovi et al. (2008) *Chir Organi. Mov.*, 92:161-168). The periosteum covers most bone surfaces, except articular surfaces, tendon insertion points, and sesamoid bones. It is connected by Sharpey fibers. The periosteum, however, is not uniform across bone surfaces. There are differences in periosteum thickness and structure throughout the skeleton, but it is most abundant in high fracture risk areas such as long bones (Allen et al. (2004) Bone, 35:1003-1012). One of its roles is to provide a barrier between bone and the surrounding tissue. While connected to the bone, it prevents the free exchange of liquids. Once released from the bone, the barrier function is lost and the periosteum becomes osmotic and swells when placed into a physiological saline solution (Evans et al. (2013) *Tissue Engineering: Part B*, 19:147-159; Allen et al. (2004) *Bone*, 35:1003-1012; McBride et al. (2011) *Journal of Biomechanics*, 44:1954-1959).

The periosteum component of BRP contains one or more growth factors that support angiogenesis and/or have osteoinductive/osteogenic activity. Such growth factors include, but are not limited to, VEGF, PDGF, bFGF, and/or IGF-1. It is understood that the growth factors represent growth factors naturally present in the periosteum. Thus, BRP contains a combination of more than one growth factor. These growth factors can work in synergy with each other, and those present in the bone matrix, to effect the angiogenic and osteoinductive properties of BRP. As described in Section D, BRP is produced by processing the periosteum in a physiologic solution and under conditions to retain the biological activity of growth factors and proteins in the periosteum. For example, as shown in Examples herein, the presence of biologically active angiogenic growth factor(s) provided from the periosteum render BRP sufficient to support angiogenesis (see e.g. Example 11).

The particular type or concentration of the growth factor(s) in periosteum component of BRP will depend on the particular donor. Typically, the concentrations of each growth factor can independently be at least 1 pg/mL, such as at least 2 pg/mL, 5 pg/mL, 10 pg/mL, 30 pg/mL, 40 pg/mL, 50 pg/mL, 60 pg/mL, 70 pg/mL, 80 pg/mL, 90 pg/mL, 100 pg/mL, 200 pg/mL, 300 pg/mL, 400 pg/mL, 500 pg/mL, 600 pg/mL, 700 pg/mL, 800 pg/mL, 900 pg/mL, 1000 pg/mL, 2000 pg/mL, 3000 pg/mL, 4000 pg/mL, 5000 pg/mL, 6000 pg/mL, 7000 pg/mL, 8000 pg/mL, 9000 pg/mL, 10000 pg/mL, 20000 pg/mL, 30000 pg/mL, 40000 pg/mL, 50000 pg/mL or more, and each will generally independently vary from or from about 1 pg/mL to 50000 pg/mL, such as 10 pg/mL to 1000 pg/mL or 50 pg/mL to 5000 pg/mL, such as from or from about 100 pg/mL to 1000 pg/mL, 100 pg/mL to 800 pg/mL, 100 pg/mL to 600 pg/mL, 100 pg/mL to 400 pg/mL, 100 pg/mL to 200 pg/mL, 200 pg/mL to 1000 pg/mL, 200 pg/mL to 800 pg/mL, 200 pg to 600 pg/mL, 200 pg/mL to 400 pg/mL, 400 pg/mL to 1000 pg/mL, 400 pg/mL to 800 pg/mL, 400 pg/mL to 600 pg/mL, 600 pg/mL to 1000 pg/mL, 600 pg/mL to 800 pg/mL or 800 pg/mL to 1000 pg/mL of the periosteum. It is understood that these levels are just provided as examples, and that the exact levels will depend on the particular growth factor, the particular donor, the method used for protein extraction (e.g. lysis method), the method used to quantify protein levels and other factors within the level of the skilled artisan In examples of BRP provided herein, the periosteum component in BRP is in a form suitable to adhere to itself and the bone matrix fragments to form a malleable and shapeable product. Thus, the periosteum is one that can be provided in a physical form that exhibits a sticky consistency. The periosteum is provided in small pieces to result in the periosteum component of BRP having a uniform sticky consistency. As described further in Section D, this can be achieved by chopping, mincing, or cutting up the periosteum into pieces, such as with a scalpel blade or other sharp blade, until a uniform consistency is achieved. If the periosteum is too sticky, it can be further minced or chopped to a uniform sticky consistency. The handling properties of BRP also is provided by a periosteum that can swell (e.g. as evidenced when added to a physiological solution, such as physiological saline). Generally, a periosteum that exhibits these characteristics (i.e. stickiness and ability to swell) is not fibrous and is free from muscles and fat when isolated. Typically, the periosteum in BRP is provided from long bone. In contrast, for purposes of providing handling properties, the periosteum is generally not provided from flat bone, which does not exhibit the appropriate characteristics for handling of BRP. For example, as described in Examples, periosteum from flat bone (i.e. iliac crest) is difficult to separate from attached muscles and fat, is fibrous and does not exhibit a sticky consistency when minced and does not swell.

In some examples, the periosteum component of BRP providing biologically active growth factors and proteins is provided by periosteum from the flat bone or periosteum from the flat bone and long bone. In such examples, if necessary, BRP can contain an additional biocompatible component or components that provide the handling properties (e.g. shapeability, malleability and packability) of BRP. The biocompatible component can be natural or synthetic. For example, non-limiting examples of such suitable biocompatible components include, but are not limited to, gelatin, Type I collagen, bone marrow aspirate, blood, platelet-rich plasma (PRP), fibrin glue, bone putty, poly caprolactone, poly ethylene glycol, alginates, chitosans, chondroitin sulfates or animal derived periosteum. In some cases, the mixture of periosteum from the flat bone and long bone is sufficient to provide the handling properties of BRP. In such examples, the ratio of periosteum from long bone to flat bone in BRP is at least 0.5:1, such as at least 1:1, 1.5:1, 2:1, 3:1, 4:1, 5:1 or more.

The periosteum component in BRP also can be devitalized. The periosteum is normally a highly cellularized, vascularized and innervated tissue, and therefore contains hematopoietic and endothelial cells that can be immunogenic. This problem renders the periosteum a seemingly unsuitable source for inclusion in a bone graft. It is found herein, however, that periosteal cells die within 24 hours post-mortem, but the activity of growth factors present in periosteal tissue is retained for a longer time to permit process of periosteum containing biologically active growth factors. Thus, BRP is prepared in a manner in which the cyropreservation of the product does not occur within 24 hours post-mortem. Typically, donors are processed for periosteum, and other bone matrix components, more than 24 hours post-mortem, but generally no more than 72 hours post-mortem. Accordingly, in BRP provided herein, the periosteum is substantially free of cells. Thus, the only viable osteogenic cells in BRP are derived from the cancellous bone (discussed below).

b. Cancellous Bone Matrix

BRP contains cancellous bone chips or fragments. The cancellous bone can contain viable bone chips or can be devitalized. Typically, the cancellous bone contains viable osteogenic cells, which include mesenchymal stem cells, osteoprogenitor cells, osteoblasts, and osteocytes. For example, the cancellous bone is mineralized and retains viable cells. In such examples, the cancellous bone provides osteogenic properties to BRP.

Cancellous bone is available in a range of porosities based on the location in the body from which the bone is harvested. Highly porous cancellous bone can be harvested from various areas such as the iliac crest, while less porous bone can be harvested from areas such as the tibial condyle femoral head, and calcaneus. The cancellous bone in BRP is from any cancellous bone bearing source such as, but not limited to, vertebral bodies in the spine, the iliac crest, long bone (e.g. femur or tibia), ribs, talus or calcaneus. For example, the cancellous bone in BRP can be from the long bone of the femur. The cancellous bone, and periosteum (above), typically are obtained from a single bone sample. For example, the components are derived from long bone of femurs.

The cancellous bone in BRP is provided in small fragments or chips of different sizes, typically from or from about 100 μm to 5 mm in size, and generally in fragments or chips less than 4 mm, 3 mm, or 2 mm in size. Different sized bone chips are believed to have different osteoconductive activities (Gruskin et al. (2012) *Advanced Drug Delivery Reviews*, 64:1063-1077). Also, different sized bone chips facilitate the packable handling properties of BRP into bony voids. Typically, the bone chips are greater than 400 µm in size, such as generally greater than 500 µm or 600 µm in size. For example, the cancellous bones chips or fragments are 400 µm to 3 mm, 400 µm to 2.5 mm, 400 µm to 2 mm, 400 µm to 1.5 mm, 400 µm to 1 mm, 600 µm to 3 mm, 600 µm to 2.5 mm, 600 µm to 2 mm, 600 µm to 1.5 mm, 600 µm to 1 mm, 1 mm to 3 mm, 1 mm to 2.5 mm, 1 mm to 2 mm, 2 mm to 3 mm, 2 mm to 2.5 mm or 2.5 mm to 3 mm. In particular examples, the cancellous bone chips or fragments are greater than 600 µm and less than 2 mm. The presence of different size bone chips allows for there to be more overall bone per cc in BRP. The more chips per cc, the higher the cell number per cc in BRP from a given donor.

In examples of BRP containing cancellous bone containing viable osteogenic cells, at least one viable cell is present. The presence of viable cells is ensured due to the procedures for processing of bone chips by blending as described below, the processing in the presence of a physiologic solution and by the cryopreservation techniques employed. For example, cell viability can range from or from about 1% to 100%, such as greater than or equal to 1%, 5%, 10%, 20%, 30%, 40%, 50%, 60%, 70%, 80%, 90% or more of the cells are viable. In particular examples, the viability of cells in BRP is 70% or greater viable cells, such as generally greater than 75%, 80%, 81%, 82%, 83%, 84%, 85%, 86%, 87%, 88%, 89%, 90%, 91%, 92%, 93%, 94%, 95%, 96%, 97%, 98%, 99% or more. Such cell viability can be present in BRP prior to freezing or after freezing and post-thaw. For example, BRP provided herein can be frozen or cryopreserved, whereby the viability of cells in the post-thaw BRP can range from or from about 1% to 100%, such as greater than or equal to 1%, 5%, 10%, 20%, 30%, 40%, 50%, 60%, 70%, 80%, 90% or more of the cells are viable. For example, a post-thaw BRP provided herein that has been frozen or cryopreserved can contain 70% or greater viable cells, such as generally greater than 75%, 80%, 81%, 82%, 83%, 84%, 85%, 86%, 87%, 88%, 89%, 90%, 91%, 92%, 93%, 94%, 95%, 96%, 97%, 98%, 99% or more. Typically, viability of cells in BRP, including viability of cells in BRP post-thaw, is greater than 90%, and generally 92% to 98%, such as at least 93%, 94%, 95%, 96%, 97% or more.

In examples of BRP provided herein, the cancellous bone provided in BRP contains a sufficient number of viable osteogenic cells to exhibit osteogenic activity. Typically, with reference to cells per cc in BRP, viable cells present in BRP provided herein is at least $1\times10^3$ cells/cc, such as at least $5\times10^3$ cells/cc, $1\times10^4$ cells/cc, $5\times10^4$ cells/cc, $1\times10^5$ cells/cc, $2\times10^5$ cells/cc, $3\times10^5$ cells/cc, $4\times10^5$ cells/cc, $5\times10^5$ cells/cc, $6\times10^5$ cells/cc, $7\times10^5$ cells/cc, $8\times10^5$ cells/cc, $9\times10^5$ cells/cc, $1\times10^6$ cells/cc, $1.5\times10^6$ cells/cc, $2\times10^6$ cells/cc, $3\times10^6$ cells/cc, $4\times10^6$ cells/cc, $5\times10^6$ cells/cc, $6\times10^6$ cells/cc, $7\times10^6$ cells/cc, $8\times10^6$ cells/cc, $9\times10^6$ cells/cc, $1\times10^7$ cells/cc or more. For example, BRP can contain $1\times10^3$ cells/cc to $1\times10^7$ cells/cc, $1\times10^4$ cells/cc to $1\times10^7$ cells/cc, $1\times10^5$ cells/cc to $1\times10^7$ cells/cc, such as $2\times10^5$ cells/cc to $8\times10^6$ cells/cc, $5\times10^5$ cells/cc to $6\times10^6$ cells/cc or $7\times10^5$ cells/cc to $5\times10^6$ cells/cc.

Viability of cells in BRP can be assessed by standard techniques known to skilled artisan. Such methods include qualitative and quantitative methods, including, but not limited to, trypan blue staining, live/dead staining using a detectable (e.g. fluorescent) cell permeable dye, or an assay using a tetrazolium salt (e.g. MTT or WST). For example, as exemplified in the Examples, the cell permeable dye Calcein-AM can be used to fluorescently visualize live/dead cells. In such a method, bone chips are labeled with Calcein-AM. Calcein-AM is converted to calcein, a green fluorescent protein, by viable cells in situ labeled. In live cells, the nonfluorescent Calcein-AM is converted to a green-fluorescent calcein after acetoxymethyl ester hydrolysis by intracellular esterases. This can be determined prior to cryopreservation of BRP, after frozen storage and thaw of BRP or both.

As indicated, viable cells present in BRP are osteogenic cells, such as one or more of mesenchymal stem cells, osteoprogenitor cells, osteoblasts, or osteocytes. For example, markers of mesenchymal stem cells include, but are not limited to, CD166 (ALCAM, SB10), CD90 (Thy-1), CD44 (hyaluronan receptor), CD105 (SH2), CD147 (neuroregulin), Stro-1, CD54 (intercellular adhesion molecule 1), or combinations thereof. Markers of osteoprogenitor cells include tissue non-specific alkaline phosphatase positive (TNAP). For example, based on cell-type-specific markers, BRP is $CD105^+$ (marker of mesenchymal stem cells), CD166 (mesenchymal stem cells), and tissue non-specific alkaline phosphatase positive ($TNAP^+$; osteoprogenitor or osteoblast). As discussed above, the cancellous bone, and hence BRP, is essentially free of hematopoietic cells ($CD45^+$) and endothelial cells ($CD31^+$).

The cancellous bone component of BRP also contains one or more growth factors that support angiogenesis and/or have osteoinductive/osteogenic activity, i.e. angiogenic and/or osteoinductive growth factors. Such growth factors include, but are not limited to, VEGF, PDGF, bFGF, IGF-1, IGF-2, TGF-β1, BMP-2, BMP-7 and/or parathyroid hormone (PTH). In particular, the cancellous bone contains BMPs, which are not detected in periosteum and which are among the major osteoinductive growth factors. It is understood that the growth factors represent growth factors naturally present in the cancellous bone. Thus, cancellous bone contains a combination of more than one growth factor. These growth factors can work in synergy with each other, and those present in the periosteum, to effect the angiogenic and osteoinductive properties of the BRP.

As indicated, the particular type or concentration of the growth factor(s) in the cancellous bone component of the product will depend on the particular donor. Typically, the concentrations of each growth factor in cancellous bone fragments of BRP can independently be at least 1 pg/mL, such as at least 2 pg/mL, 5 pg/mL, 10 pg/mL, 30 pg/mL, 40 pg/mL, 50 pg/mL, 60 pg/mL, 70 pg/mL, 80 pg/mL, 90 pg/mL, 100 pg/mL, 200 pg/mL, 300 pg/mL, 400 pg/mL, 500 pg/mL, 600 pg/mL, 700 pg/mL, 800 pg/mL, 900 pg/mL, 1000 pg/mL, 2000 pg/mL, 3000 pg/mL, 4000 pg/mL, 5000 pg/mL, 6000 pg/mL, 7000 pg/mL, 8000 pg/mL, 9000 pg/mL, 10000 pg/mL, 20000 pg/mL, 30000 pg/mL, 40000 pg/mL, 50000 pg/mL or more, and each will generally independently vary from or from about 1 pg/mL to 50000 pg/mL, such as 10 pg/mL to 1000 pg/mL or 50 pg/mL to 5000 pg/mL, such as from or from about 100 pg/mL to 1000 pg/mL, 100 pg/mL to 800 pg/mL, 100 pg/mL to 600 pg/mL, 100 pg/mL to 400 pg/mL, 100 pg/mL to 200 pg/mL, 200 pg/mL to 1000 pg/mL, 200 pg/mL to 800 pg/mL, 200 pg to 600 pg/mL, 200 pg/mL to 400 pg/mL, 400 pg/mL to 1000 pg/mL, 400 pg/mL to 800 pg/mL, 400 pg/mL to 600 pg/mL, 600 pg/mL to 1000 pg/mL, 600 pg/mL to 800 pg/mL or 800 pg/mL to 1000 pg/mL of the cancellous bone fragments. It is understood that these levels are just provided as examples, and that the exact levels will depend on the particular growth factor, the particular donor, the method used for protein extraction (e.g. lysis method), the method used to quantify protein levels and other factors within the level of the skilled artisan As shown in Examples herein, such growth factors are present in BRP (see Example 9).

c. Demineralized Bone

In some examples, demineralized bone matrix (DBM) can be included in BRP provided herein. DBM preparations are known to a skilled artisan, including for their use in orthopedic medicine to promote the formation of bone. For example, DBM is used in the repair of fractures, in the fusion of vertebrae, in joint replacement surgery, and in treating bone destruction due to underlying disease such as rheumatoid arthritis. DBM promotes bone formation in vivo by osteoconductive and osteoinductive processes. The osteoinductive effect of implanted DBM composition results from the presence of active growth factors present on the isolated collagen-based matrix. These factors include members of the TGF-β (including BMPs) and IGF protein families. Particular examples of osteoinductive factors include TGF-0, IGF-1, IGF-2, BMP-2, BMP-7, and parathyroid hormone (PTH). Like cancellous bone, other angiogenic factors also can be present.

Hence, demineralized bone matrix contains most of the non-mineralized components of bone. As described in Section D, it is obtained by the process of acid extraction, which removes the mineral components of bone. This leaves many of the components that give bone matrix its osteoinductive potential, such as BMPs. It also retains its collagen structure, which also gives it osteoconductive properties. The removal of the mineral content increases the bioavailability of growth factors (Pietrzak et al. (2009) *Cell Tissue Bank,* 12:81-88). In addition, if the bone architecture is maintained, the DBM contributes, along with the cancellous bone, to the scaffolding necessary to support new bone growth.

The DBM can be from cancellous bone or from cortical bone. In some examples, the DBM can derive from cancellous bone. The cancellous bone can be from any cancellous bone bearing source such as, but not limited to, vertebral bodies in the spine, the iliac crest or ilieum, long bone (e.g. femur, tibia), flat bones, talus or calcaneus. In other examples, the DBM can derive from cortical bone. The cortical bone can derive from any cortical bone structure, such as the shaft of long bones, flat bones of the skull, ribs or surfaces of the ilium. Cortical bone can be obtained from long bones, such as the diaphyseal shaft of the femur, tibia, and fibula. The DBM, and also the cancellous bone containing viable cells (above) and periosteum (above), typically are obtained from a single donor subject. All components can be derived from a single bone sample (e.g. long bone of femurs) or from multiple bone sources.

The DBM in BRP is provided in small fragments or chips of 100 μm to 5 mm in size. For examples, DBM is provided as bone fragments or chips of 5 mm or smaller, such as 4 mm or smaller, 3 mm or smaller, 2 mm or smaller, 1 mm or smaller, 900 μm or smaller, 800 μm or smaller, 700 μm or smaller, 600 μm or smaller, 500 μm or smaller, 400 μm or smaller, 300 μm or smaller or 200 μm or smaller. In some examples of preparing BRP provided herein, when DBM is derived from cancellous bone it typically is derived from the same bone sample as the bone containing viable cells. For example, the DBM is prepared from bone chips or fragments not employed for providing cancellous bone containing viable osteogenic cells. In such examples, the DBM can be less than 600 μm in size, such as less than 500 μm, 400 μm, 300 μm or 200 μm in size, but generally greater than 100 μm in size. In some examples, the DBM is provided as bone chips or fragments that are greater than 100 μm in size and less than 600 μm in size.

Methods of demineralizing bone are known in the art and described in Section D below. DBM contains the collagen matrix of the bone together with acid insoluble proteins, including BMPs and other growth factors. Thus, the DBM, together with cancellous bone, provides an osteoconductive matrix and exhibits osteoinductive potential, inducing the infiltration and differentiation of mesenchymal stem cells and osteoprogenitor cells from the surrounding tissues. Such growth factors include, but are not limited to, VEGF, PDGF, bFGF, IGF-1, IGF-2, TGF-β1, BMP-2, BMP-7 and/or parathyroid hormone (PTH). In particular, together with the cancellous bone, the DBM contains BMPs and is considered the major source of BMPs, which are among the major osteoinductive growth factors. It is understood that the growth factors represent growth factors naturally present in the bone matrix. Thus, DBM contains a combination of more than one growth factor. These growth factors can work in synergy with each other, and those present in the periosteum and cancellous bone containing viable cells, to effect the angiogenic and osteoinductive properties of BRP.

As indicated, the particular type or concentration of the growth factor(s) in the DBM component of the product will depend on the particular donor. Typically, the concentrations of each growth factor in the DBM component of the product can independently be at least 1 pg/mL, such as at least 2 pg/mL, 5 pg/mL, 10 pg/mL, 30 pg/mL, 40 pg/mL, 50 pg/mL, 60 pg/mL, 70 pg/mL, 80 pg/mL, 90 pg/mL, 100 pg/mL, 200 pg/mL, 300 pg/mL, 400 pg/mL, 500 pg/mL, 600 pg/mL, 700 pg/mL, 800 pg/mL, 900 pg/mL, 1000 pg/mL, 2000 pg/mL, 3000 pg/mL, 4000 pg/mL, 5000 pg/mL, 6000 pg/mL, 7000 pg/mL, 8000 pg/mL, 9000 pg/mL, 10000 pg/mL, 20000 pg/mL, 30000 pg/mL, 40000 pg/mL, 50000 pg/mL or more, and each will generally independently vary from or from about 1 pg/mL to 50000 pg/mL, such as 10 pg/mL to 1000 pg/mL or 50 pg/mL to 5000 pg/mL, such as from or from about 100 pg/mL to 1000 pg/mL, 100 pg/mL to 800 pg/mL, 100 pg/mL to 600 pg/mL, 100 pg/mL to 400 pg/mL, 100 pg/mL to 200 pg/mL, 200 pg/mL to 1000 pg/mL, 200 pg/mL to 800 pg/mL, 200 pg to 600 pg/mL, 200 pg/mL to 400 pg/mL, 400 pg/mL to 1000 pg/mL, 400 pg/mL to 800 pg/mL, 400 pg/mL to 600 pg/mL, 600 pg/mL to 1000 pg/mL, 600 pg/mL to 800 pg/mL or 800 pg/mL to 1000 pg/mL of the DBM component. It is understood that these levels are just provided as examples, and that the exact levels will depend on the particular growth factor, the particular donor, the method used for protein extraction (e.g. lysis method), the method used to quantify protein levels and other factors within the level of the skilled artisan. As shown in Examples herein, such growth factors are present in a BRP product containing DBM (see Example 9).

2. Packaging and Articles of Manufacture

BRP provided herein can be packaged as articles of manufacture, containing packaging material (e.g. container) and a BRP composition provided herein. The articles of manufacture also can contain a label that indicates it can be used for treating a bone disease, disorder, defect or injury, such as any described in Section G. Instructions for use can be provided. For example, instructions can be provided for procedures for thawing BRP before use (see Section G).

The articles of manufacture provided herein contain packaging materials. Packaging materials for use in packaging bone graft products are well known to those of skill in the art. Examples of pharmaceutical packaging materials are containers, which include, but are not limited to, bottles, tubes, jars, vials, syringes, trays and any other suitable packaging material that can hold BRP. The particular packaging material can be empirically chosen by skilled artisan based on the particular storage condition, volume of BRP, shape of BRP and other relevant factors within the level of a skilled artisan to empirically consider and determine. For example, the packaging material is a straight sided jar with a wide mouth to permit access and complete sample retrieval. In another form, the packaging material is a tray to allow easy access, sample retrieval and a simple thaw procedure. Generally, the packaging material is a material that is suitable for storage at room temperature or ambient temperature of 18° C. to 25° C., refrigerated conditions of 2° C. to 8° C., or under freezing conditions for cryopreservation, such as at temperatures of about or less than −20° C., such as generally −20° C. to −196° C., inclusive, for example −80±5° C. For example, the packaging material can be made up of polypropylene or polycarbonate. Typically, the packaging material is sterile or can be sterilized. The material is compatible with DMSO and other cryoprotectant solutions.

The BRP composition is provided in an amount effective for implantation, such as for filling a bony void. For example, BRP is provided in a volume that is from or from about 0.2 cc to 100 cc, such as generally at least 0.2 cc, for example at least 0.2 cc, 0.3 cc, 0.4 cc, 0.5 cc, 0.6 cc, 0.7 cc, 0.8 cc, 0.9 cc, 1 cc, 1.5 cc, 2 cc, 2.5 cc, 3 cc, 3.5 cc, 4 cc, 4.5 cc, 5 cc, 6 cc, 7 cc, 8 cc, 9 cc, 10 cc, 20 cc, 30 cc, 40 cc, 50 cc or more. In some examples, BRP is provided in a weight of from or from about 0.2 g to 100 g, such as generally at least 0.2 g, for example at least 0.2 g, 0.3 g, 0.4 g, 0.5 g, 0.6 g, 0.7 g, 0.8 g, 0.9 g, 1 g, 1.5 g, 2 g, 2.5 g, 3 g, 3.5 g, 4 g, 4.5 g, 5 g, 6 g, 7 g, 8 g, 9 g, 10 g, 20 g, 30 g, 40 g, 50 g or more.

As indicated elsewhere herein, BRP is shapeable and malleable. BRP can be provided in any shape that is suitable for the particular packaging. For example, BRP can be shaped flat, as a round ball or as a square or other four-sided shape. In particular examples herein, BRP is shaped as a round ball in order to permit easier removal from the packaging material, such as a jar.

D. Method of Preparing Bone Repair Product Composition

Provided herein are methods of preparing BRP containing periosteum containing angiogenic growth factor(s), cancellous bone, such as cancellous bone containing viable osteogenic cells and, optionally, DBM, such as BRP described above in Section C.

Bone used to prepare BRP can be obtained from any physiologically appropriate source. In some examples, bone is obtained from non-human animal sources (i.e. for xenogenic implantation in a human subject), such as cows and pigs. Typically, bone is obtained from human subjects for allogenic implantation in a human subject. In such examples, bone can be obtained from human cadavers following appropriate ethical and legal requirements. Such human bone material is available from a variety of tissue banks. For example, for preparation of BRP, materials are typically provided for clinical use from a "tissue bank," which harvest bone from human cadavers (donated and managed according to proper ethical and legal standards). Such tissues include, for example, knees-en-bloc or legs-en-bloc. Processing of the donor tissue typically begins within 96 hours of death, and generally within 72 hours of death in order to ensure and preserve osteogenic cell viability and functionality. Typically, tissue is not received or isolated for processing in first 24 hours of death, which accounts for lack of viable cells in processed periosteal tissue.

Generally, serological testing of donor is performed. For example, allografts currently undergo stringent testing, including sterility, to ensure the safety of the grafts. Screening of cadaveric donors can involve a detailed past medical, social, and sexual histories as well as testing for agents, including but not limited to, hepatitis C antibody, hepatitis B surface antigen, hepatitis B core antigen, HIV-1, HIV-2, syphilis, human T-lymphocyte virus I antibody, or HIV p24 antigen.

For preparation of components in BRP, any bone source bearing periosteum, cancellous bone or cortical bone can be employed. The bone source can be the same or different for each component. For example, the cancellous bone can be from any cancellous bone bearing source such as, but not limited to, vertebral bodies in the spine, the iliac crest, femur, tibia, or ribs. The cortical bone can derive from any cortical bone structure, such as, for example, the shaft of long bones (e.g., as the diaphyseal shaft of the femur and tibia), flat bones of the skull, ribs and surfaces of the ilium. For preparation of the periosteum, the long bone is contemplated, since periosteum from the long bone retains the physical properties for handling of BRP, such as stickiness and swelling. Typically, the type of bone is the same for all components. For example, long bones (e.g. femurs) can be selected as a primary tissue source because they contain all components for inclusion in BRP, including periosteum. In most cases, bone components in BRP are from the same donor.

Prior to processing bone components, the bone source is washed and treated with povidone iodine (i.e. betadine) to reduce bioburden levels. The bone source is manipulated to remove soft tissues, such as adipose, muscle, fascia, ligaments and tendons, while preserving the integrity of the bone structure and preventing damage to the periosteum. For example, the femur (i.e. long bone) can be separated from the tibia and used as the bone source. The resulting isolated bone source can be used to further isolate, process and prepare the periosteum, cancellous bone and, optionally, DBM components of BRP.

1. Processing and Preparing Bone Components a. Processing Periosteum

Periosteal tissue can be derived from any bone source containing periosteum, such as long bones or flat bones. Periosteal tissue can be removed from bone by any appropriate means, including by dissociating or loosening from bone using a sharp and fine tool, such as a scalpel, and further scraping with a sharp tool, such as a scalpel, blade, spatula, periosteal elevator or by abrading with a wire brush. Once removed, the periosteal tissue is placed in a physiologic solution in a volume that is sufficient to cover the tissue. The physiologic solution is one that is capable of preserving stability of proteins in periosteum in order to limit denaturation, proteolysis, unfolding, aggregation, and other structural changes to protein composition that would destabilize protein and reduce biological activity. Exemplary physiological liquids or solutions include, but are not limited to, saline, phosphate buffered saline (PBS), lactated Ringer's PlasmaLyte® A, aqueous dextrose and glycerol solutions, waters and oils (e.g. petroleum, animal, vegetable or synthetic origin, such as peanut oil, soybean oil, mineral oil and sesame oil). For example, physiological liquids or solutions include Sodium Chloride Injection, Ringers Injection, Isotonic Dextrose Injection, Dextrose and Lactated Ringers Injection. Typically, the periosteum is placed in a physiological saline solution. In particular examples, to retain biological activity of periosteal proteins, the periosteum is not processed in 5 M sodium chloride solution or other protein denaturing solution.

Prior to processing isolated periosteum, it is cleaned to remove any residual materials or tissue, for example, any that could affect the ability of the periosteum to form a sticky and uniform consistency when processed as described below. For example, residual muscle and fat tissue can be removed using a finger, scalpel, scissor, forceps or other suitable instrument that does not damage or destroy the integrity and properties of the periosteum. During such procedures, the periosteal tissue generally is maintained in the physiologic solution to preserve the integrity of the tissue.

Typically, the periosteum is derived from the long bone, which exhibits properties of swelling and stickiness that contribute to the handling properties of BRP. When placed in a physiologic solution, the natural properties of the periosteum allow it to swell. To achieve sufficient swelling of the periosteum for handling purposes, the periosteum is incubated or placed in the chilled or room temperature physiologic solution for more than 10 minutes, such as more than 20 minutes, 30 minutes, 40 minutes, 50 minutes, 60 minutes or more. The time period can be longer, since the periosteum cannot over swell. Generally, the periosteum is not incubated in solution for so long to affect the integrity of the periosteum and stability of proteins present in periosteum. In some cases, periosteum can be derived from flat bone, which does not exhibit the same swelling/sticky properties. In such examples, the periosteum is nevertheless similarly processed in a physiologic solution in a manner to preserve the integrity of the periosteum and stability of proteins present in periosteum. In such examples, additional biocompatible agents can be included in the combined BRP as described below to provide the appropriate handling properties.

Periosteum is processed into pieces by mincing or cutting the tissue into small pieces to achieve a uniform consistency using a sharp tool, such as a scalpel, blade, or scissors. The choice and manner of cutting or mincing the periosteum is one that prevents loss of periosteum tissue, can control the size of the pieces, and is able to sufficiently cut or mince the tissue to a uniform size. For example, mincing or cutting of periosteal tissue can be performed using two scalpels. The periosteal tissue is minced or cut until a uniform consistency is achieved. Generally, the periosteal tissue, such as provided from the long bone, is processed until it is sufficiently sticky so that the periosteum can adhere to itself and to bone chips of fragments. If the product is too sticky, it can be further minced or cut to a uniform consistency that achieves the desired stickiness.

Once processed, periosteum can be stored in physiological solution until it is ready to be combined with other components, such as generally at refrigerated temperature, such as 2° C. to 8° C. In some cases, processed periosteum can be stored at sub-zero temperatures, such as about or less than −20° C. or about or less than −80° C.±5° C. It is understood that the length of storage is not so long to reduce or destroy the integrity of the tissue or stability of proteins. It is within the level of a skilled artisan to empirically determine the maximum time period for which the periosteum is stored after isolation and processing. If necessary, additional physiologic solution can be added to the periosteum pieces to ensure they are covered.

b. Processing Cancellous Bone Containing Osteogenic Cells

Cancellous bone can be harvested from any cancellous bone bearing source. Such sources include, but are not limited to, vertebral bodies in the spine, the iliac crest, long bone (e.g. femur or tibia), ribs, talus or calcaneus. For example, cancellous bone can be harvested from the long bone (i.e. femur). The cortical shell of the bone is removed.

Cancellous bone is processed into small bone chips or fragments using any method or procedure that can chop or cut bone. Such methods include, but are not limited to, blending, milling, grating, or grinding. Generally, it is desired that cancellous bone is processed into bone chips or fragments of greater than 100 µm in size but generally less than 5 mm in size. If larger bone chips or fragments are produced they can be further processed into smaller fragments, or can be removed from the product by size exclusion, such as by using various sieves as described below. To permit processing of the bone into smaller pieces containing viable osteogenic cells as described below, cancellous bone can initially be cut into pieces of size of no larger than 2 cm×3 cm, and generally about 2 cm×2 cm. Isolated bone pieces that are initially cut into approximately 2-3 cm sized pieces are more conducive to manipulation in procedures used to prepare smaller bone chips.

In particular examples of the method of preparing cancellous bone chips or fragments for inclusion in BRP, cancellous bone is processed using a blender. As described in Example 2, unlike other methods of processing cancellous bone into bone chips, the blender is able to successfully process the bone into small chips or fragments without loss of bone material and without damage to integrity of the processing apparatus. In addition, unlike standard cancellous bone mills or a grater that produce bone chips of a specific size so that all pieces are similar in size (e.g. 4 mm), the use of a blender produces bones chips of various sizes and shapes. Provision of bone chips of different sizes and shapes for inclusion in BRP improves handling properties of BRP for implantation or packing into a bony void. In addition, the generation of different size bone chips also allows there to be more overall bone per cc in BRP product. The more bone chips per cc means there is a higher cell number per cc, and thus an increased or greater osteogenic activity of BRP compared to bone grafts containing a lesser concentration of osteogenic cells.

If desired, bone chips that are processed to be of different size, such as occurs by blending, can be selected to contain a desired range of size. Any method that achieves size exclusion can be employed. Generally, sieves of various known sizes can be employed, for example, by passing processed bone chips through the sieves and collecting either the residual bone chips that are too large to fit through the sieve or the bone chips that pass through the sieve. In such methods, a physiologic solution, such as any described elsewhere herein (e.g. physiologic saline) can be used to wash the bone chips through the sieve. The process of sieving bone chips can be performed a plurality of times, and can be performed sequentially with different sieves. Using such procedures, cancellous bone chips or fragments can be prepared that are sized to be from or from about 100 µm to 5 mm, such as generally greater than 400 µm in size, such as generally greater than 500 µm or 600 µm in size. For example, cancellous bone chips or fragments can be prepared that are sized from or from about 400 µm to 3 mm, 400 µm to 2.5 mm, 400 µm to 2 mm, 400 µm to 1.5 mm, 400 µm to 1 mm, 600 µm to 3 mm, 600 µm to 2.5 mm, 600 µm to 2 mm, 600 µm to 1.5 mm, 600 µm to 1 mm, 1 mm to 3 mm, 1 mm to 2.5 mm, 1 mm to 2 mm, 2 mm to 3 mm, 2 mm to 2.5 mm or 2.5 mm to 3 mm. In particular examples, the cancellous bone chips or fragments are selected to have a size that is greater than 600 μm and less than 2 mm, 3 mm or 4 mm.

During the processes of processing the bone and/or after collection of bone chips the bone is washed to remove any fat on the bone and residual blood, including blood cells, endothelial cells and hematopoietic cells. Any physiologic solution can be used to wash the bone chips, such as any described elsewhere herein (e.g. physiologic saline). In particular examples, washing of bone chips can be achieved during the processing of the bone chips using a blender, since the blender permits the addition of large volumes of liquid solution without affecting the quality of cutting bone into small pieces. In contrast, other methods of processing bone chips, such as using a coffee mill, do not permit the use of liquid or other solution. Not only does this mean that such a processing would not provide a step to wash the cells, but it also can result in a loss of cells because the apparatus becomes too warm and is harsh on the processed bone. In addition, the use of a physiologic wash solution during the size exclusion separation(s) also facilitates the removal of residual blood. Further wash steps also can be performed after collection of processed bone chips. Wash steps can be repeated a plurality of times until the bone chips are sufficiently free of fat and residual blood, including blood cells, such as endothelial cells and hematopoietic cells. The one or more wash steps used throughout the processing of cancellous bone ensures that the bone chips are sufficiently removed of contaminating materials, while retaining viable osteogenic cells that are embedded in the bone matrix.

In some examples, bone chips can be treated with a loosening agent, such as collagenase and/or a digestive enzyme as described in U.S. Patent Publication No. US2014/0056857. In such examples, the bone chips can be treated with the loosening agent, such as collagenase and/or a digestive enzyme, for a time and at a concentration to loosen the osteogenic cells contained in the bone matrix, but not release the osteogenic cells from the bone matrix. In one example, the bone is treated with the loosening agent, such as collagenase and/or a digestive enzyme, at a concentration of from or from about 0.1 mg/mL to about 3.0 mg/mL or 1.0 mg/mL to 3.0 mg/mL. The bone can be treated for a period of time from or from about 5 minutes to 3 hours. For example, the bone chips can be treated with a loosening agent, such as collagenase and/or a digestive enzyme, at a concentration of 1.0 mg/mL for 10 minutes. In other examples, cancellous bone chips containing viable osteogenic cells are included in BRP without treating with a loosening agent (e.g. collagenase or other digestive enzyme).

Once processed, cancellous bone containing viable osteogenic cells can be stored until it is ready to be combined with other components. Storage is at a temperature and for a time to retain viability of osteogenic cells present in bone matrix of cancellous bone chips. For example, bone chips can be held at 2° C. to 8° C. for several hours in a physiological solution. It is within the level of a skilled artisan to empirically determine the maximum time period and temperature for which the cancellous bone chips can be stored after isolation and processing. If necessary, additional physiologic solution can be added to the cancellous bone chips to ensure they are covered. Prior to combining with the other components, the excess solution can be decanted.

c. Processing Demineralized Bone Matrix (DBM)

Demineralized bone matrix (DBM) can be prepared in any suitable manner. DBM can be prepared from cortical bone or cancellous bone. In some examples, DBM is prepared from cancellous bone that is harvested from any cancellous bone bearing source, including, but not limited to, vertebral bodies in the spine, the iliac crest, femur, tibia, and ribs. In other examples, DBM is prepared from cortical bone from any cortical bone structure, such as the shaft of long bones (e.g. the diaphyseal shaft of the femur, tibia and fibula), flat bones of the skull, or surfaces of the ilium. Typically, DBM is prepared from cancellous bone or cortical bone derived from the long bone (e.g. femur).

The bone (cancellous or cortical bone) is processed into small bone chips or fragments using any method or procedure that can chop or cut bone. The bone can be processed into chips or fragments of an appropriate size before or after demineralization. Such methods include, but are not limited to, blending, milling, grating, or grinding. Generally, it is desired that bone is processed into bone chips or fragments of greater than 100 μm in size but generally less than 5 mm in size. If larger bone chips or fragments are produced they can be further processed into smaller fragments, or can be removed from the product by size exclusion, such as by using various sieves of desired sizes. For example, bone chips can be processed to produce bone chips that are less than 5 mm, such as less than 4 mm, 3 mm, 2 mm, 1 mm, 900 μm, 800 μm, 700 μm, 600 μm, 500 μm, 400 μm, 300 μm, 200 μm or less. For example, sieves can be employed to produce bone chips that are of an appropriate size. The process of selecting bone chips by size can be performed a plurality of times, and can be performed sequentially with different sieves. Generally, bone chips are at least 100 μm in size.

In examples of preparing DBM, bone chips or fragments to prepare DBM can be prepared from the same donor bone as used to prepare the cancellous bone above, such a long bone (e.g. femur). In one example, the cortical shell that is removed from cancellous bone is used as the source of DBM and bone chips or fragments from cortical bone generated to prepare DBM. In another example, bone chips or fragments to prepare DBM are obtained from cancellous bone isolated and processed using procedures as described above. For example, a portion of cancellous bone chips as processed using procedures described in subsection D.1.b, above, can be employed to prepare DBM. In other examples, unused bone chips obtained from processing the cancellous bone described in subsection D.1.b, above, can be used to prepare DBM. In such an example, the larger or smaller fragments or bone chips that were excluded (e.g. by sieves) in the cancellous bone component provided above can be used to prepare DBM. Typically, the smaller fragments or bone chips excluded (e.g. by sieves) in the cancellous bone component provided above can be used to prepare DBM. For example, bone chips to prepare DBM can be bone chips or fragments selected to be less than 600 μm in size, such as less than 500 μm, 400 μm, 300 μm, or 200 μm in size, but generally greater than 100 μm in size. In some examples, bone chips or fragments for preparing DBM are selected that are greater than 100 μm in size and less than 600 μm in size.

Bone chips or fragments are cleaned using a suitable cleaning procedure that cleans the bone but maintains the osteoinductivity of the bone. The cleaning procedures can be employed prior to processing bone into smaller sizes as described above, or after selection and collection of bone chips and fragments of the desired size. Exemplary cleaning procedures include, but are not limited to, a series of chemical steps with nonionic detergents, hydrogen peroxide and/or alcohol for various times and temperatures (DePaula et al. (2005) *Cell and Tissue Banking*, 6:287-298). Generally, cleaning procedures employ hydrogen peroxide, typically from or from about 1.5% to 3% hydrogen peroxide. In some cases, the cleaning procedure can be performed under agitation, such as ultrasonic agitation. For example, hydrogen peroxide can be added to submerge bone chips or fragments and incubated for up to 1 hour, generally less than 30 minutes, such as at least 3 minutes, and generally at least 5 minutes, for example, from or from about 5 minutes to 15 minutes. The treated bone can be rinsed with a physiologic solution, such as PBS or saline, to remove the hydrogen peroxide prior to transfer to the demineralization process.

In another example, defatting/disinfecting procedures using an aqueous solution capable of acting as a defatting agent, such as ethanol, can be used. Ethanol is a good solvent for lipids and the water is a good hydrophilic carrier to permit the solution to penetrate more deeply into the bone particles. The aqueous ethanol solution can disinfect the bone by killing vegetative microorganisms and viruses. Typically, at least about 10% to 40% by weight of water (i.e. about 60 to 90 weight percent of defatting agent, such as alcohol) is present in the defatting disinfection solution. For example, the defatting solution is from or from about 60 to about 85 percent alcohol or about or at least 70 weight percent alcohol.

DBM can be prepared in any suitable manner using any of a variety of methods known in the art, for example, methods using acids, chelating agents, or electrolysis (Lewandrowski et al. (1996) *J Biomed. Mater. Res.*, 31:365-372; Lewandrowski et al. (1997) *Cal. Tiss. Int.*, 61:294-297; Lewandrowski et al. (1997) *J Orthop. Res.*, 15:748-756; Reddi et al. (1972) *PNAS*, 69:1601-1605). Typical methods include acid extraction of minerals from bone resulting in loss of most of the mineralized components but retention of collagen and noncollagenous proteins. Other methods include alkaline extraction of bone. For example, chemical treatments to effect demineralization include those using hydrochloric acid, ethylene diamine tetraacetic acid (EDTA), peracetic acid or citric acid.

In one example, the bone is immersed in acid to effect demineralization. For example, bone chips can be added to a sufficient volume of acid solution to completely submerge or cover the bones. Typically, a ratio of acid that is at least 2 parts acid to 1 part bone is employed, and generally at least 3 parts, 4 parts, 5 parts, 6 parts, 7 parts, 8 parts, 9 parts, 10 parts or more acid to 1 part bone is employed. Acids that can be employed in this step include inorganic acids such as hydrochloric acid, as well as organic acids such as formic acid, acetic acid, peracetic acid, citric acid, or propionic acid. Typically, from or from about 0.1 N to 3 N hydrochloric acid is employed, for example, 0.1 N to 1 N, such as at least 0.5 N or 0.6 N hydrochloric acid. To achieve demineralization, the bone chips can be incubated in acid for 30 minutes to 12 hours, such as 30 minutes to 2 hours, generally at least 60 minutes. The incubation can be under refrigerated or ambient (e.g. room temperature) conditions. For example, incubation with acid can be at a temperature of from or from about 2° C. to 8° C. The extent of demineralization into the bone surface can be controlled by adjusting the treatment time, temperature of the demineralizing solution, concentration of the demineralization solution and agitation intensity during treatment.

After treatment, the acid can be removed. Residual acid can be neutralized, such as by using sodium phosphate buffer, such as at a concentration of 5 mM, or other neutralization buffer. DBM can be rinsed with a physiologic solution, such as PBS or saline, to remove any unwanted acid. The rinse or wash steps can be repeated a plurality of times as desired. Once processed, DBM can be stored until it is ready to be combined with other components. For example, DBM can be held at 2° to 8° C., such as for several hours. It is within the level of a skilled artisan to empirically determine the maximum time period and temperature for which the DBM can be stored after isolation and processing. If necessary, additional physiologic solution can be added to the DBM to ensure they are covered. Prior to combining with the other components, the excess solution can be decanted or removed.

2. Combining Components to Produce Bone Repair Product (BRP)

After isolating and processing each component separately for inclusion in BRP, the components, periosteum, cancellous bone, such as cancellous bone containing viable osteogenic cells and, optionally, DBM, are combined. Generally, the components are processed in parallel. For combining the components to prepare BRP product provided herein, the periosteum component is provided as a ratio of bone matrix (cancellous bone or cancellous/DBM) at any ratio in order to achieve a product that is malleable and shapeable, such that bone fragments and periosteum are adhered together, bones are not separated or lost, and BRP retains its ability to mold into different shapes. The exact ratio or percentage need not be known. For example, it is found that by combining the components in their entirety obtained from a single donor bone as described herein, a BRP is produced that is malleable and shapeable. It also is understood that some variability can exist between preparations in terms of the ratio or percentage of periosteum to bone matrix, depending on the particular donor and other factors. It is within the level of a skilled artisan to know if the product is sufficiently malleable and shapeable.

In some examples, the total weight of each component can be determined prior to combining together so that the components can be combined in a manner to achieve a desired weight ratio. In one example, the periosteum is combined with bone matrix (cancellous bone or cancellous/DBM) as a weight percentage (mass/mass) in the product of 1% to 75%, such as 1% to 50%, 2% to 40%, 3% to 30%, 4% to 25% or 5% to 20%, each inclusive, such as at least 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75% or more. For example, the weight ratio (grams/grams) of periosteum to bone matrix (cancellous bone or cancellous bone/DBM) is greater than or is about 0.05:4, 0.05:3, 0.05:2, 0.05:1.5, 0.05:1, 0.1:4, 0.1:3, 0.1:2, 0.1:1.5, 0.2 to 4, 0.2:3, 0.2:2, 0.2:2, 0.2:1.5, 0.2:1, 0.3:4, 0.3:3, 0.3:2, 0.3:1.5, 0.3:1, 0.4:4, 0.4:3, 0.4:2, 0.4:1, 0.5:4, 0:5:3, 0.5:2, 0.5:1.5 0.5:1 or more. For example, the product can contain 0.1 g to 0.5 g, inclusive (5% to 20%, inclusive) periosteum and about 1 g to 2 g, inclusive, bone matrix (cancellous bone or cancellous bone/DBM).

In examples of BRP provided herein that are produced to contain DBM, the DBM is combined in the product so that it does not exceed 45% by weight of the cancellous bone. For example, the DBM component is combined as a weight percent of the cancellous bone of less than or about less than 45%, such as less than 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1% or less. Typically, the DBM component is combined as a weight percent of the cancellous bone of 1% to 45%, for example, 5% to 45%, 5% to 40%, 5% to 30%, 5% to 25%, 10% to 45%, 10% to 40%, 10% to 30%, 10% to 24%, 15% to 45%, such as generally 20% to 45%, 20% to 40%, 20% to 30%, 20% to 25%, 25% to 45%, 25% to 40%, 25% to 30%, 30% to 45%, 30% to 40% or 40% to 45%, each inclusive.

To prepare BRP, the cancellous bone fragments, periosteum and optionally DBM are mixed together. Mixing can be performed using any procedure that achieves preparation of a product having a homogenous or uniform consistency. Typically, the mixing method is sufficiently gentle so that the structural and physical properties of the prepared and processed components are not compromised. It also is understood that, as with all processing steps described herein, the mixing is performed under sterile conditions. For example, mixing can be performed using a sterile wand, sterile rod, sterile spatula or sterile spoon.

If the periosteum is provided from the long bone, no other wetting or other handling agents are required. In some cases, if necessary to achieve desired handling properties, an additional biocompatible component can be added that is able to adhere components of BRP to generate a uniform composition. The biocompatible component can be natural or synthetic. Exemplary of such biocompatible components include, but are not limited to, gelatin, Type I collagen, bone marrow aspirate, blood, platelet-rich plasma (PRP), fibrin glue, bone putty, poly caprolactone, poly ethylene glycol, alginates, chitosans or chondroitin sulfates. It is within the level of a skilled artisan to empirically determine the type and amount of additional biocompatible component, if any, to include in BRP to achieve desired handling properties, including the ability to shape, mold and pack the product. The particular handling properties can depend on the desired application.

The resulting BRP is a homogenous composition in which the periosteum pieces adhere to themselves and to the bone matrix component. Thus, BRP is a malleable and shapeable product, without loss or separation of bone components in BRP, to provide a product that is suitable for implantation and packing into bony voids. If desired, other excipients, carriers, agents or additives can be added to BRP so long as the product retains its malleability and shapeability without separation or loss of bone components in the product.

3. Sterilization and Preservation of Bone Repair Product (BRP)

Subsequent to preparation of BRP, BRP can be treated to sterilize or to reduce bioburden in the product. For example, sterilization procedures can include low dose irradiation, antibiotic washing and physical debridement. These methods attempt to reduce the antigenicity of the bone graft while providing sterilization. More extensive sterilization can be provided through gamma irradiation, electron beam irradiation, or ethylene oxide treatment. These measures, however, can cause a decrease in the mechanical and physical properties of the graft, including loss in cell viability. It is understood that the particular procedure is one that does not result in loss of osteoconductive, osteoinductive, osteogenic and angiogenic properties of BRP. Typically, sterilization methods include a method that can kill bacterial spores, which have been linked to deaths from allografts.

For example, bioburden reduction can be achieved using antibiotic washing. BRP can be treated with one or more antibiotics and/or one or more antimycotics in order to reduce the level of bioburden within the bone. Antibiotics that can be employed include, but are not limited to, gentamicin; vancomycin; penicillin; macrolide antibiotics, such as erythromycin; sulfa-based antibiotics and combinations thereof. Antimycotics that can be employed include, but are not limited to, amphotericin, fluconazole and combinations thereof. In methods of treatment using a liquid solution, BRP is treated in a manner that does not result in separation of bone fragments from periosteum. Generally, BRP is added to a low volume solution containing antibiotic(s) and/or antimyotic(s) just to cover or submerge the product. For example, BRP is added to the solution containing antibiotic(s) and/or antimyotic(s) to achieve a ratio of liquid solution that is up to 5 parts antibiotic solution to 1 part BRP (e.g. 5 mL to 1 mL), such as up to 4 parts, 3 parts or 2 parts antibiotic solution to 1 part BRP. The BRP can be treated with antibiotic(s) and/or antimyotic(s) for up to 4 days, and generally for up to 2 days or 48 hours. For example, BRP can be treated with antibiotic(s) and/or antimyotic(s) for from or from about 18 hours to 24 hours. The BRP can be gently rinsed with a physiologic solution, such as PBS or saline, to remove any unwanted antibiotic(s) and/or antimyotic(s). The rinse or wash steps can be repeated a plurality of times as desired.

After treatment, the bioburden level of BRP can be tested using standard procedures known in the art. Such procedures include those set forth in U.S. Pharmacopeia (USP) General Chapter <71>, "Sterility Testing" (*United States Pharmacopeia General Chapter <71>*, United States Pharmacopeial Convention: Rockville, MD, December 2012, 35$^{th}$ revision).

BRP can be stored at any appropriate temperature, depending on the particular application, the length of storage, the container used for storage and other factors that are within the level of a skilled artisan to empirically consider. If desired, prior to storage, BRP can be packaged in an article of manufacture, such as any described above in Section C. As discussed elsewhere herein, BRP or an article of manufacture or container containing BRP can be stored at room temperature or ambient temperature of 18° C. to 25° C., refrigerated conditions of 2° C. to 8° C., or under freezing conditions for cryopreservation, such as at temperatures of about or less than −20° C., such as generally −20° C. to −196° C., inclusive, for example −80±5° C. In particular examples of BRP provided herein, the cell viability is retained after storage, including after post-thaw from storage. For example, the cell viability of BRP after storage or post-thaw is at least 1%, 5%, 10%, 15%, 20%, 25%, 30%, 35%, 40%, 50%, 55%, 60%, 65%, 70%, 75%, 80%, 85%, 90%, 95% or more, and generally is at least 70%, 75%, 80%, 85%, 86%, 87%, 88%, 89%, 90%, 91%, 92%, 93%, 94%, 95%, 96%, 97%, 98%, 99% or more.

To store BRP, it typically undergoes a cryopreservation process. In the methods provided herein, the tissue is generally processed and BRP prepared for cryopreservation within 5 days of tissue collection. Cryopreservation is performed in any suitable manner that does not affect the structural properties of BRP, nor affect the osteoconduction, osteoinductive, osteogenic, or angiogenic activities of BRP.

For example, BRP can be added to an appropriate preservation medium, such as a cryopreservation or vitrification medium containing a suitable cryoprotectant. The cryoprotectant can contain dimethy sulfoxide (DMSO), glycerol, a glycol, a propylene glycol, an ethylene glycol, propanediol, polyethylene glycol (PEG), 1,2-propanediol (PROH) or a mixture thereof. In some examples, the cryopreservation solution can contain one or more non-cell permeating cryopreservative, including but not limited to, polyvinyl pyrrolidone, a hydroxyethyl starch, a polysaccharide, a monosaccharide, an alginate, trehalose, raffinose, dextran, human serum albumin, Ficoll, lipoproteins, polyvinyl pyrrolidone, hydroxyethyl starch, autologous plasma or a mixture thereof. A suitable cryopreservation solution contains a cryopreservative in an amount of at least about 0.001% to 100%, by volume, such as an amount from or from about 2% to about 20%, 5% to about 10% by volume, each inclusive, and generally at least 2%, at least 5%, at least 10% or more by volume. For example, the cryopreservative can be DMSO and the cryopreservation solution can contain DMSO at a concentration of at least 2% by volume, at least 5% by volume, at least 10% by volume or more. Further, the cryopreservation solution can contain serum albumin or other suitable proteins to stabilize the membrane during the freeze-thaw process and to reduce the damage to cells, thereby maintaining viability. Serum albumin can be human serum albumin or bovine serum albumin. In some examples, the cryopreservation solution can contain from or from about 1% to about 20% serum albumin or other suitable proteins, such as 1% to 10%, 1% to 5%, 5% to 20% or 5% to 10% serum albumin or other suitable proteins. In addition, the cryopreservation solution can contain a physiological solution, such as a physiological buffer or saline, for example phosphate buffered saline.

Generally, BRP is added to a low volume solution containing cryoprotectant just to cover or submerge the product. For example, BRP is added to a solution containing cryoprotectant to achieve a ratio of liquid solution that is up to 5 parts solution to 1 part BRP (e.g. 5 mL to 1 mL), such as up to 4 parts, 3 parts or 2 parts solution to 1 part BRP. The BRP can be incubated with cryoprotectant for at least 30 minutes, such as at least 60 minutes, before cryopreservation. Excess cryopreservation solution is removed, such as by decanting. The BRP remains saturated or coated with cryopreservation solution, but the level is minimal such that it is therapeutically or pharmaceutically acceptable. This ensures that, except for thawing the product, no additional materials, steps or washing are required for the product preparation prior to use. If desired, after thawing BRP as described below, BRP can be gently rinsed with a physiologic solution, such as PBS or saline, to remove any residual cryoprotectant solution. The rinse or wash steps can be repeated a plurality of times as desired.

The cryopreservation includes storage of BRP at temperatures as low as −196° C., and as high as −20° C. Typically, BRP is stored for cryopreservation at −80° C. 5°. The cryopreservation conditions are such that the osteogenic cells contained in BRP remain viable. If desired, prior to cryopreservation and storage, BRP can be packaged in an article of manufacture, such as any described above in Section C. The articles of manufacture containing cryopreserved BRP can be stored at temperatures of −20° C. to −196° C., such as temperature of about or up to −80° C.±5° prior to use.

Before use, BRP is thawed. BRP is considered sufficiently thawed when it is malleable and able to be shaped. Any procedure that is sufficient to thaw BRP can be used so long as, when thawed, BRP remains malleable and shapeable, such that bone fragments and periosteum are adhered together, bones are not separated or lost, and BRP retains its ability to mold into different shapes. For example, product can be thawed at ambient temperature (e.g. room temperature) or at a higher temperature up to or about up to 37±2° C. Typically, thaw is facilitated by submersion or placement of the article of manufacture containing BRP in a water bath, which results in a more quick thaw. The precise time and condition for thaw can be empirically determined by a skilled artisan. In some examples, BRP contained in an article of manufacture is thawed by placement of the article of manufacture in a 37±2° C. water bath for at least 8 minutes, such as from or from about 10 minutes to 15 minutes. After thaw, BRP is ready for use. The product can be held 2 hours, 2.5 hour, 3 hours or longer post-thaw at room temperature prior to implantation.

E. Method of Assessing Properties and Activities of Bone Repair Product (BRP)

The bone repair product (BRP) provided herein can be assessed for properties and activities related to its use as a bone healing product. The properties and activities can be related to biological activities, immunogenicity, cell viability, and other activities and properties of the product. In particular examples, assays can be used to assess one or more of the osteoconduction, osteoinductive, osteogenic and/or angiogenic properties of the BRP. The assays can be performed in vitro or in vivo. Exemplary assays to assess activities and properties of BRP include any described elsewhere herein, including in the Examples.

In particular examples, BRP can be assessed for its ability or activity to promote bone growth or remodeling. There are a variety of in vitro or in vivo assays/models that can be used to assess bone healing or regeneration of the bone repair product provided herein. Such assays are well known to a skilled artisan. Such assays can be performed in vitro, ex vivo or in vivo. For example, various assays are known to a skilled artisan for assessing the therapeutic activity to treat bone defects or other injuries or conditions. These include in vivo assays, such as various animal models, to assess the ability of BRP to induce or augment bone growth (see, ASTM Standard F2721, *Standard Guide for Pre-Clinical In Vivo Evaluation in Critical Size Segmental Bone Defects*. West Conshohocken, Pa., USA: ASTM International; 2008. www.astm.org.). Exemplary animal models include, for example, rat, rabbit, dog, goat and sheep models. In such examples, a bone defect is created using a tool of appropriate size acceptable for the model. For example, for rats, the defect is generally 5-10 mm in diameter, and can be larger in larger animals. In some cases, the defect can be fixed to secure the implant and reduce dislocation. For example, fixation can be achieved using a polyethylene/polacetal plate with K-wires/screws. Then, the bone repair product can be implanted into the bony void. As a control, an empty defect control can be used in which no bone defect has been made.

Outcome on bone growth and remodeling can be assessed using radiographic, histologic or mechanical analysis. For example, for histological analysis, standard stains such as hematoxylin/eosin, Toluidine Blue, or Modified Trichrome stain can be used to assess the quality of tissue and detection of calcified tissue. Computer Tomography (CT) also can be employed to monitor bone regeneration over time. In addition, mechanical tests of bone, such as 3- or 4-point bending or torsional strength testing can be employed.

Exemplary models for assessing bone growth and repair in animals models are known, such as for rats (Yasko et al. (1992) *Journal of Bone & Joint Surgery*, 74:659-670; Chen et al. (2002) *Journal of Orthopaedic Research*, 20:142-150; Oakes et al. (2003) *Clin Orthop Rel Res.*, 413:281-290; Tsuchida et al. (2003) *Journal of Orthopaedic Research*, 21:44-53); rabbit (Bostrom et al. (1996) *Clinical Orthopaedics & Related Research*, 327:272-282, Smith et al. (1995) *Journal of Controlled Release*, 36:183-195), Wheeler et al. (1998) *Journal of Biomedical Materials Research*, 43:365-373, Brekke et al. (1998) *Journal of Biomedical Materials Research* 43:380-398); canine (Bruder et al. (1998) *Journal of Bone and Joint Surgery-American*, 80-A:985-996, Cook et al. (1998) *Journal of Orthopaedic Trauma*, 12:407-412, Itoh et al. (1998) *J Vet Med Sci.*, 60:451-458), Sciadini et al. (2000) *Journal of Orthopaedic Research*, 18:289-302); goats (Buma et al. (2004) *Biomaterials*, 25:1487-1495, Dai et al. (2005) *Calcified Tissue International*, 77:55-61); sheep (Gao et al. (1997) *Arch Orthop Trauma Surg*, 116:290-294, Gugala et al. (1999) *Journal of Orthopaedic Trauma*, 13:187-195, Blokhuis et al. (2000) *Journal of Biomedical Materials Research*, 51:369-375, Petite et al. (2000) *Nature Biotechnology*, 18:959-963).

In another example, a mouse model can be employed. For example, a calvarial defect model can be employed (Spicer et al. (2012) *Nat. Protoc.*, 7:1918-1929). A standard procedure for this model involves creating a full-thickness calvarial defect (e.g. 4 mm in diameter) in the non-suture associated right parietal bone of CD-1 mice (wildtype or nude mice). For example, a diamond-coated trephine bit can be used to create the defect. Then, the bone repair product can be implanted into the bony void. The healing of the calvarial defect can be assessed using micro-computed tomography ($\mu$CT) at various times after implantation and grafting. In other examples, canine, rabbit or rat calvarial models can be used.

To assess immunogenicity, cells can be obtained from BRP and assessed for presence of immune cell markers present on hematopoietic or endothelial cells. For example, osteogenic cells do not express human leukocyte antigens (HLA Class II) or T-cell activation molecules (CD40, CD80, CD86). Without HLA antigens and the molecules that provoke T-cell activation, the osteogenic cells do not induce immune responses. Immunogenicity studies also can be performed using mixed lymphocyte reaction (MLR) assays on BRP.

F. Methods of Use of Bone Repair Product (BRP)

The bone repair product (BRP) can be used to promote bone growth and/or bone remodeling, including in the treatment of any of a variety of bone diseases, disorders, defects or injuries for which other bone grafts, including allografts or autografts, have been employed. Such diseases, disorders, defects or injuries are well known to a skilled artisan. The subject for treatment can be any animal subject that has a bone disease, disorder, defect or injury and is in need of treatment, including any mammal, such as a human or non-human primate. In particular examples, the subject is a human. BRP can be used to fill or partially fill bone voids and/or gaps of the skeletal system associated with the bone disease, disorder, defect or injury.

For example, BRP compositions provided herein can be used to correct bone defects in orthopedic, neurosurgical plastic or reconstructive surgery, in periodontal procedures, and in endodontic procedures. Such applications include, but are not limited to, induction of bone formation for hip replacement operations, knee replacement operations, foot and ankle surgeries (e.g. ankle fusion), spinal fusion procedures, repair of periodontal defects, treatment of osteoporosis, repair of bone tumor defects, dental procedures, repair of cranial maxilla facial defects and repair of bone fractures or defects. The bone disease, disorder, defect or injury can result from a developmental failure, or by degeneration or trauma, caused naturally or by surgery.

Non-limiting examples include repair of simple and compound fractures and non-unions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, tumor surgery, e.g. deficit filling, discectomy, laminectomy, excision of spinal cord tumors, anterial cervical and thoracic operations, repair of spinal injuries, scoliosis, lordosis and kyphosis treatment, intermaxillary fixation of fractures, mentoplasty, temporomandibular joint replacement, alveolar ridge augmentation and reconstruction, inlay bone grafts, implant placement and revision and sinus lifts.

For example, bone diseases, disorders, defects, or injuries that can be treated with BRP provided herein include, but are not limited to, degenerative disc disease, avascular osteonecrosis, osteosarcoma fractures, and fracture non-unions. BRP can also be employed in bone fusions, such as spine fusions, as well as disc augmentation, and for bone regeneration in orthopedic implants.

The BRP can be administered directly to the site of the bone disease, disorder, defect, or injury. In particular, BRP can be packed directly onto the site affected by the bone disease, disorder, defect, or injury. For example, BRP can be packed into bony voids. BRP has a sufficient consistency and shapeability such that it can easily fill or pack any a bone void. For example, BRP can be molded or formed into a desired shape generally conforming to the shape and size of the defect site, and then positioned or pressed, either manually and/or using instrumentation, into the defect site. It also has a consistency such that the BRP will be retained at the implantation site long enough for initial bone formation, osteoinductive signaling and host cell attachment to occur. Due to the handling properties of BRP, and its ability to be shaped or formed, no device or special material is required to use the product. If necessary, a cover can be applied over the product where it has been applied or packed into bone.

In some examples, BRP can be used in conjunction with devices employed in the treatment of bone diseases, defects, disorders and injuries, such as, for example, orthopedic cage devices, ceramics or plates that can be employed in the spine or in bones to promote bone growth and fusion. Furthermore BRP can be used in conjunction with an autologous bone graft. BRP also can be administered with antibiotic, antimyotics, or other anti-inflammatory agents. In some cases, BRP can be administered in combination with osteoinductive factors, such as BMP-2, BMP-7, and/or PDGF, or the patient's blood, PRP or bone marrow in order to enhance the osteogenic/osteoinductive potential of BRP.

G. Examples

The following examples are included for illustrative purposes only and are not intended to limit the scope of the invention.

Example 1

Evaluation of Methods for Obtaining and Processing Periosteum

Experiments were performed to assess if periosteum could be isolated and processed to retain the activity of angiogenic growth factors, which play an important role in bone repair. Properties of periosteum derived from different sources and different methods of processing periosteum were compared.

A. Comparing Source of Bone for Obtaining and Processing Periosteum

Periosteum was isolated from flat and long bone, and each evaluated for the difficulty of removal of periosteum, their ability to be cleaned from attached muscles and fat, and the physical properties of the resultant periosteum. For example, properties of periosteum, such as stickiness and ability to swell, are properties that would contribute to the handling of a bone repair product (BRP) containing periosteum mixed with other bone components.

To prepare periosteum, femurs (long bone) or iliac crest (flat bone) were collected from a human cadaver donor obtained from a tissue bank. The bones were cleaned of residual muscle and fat tissue, and periosteum was isolated by edging the bone with a scalpel and scraping along the vertical axis with a metal spatula or periosteal elevator, to remove the periosteum as a sheet. The periosteum was placed in a volume of physiological saline sufficient to cover the material in order to facilitate further removal of residual muscle and fat, and to observe swelling. To observe the stickiness of the material, the periosteum was minced using two scalpels by cutting the periosteum into small pieces to obtain a homogeneous appearance such that no large pieces remained.

A comparison of the properties of the periosteum isolated from long bone and flat bone is summarized in Table 3. The results show that the periosteum from the long bones could be efficiently isolated and cleaned of muscle and fat, was sticky after mincing and swelled when placed in saline. In contrast, the periosteum from flat bones did not swell and was more fibrous (i.e. not sticky). Also, there was very limited amount of periosteum available to be isolated from the flat bones relative to the long bone shafts. Finally, while periosteum could be isolated from the flat bone, it was more easily isolated from the long bone and cleaned from attached muscles and fat. Thus, the results show that the properties of the periosteum from the long bone are better for use in a BRP. For example, the stickiness ensures the periosteum pieces adhere to themselves and other bone components, thereby holding components together and providing a packable material with the appropriate handling properties. Thus, periosteum from long bone was selected for inclusion in the BRP.

TABLE 3

Long versus Flat Bone Periosteum Properties

| Properties | Source of Periosteum | |
| --- | --- | --- |
| | Long Bone | Flat Bone (i.e., iliac crest) |
| Able to be isolated | Yes | Yes |
| Able to be cleaned from attached muscles and fat | Yes | Poor |
| Stickiness after mincing | Yes, Sticky | No, Fibrous |
| Swells in Saline | Yes | No |

B. Assessing Methods to Mince the Periosteum

To compare procedures to mince the periosteum to generate a malleable consistency, methods of mechanical mincing were evaluated. The methods assessed were: the use of two scalpels, the use of an herb mincer (Zyliss, Crate and Barrel, Cat #525642) and the use of Polytron PT300 tissue homogenizer (Supplied by Kinematica). The methods were compared in order to identify the process that would 1) efficiently mince the periosteum into small pieces with a uniform consistency (e.g. a consistency that could fill a bone void), 2) minimize loss of the material, and 3) ensure that the material that was produced had a sufficiently sticky consistency that it could attach to other pieces of periosteum and the other components to be contained in BRP.

The results are set forth in Table 4. The results show that mincing with two scalpels generated relatively uniform size pieces and minimized periosteum loss. In addition, as described in Table 3, the minced periosteum was sticky. The other methods resulted in a loss of material and an inefficient mincing that did not result in a uniform consistency. Therefore, the use of two scalpels was selected for periosteum mincing.

TABLE 4

Comparison of Mincing Methods

| Method | Results |
| --- | --- |
| Two Scalpels | Periosteum was minced. Obtained uniform minced pieces of periosteum |
| Herb Mincer | Periosteum wrapped around blades and shaft, no mincing |
| Polytron PT300 | Periosteum clogged machine, no mincing; loss of material. |

C. Assessing Presence of Angiogenic Growth Factors in Periosteum

Periosteum processed as described above was assessed for the presence of angiogenic growth factors. Periosteum was isolated from femurs of a donor, processed by mincing using two scalpels as described above and stored at −80±5° C. for two weeks. The processed periosteum was thawed at room temperature until it became malleable. Thawed periosteum (0.3±0.1 g) was homogenized using a Qiagen TissueLyser (Qiagen, Cat. No. 85600). Tissue extracts were evaluated for the presence of VEGF and bFGF using an R&D Systems Duoset enzyme-linked immunosorbent assay (ELISA) kit according to the manufacturer's instructions (VEGF, Cat. No. DY293B; and bFGF, Cat. No. DY233, each obtained from R&D Systems, Minneapolis, MN). VEGF and bFGF were considered present if the absorbance value was above the lowest level of quantification in the kit. Furthermore, the lowest level of detection was determined to ensure reliability of detection (i.e. absorbance was at least 3 fold higher than the background absorbance). Due to high levels of bFGF in samples, a serial dilution was performed to ensure accurate quantification.

The results are set forth in Table 5. The results show that VEGF and bFGF were detected in the isolated and processed periosteum. As described in Example 9 below the precise amount of detected growth factors depends on the lysis method employed, such that it is possible that the concentration of angiogenic growth factor present in periosteum is higher than measured. The results show that the method of isolation and processing of periosteum, which include storage at −80±5° C. and thawing, maintained the presence of angiogenic factors VEGF and bFGF.

TABLE 5

Angiogenic Growth Factors in Periosteum

| Growth Factor | Amount in tissue lysate (pg/mL) | Amount adjusted for tissue weight (pg/mL/g tissue) |
| --- | --- | --- |
| VEGF | 76.97 | 256.58 |
| bFGF* | 3814.2 | 12712.49 |

*Average 4 serial dilutions

Example 2

Evaluation of Methods to Prepare Viable Cancellous Bone Chips

Cancellous bone contains bone extracellular matrix, osteoinductive growth factors, and viable bone matrix cells that contribute to bone repair. Methods of preparing cancellous bone for inclusion in a BRP were compared to identify a procedure that can generate bone fragments sufficient in size to fill a bony void, while also retaining viable endogenous bone cells.

Cancellous bone was isolated from long bones (femurs) of a human cadaver donor obtained from a tissue bank by removal of the articular cartilage using a band saw, reciprocating saw, sagittal saw, or hammer and osteotome. The isolated cancellous bone pieces were approximately 2 cm×2 cm in size and placed in saline until processing as described in subsections below. Pieces larger than 2×3 cm were found to hamper processing into bone chips (i.e., jam the blender blades). For bone that was visually identified as more dense bone, smaller bone fragments (approximately 1×1 cm) were used.

A. Assessing methods to Obtain Small Bone Fragments

Various methods were compared to prepare bone chips. Specifically, different equipment was assessed for preparing the bone chips, including: a coffee mill, a rotary cheese grater (Manufactured by Zyliss, Crate and Barrel, Cat. No. 527718), a hand cheese grater (Oxo Handheld Coarse Grater, Target, Cat. No. 14039343), a nut grinder (Progressive International Nut Chopper, Target, Cat. No. 12824755), an 8-speed blender (Manufactured by Oster, Bed Bath and Beyond, Model No. BCBG08-COO-NP0), and a 7-speed laboratory blender (Manufactured by Waring, Cat. No. 7012).

For the blenders, the cancellous bone was processed using the equipment in the presence of 250 mL Dulbecco's Phosphate buffered saline (dPBS). The presence of dPBS during the processing steps washes the bone and removes non-bone tissue cells, such as hematopoietic cells and some of the fat from the bone. For methods using the Oster Blender, the cancellous bone was blended on a combination of icebreaker, smoothie (low) and shake (low) setting for periods of 10-15 seconds. The icebreaker setting was used to initiate the blending in order to minimize any chance of jamming the blade, and then the speed was adjusted to smoothie or shaker setting. For processing using the 7-speed Waring Blender, the cancellous bone, in the presence of 250 mL of chilled dPBS, was blended on a combination of button 7 (22000 rpm) and button 4 (14500 rpm). The blending was initiated using button 7 and then immediately changed to button 4 for 10-15 seconds.

Cell viability was assessed using the LIVE/DEAD Viability/Cytotoxicity Kit (Manufactured by Molecular Probes, Cat. No. 03224). Staining was performed according to the manufacturer's instructions. Briefly, staining solution was prepared by adding 1 µL of Calcein-AM solution and 1 µL of ethidium bromide solution to 1 mL of bone in saline. Viable cells stained positive for calcein, which is taken up and retained within live cells, and produces a uniform green fluorescence (Ex/em~495 nm/~515 nm). Cells with damaged membranes (non-viable) take up Ethidium homodimer-1, which binds to nucleic acids, and produces red fluorescence (ex/em~495/~635 nm). Following incubation, pieces of bone were placed onto a slide and cells were visualized using a fluorescent microscope (Olympus IX70) with an attached camera. The samples were photographed and the presence of live cells (green staining) and dead cells (red staining) was assessed.

The results are summarized in Table 6. The results show that the 7-speed laboratory blender and 8-speed Oster blender effectively processed the bone chips. The coffee mill, rotary cheese grated, hand cheese grater, and nut grinder were unable to process the cancellous bone effectively. After processing, all methods produced viable cells, although processing of cancellous bone with a coffee mill produced visually fewer viable cells.

TABLE 6

Equipment Evaluated for Cancellous Bone Preparation

| Equipment | Viable Cells | Results |
| --- | --- | --- |
| Coffee Mill | Present, visually less green fluorescent cells. | Insufficient volume, unable to regulate speed. |
| Barrel Cheese Grater (coarse blade) | Present | Unable to process cancellous bone. Bone was harder than blade and bent barrel |
| Hand Cheese Grater | Present | Unable to process small pieces of cancellous bone, too much potential waste. |
| Nut Grinder | Present | Unable to process cancellous bone. Blades frequently jammed and/or bone stuck to blades. |
| 8-speed Oster Blender | Present | Cancellous bone was successfully processed into chips approximately 600 µm-2 mm, but blender jars cannot be autoclaved. |
| 7-Speed Laboratory Blender | Present | Cancellous bone was successfully processed into chips approximately 600 µm-2 mm. |

Thus, the results demonstrate that the use of a blender is the best method for processing cancellous bone to obtain bone chips that contain viable cells and are appropriate size for use in the product. No differences in presence of viable cells were observed between the two blender units. Once it was identified that the blenders effectively processed the cancellous bone chips, they were evaluated for their ability to be sterilized and feasibility of use in manufacturing. Ultimately, the 7-speed laboratory blender was selected for processing cancellous bone in BRP, because it effectively processed cancellous bone and the blender jars can be autoclaved to ensure sterility of BRP product.

B. Effect of Bone Chip Size on Cell Viability

To generate a product that is optimal for filling bony voids, bone chips ranging in size from 600 µm to approximately 2 mm in size were contemplated. Different sized bone chips are believed to have different osteoconductive activities (Gruskin et al. (2012) Advanced Drug Delivery Reviews, 64:1063-1077). To assess if different sized bone chips could be prepared by blending, while retaining viable bone matrix cells, bone chips were separated by size. Briefly, cancellous bone was processed using a 7-speed laboratory blender to produce heterogeneous sized bone chips. The bone chips were sequentially passed through certified 2 mm (US Standard #10) and 600 µm (US Standard #30) sieves and washed in saline. The presence of viable cells was assessed using a LIVE/DEAD Viability/Cytotoxicity kit as described above.

The results are detailed in Table 7. The results show that bone chips that are between 600 µm and 1.9 mm in size, and those that are greater than 2 mm in size contain viable cells when processed into bone chips using a blender, in the presence of chilled dPBS.

TABLE 7

Effect of Bone Chip Size on Cell Viability

| Sieve | Pore Size | Size of Separated Bone Chips | Viable Cells |
| --- | --- | --- | --- |
| US Standard #10 | 2 mm | Greater than 2 mm | Present |
| US Standard #30 | 600 µm | 600 µm to 1.99 mm | Present |

Example 3

Preparation of Bone Repair Product (BRP)

This example describes the preparation of a bone repair product (BRP) composed of cancellous bone chips containing viable cells, periosteum, and demineralized bone matrix (DBM). The BRP contains the processed periosteum and bone chips using procedures based on methods described in Examples 1 and 2. In addition to cancellous bone chips containing viable cells, bone chips were prepared so that the product contained demineralized bone matrix (DBM). Cancellous bone and DBM contain the osteoconductive matrix and osteoinductive growth factors. The inclusion of the periosteum provides additional matrix and growth factors that are required for bone healing and is an especially rich source of angiogenic factors necessary to support new blood vessel formation.

A. Tissue Collection and Processing

For preparation of BRP, long bones (i.e. femurs) were selected as a primary tissue source because they contain all components for inclusion in BRP, including the periosteum. Research grade donor knees-en-bloc or legs-en-bloc were received from human tissue banks after authorization for donation. The tissues were collected according to the recovering agency standard operating procedures.

To extract the periosteum, cancellous bone, and DBM, first, the surfaces of knees-en-bloc or legs-en-bloc were thoroughly wiped down with povidone iodine solution, using a sterile wiper. The knee joint was dissected to separate the femur, tibia and fibula with care to prevent damage to the cartilage surfaces or periosteum, and in order to preserve the integrity of the Bone-Tendon-Bone (BTB). The BTB assemblies were isolated from donor knees-en bloc or legs-in-bloc. Soft tissues, including adipose, muscle, fascia, ligaments and tendons, were removed to expose the articular cartilage surfaces on the tibial plateau, femoral condyles, the femur and tibial shafts and the knee joint.

To isolate BTB, the quadriceps tendons were cut approximately 5 mm above the joint. The patella and patellar ligament were reflected inferiorly, ensuring that the quadricep tendon, patella, patellar tendon, and tibial insertion remained intact. The medial and lateral collateral ligaments and anterior cruciate ligaments were cut. The femur was then separated from the tibia by removing any remaining soft tissue from around the joint space. The tibial plateau was then removed to isolate a BTB with the following specifications: the tibial bone block must be at least 30 mm long, from the tibial plateau, with a minimum margin of 2 mm distal to the patellar ligament. A cut was made at least 2 mm from the patellar tendons' insertion point on the medial and lateral sides of the tibia to maintain a width of at least 12 mm with a margin of 2 mm beyond the patellar ligament. A cut was then made a minimum of 11 mm from the edge of the tibia to ensure a constant depth of at least 11 mm and a square shaped block.

The long bones were further processed to isolate and prepare the periosteum, cancellous bone and DBM, as described below.

1. Preparation of Periosteum

Periosteum was isolated from the surface of bones for use in BRP. The periosteum did not contain any viable cells upon receipt of the tissue, since the cells die within 24 hours post-mortem. The lack of viable cells was confirmed by live/dead staining of the periosteum using procedures substantially the same as described above.

From the isolated periosteum, remaining soft tissue and fat were removed from the femoral and tibial shaft using forceps, scalpels, sterile wipes and/or tissue scissor. The bone was edged with a scalpel and then scraped using a periosteal elevator or metal spatula to cut the Sharpey fibers and dissociate the periosteum from the bone. The periosteum was removed and placed in sufficient saline to cover the tissue. Upon addition of chilled or room temperature saline, the periosteum tissue swelled and was allowed to swell for a minimum of 10 minutes or until it was further processed and combined with the cancellous bone and DBM. Notably, because the periosteum cannot "over swell," there was no upper time limit for incubation of the periosteum in the saline.

After the material had swelled, the periosteum was further cleaned of residual muscle and fat tissue using a finger, scalpel, scissors, and/or forceps. The cleaned periosteum was then minced using scalpels in a minimal amount of saline (approximately 10-50 mL) to generate a uniform, consistent blend with no large pieces, as described in Example 1. Periosteum was then centrifuged at 2000 rpm±200 rpm for approximately 2 minutes, at room temperature, and any remaining residual muscle was removed. Periosteum was then stored at 2-8° C. until it was combined with cancellous bone and DBM to form BRP.

2. Isolation and Processing of Cancellous Bone into Bone Chips

Cancellous bone was isolated from the long bone by removal of the articular cartilage by shaving it with reciprocating, sagittal saw, and/or osteotome. The isolated bone pieces were cut into approximately 2-3 cm sized pieces and placed in chilled saline until processing into bone chips. Isolated cancellous bone pieces were further processed into smaller bone chips ranging from 600 µm to 2 mm, which are the size for formulation of bony voids. As described in Example 2, to blend bone, a handful of cancellous bone pieces (typically 10-20) were added to the 7-speed Waring blender jar with approximately 250 mL of chilled dPBS. The blender was then started on button 7 and immediately switched to button 4 for 10-15 seconds.

The bone chips were then separated by size by sequentially passing through a 2 mm, 600 µm, and 125 µm sieve system. Any material collected in the 2 mm sieve was placed back in the blender with another handful of bone pieces. This process was repeated until all bone pieces were processed into pieces between 125 µm and 2 mm. The final bone chips were separated into groups of between 600 µm-2 mm and between 125 µm-599 µm in size. The bone chips of 125 µm-599 µm in size were processed further as described below in Example 3.A.3.

The bone chips of 600 µm-2 mm were further processed to obtain cancellous bone containing viable osteogenic cells. Not all 600 µm to 2 mm bone chips were separated into independent bone chips; therefore, processed material retained by the 2 mm sieve after a minimum of two processes with the blender was also included for further processing. The subset of cancellous bone material that was trapped by the 2 mm sieve appeared to be a collection of smaller bone chips that were connected by residual connective tissue. Their handling properties were similar to that of BRP and since larger fragments also contained viable cells (see Example 2), this material was also included in BRP. To ensure a uniform appearance, bone pieces that looked like small pebbles, looked like pieces of cortical bone, or had red flecks were not included in BRP. In addition to separating bone chips by relative size, the use of the sieve, combined with the blending in dPBS, facilitated the removal of residual blood and some of the fat from the bone.

The fat was not, however, entirely removed by washing the bone chips in the sieves. To remove residual fat and any other non-bone materials, the collected bone chips >600 μm in size were transferred to centrifuge tube (50 mL, 175 mL, or 250 mL maximal tube volume depending on volume of bone chips). The tube was then filled with saline to the maximal volume and centrifuged at approximately 1500-2000±200 rpm for 2-5 minutes at room temperature to pellet the bone chips and separate out the fat, which floats to the top of the solution. After centrifugation, the supernatant containing the fat was decanted. Any residual fat that remained attached to the side of the centrifuge tube after decanting was removed by using a sterile wiper to wipe the inner wall of the centrifuge tube. This process was repeated (typically 1-3 times), as necessary, until the layer of residual fat, after centrifugation, was minimal or could be easily decanted. The aim was to remove visible, residual fat from the bone chips, although small amounts of fat can remain associated with the bone. Residual small amounts of fat are gradually removed from bone chips during the later processing steps, which includes treatment with Antibiotic Cocktail Solution-D, saline wash, and cryopreservation solution (see below).

After separation by size and fat removal, the cancellous bone chips between 600 μm and 1.99 mm were held at 2-8° C. in a physiological solution until they were combined with other components of BRP.

3. Preparation of Demineralized Bone Matrix (DBM)

To increase bioavailability of matrix proteins and growth factors, small bone chips were demineralized to produce demineralized bone matrix (DBM) for inclusion in BRP. DBM is bone from which the inorganic components (i.e., minerals) are removed, leaving the organic components (i.e., collagen and growth factors).

As described above, the processing of cancellous bone with the blender also produced bone chips ranging in size from 125 μm to 599 μm, which were bone chips captured in a 125 μm (US Standard #120) sieve from the flow through of the 600 μm sieve. The smaller bone chips ranging in size from 125 μm to 599 μm were collected, washed in saline, and centrifuged at 2000 rpm±200 rpm for approximately 2 minutes at room temperature, as necessary, to clean the bone. These steps were repeated until a prominent fat layer was no longer observed, although some fat typically remains associated with the bone. Cancellous bone chips were pretreated with enough 3% hydrogen peroxide to completely submerge the bone chips. Bone chips were incubated in the hydrogen peroxide for 5 minutes or until bubbles stop forming (whichever was shorter) at room temperature with gentle agitation. Bone chips were washed in saline to remove the hydrogen peroxide.

Alternatively, cortical bone fragments were pretreated with enough 3% hydrogen peroxide to completely submerge the bone fragments for 5-15 minutes. The bone fragments were washed in saline and then processed to 4 mm or smaller chips with a Retch ZM 200 Ultra Centrifugal Mill. The mill was operated at 18,000 rpm and bone chips were passed sequentially through a 10 mm and 4 mm sieve.

Demineralization was performed using an HCl treatment regimen of 0.5N HCl for 70 minutes±10 minutes at 2-8° C. (see Pietrzak et al. 2011 *Cell Tissue Bank*, 12:81-88; and Castro-Cesefia et al. 2011 Materials Science and Engineering, 31:523-530). Briefly, washed bone chips were added to 0.5N HCl (4.1 mL concentrated HCl (12N) added to 95.9 mL WFI distilled, deionized water per 100 ml of solution). The composition was incubated at 2-8° C. for 70 minutes±10 minutes. The effective ratio of bone to acid was at least 1 part bone to 10 parts acid.

Next, the 0.5N HCl solution was decanted from the bone chips and the bone chips were washed in 5 mM Sodium Phosphate (SP) Buffer (2.5 mL 1M SP in 497.5 mL of dPBS) to neutralize residual HCl on the bone. The DBM was then subjected to a second wash in saline. DBM was held at 2-8° C. until it was combined with viable cancellous bone and periosteum to form BRP.

To confirm that the DBM produced by this procedure was sufficiently demineralized to conform to the American Associate of Tissue Banks (AATB) requirements of less than 8% residual calcium, lots of DBM were sent for testing to determine residual calcium level by atomic absorption spectroscopy after acid digestion (WuXi Apptec, test code 400434). The maximum calcium level detected from four lots of cancellous bone was 1.09% (average 0.74±0.28 from 4 samples) and from three lots cortical bone was 5.4% (average 4.33±0.93 from 3 samples), which is below the 8% maximum allowed by AATB standards (AATB E.520).

B. Combining Processed Components to Form Bone Repair Product

The goal of the combined components was to achieve desired handling properties (Example 4), increased number of viable cells per cc (Example 6) and retain growth factors, including vascular growth factors for support of angiogenesis (Example 9). The prepared cancellous bone, periosteum, and DBM were combined according to the following procedures to form a malleable, shapeable, and functional product. First, the three components were weighed individually to calculate the total weight of the product. Then the three components were combined with the DBM not exceeding 45% of the cancellous bone by weight and mixed with a sterile spoon until the consistency was uniform. If the periosteum was too sticky, it was further minced with scalpel blades to generate a uniform consistency BRP. The fibrous and sticky nature of the periosteum combined with the smaller bone chips (approximately 125 μm to 2 mm) allowed the bone chips to easily adhere to each other. This property ensured that the resulting BRP was packable and shapeable, which are desired handling properties for the product for bone repair applications.

As described below in Example 6, this combination provided a malleable and packable product and a high (greater than 250,000 cells per cc) number of viable cells.

C. Bioburden Testing and Treating of Bone Repair Product

The BRP was added to an antibiotic cocktail containing a mixture of gentamicin sulfate (50 μg/mL) (Fresenius Kabi, Cat No. 17302), vancomycin hydrochloride (50 μg/mL) (Hospira Cat No. 4332-01), and amphotericin B (2.5 pg/mL) (Sigma-Aldrich, Cat No. A2942-20ML) (Antibiotic Cocktail Solution D). BRP was added to the Antibiotic Cocktail Solution D at 1 part BRP (1 g BRP=1 mL of antibiotic solution) to 2 parts antibiotic solution and incubated for 18 to 84 hours at 37° C., 5% $CO_2$. The incubation can proceed out to 96 hours, and tissue is typically processed and cryopreserved within 5 days from tissue collection. As shown in Example 13 below, the treatment of BRP with the antibiotic solution did not affect cell viability or growth factor level in the product.

To validate bioburden reduction, BRP was prepared from a donor as described above and was stored in saline, but without antibiotic treatment. The sample was tested for the level of disinfection of Antibiotic Cocktail Solution D by WuXi AppTec (Atlanta, Georgia). In brief, BRP samples were inoculated with 0.01 mL of approximately $1\times10^6$ CFU of each of the following organisms: *Bacillus atrophaeus, E. coli, Staphylococcus epidermidis, Enterococcus faecalis, Candida albicans, Bacteroides fragilis* in triplicate. After 15 minutes incubation at 2-8° C., a volume of 10 mL Antibiotic Solution D was added to each tube and incubated for 18, 24, or 28 hours. After the incubation period, the antibiotic was neutralized and each sample was counted utilizing membrane filtration to determine the number of colonies. The log reduction was calculated by subtracting the post-disinfection $\log_{10}$ from the pre-disinfection $\log_{10}$. This testing set the maximum initial bioburden levels criteria for incoming tissue used for BRP processing. This is based on the log reduction rates attained for Antibiotic Cocktail Solution D on the final bulk. The results for the allowable level in pre-antibiotic bioburden are shown in Table 8. BRP passed antibiotic validation requirements.

TABLE 8

BRP Pre-antibiotic Bioburden Levels

| Microorganism Category | Incoming Bioburden Limit |
|---|---|
| Aerobic | <100 CFU |
| Anaerobic | <100 CFU |
| Yeast and Mold | <5 CFU |
| Spore Former | <10 CFU |

To confirm the sterility testing result was not caused by a false negative result, bacteriostasis/fungistasis (B/F) testing also was performed on BRP to assess the presence of substances that would inhibit bacterial or fungal growth in a sterility test. Testing was performed on sterility test sample treated for 96 hours in Antibiotic Cocktail Solution D. Testing was performed by WuXi AppTec by inoculating ≤2.5 mL of test sample in ≥300 mL of soybean-casein digest (SCD) or fluid thioglycollate (FTM) medium with low levels of selected microorganisms according to criteria set forth in the U.S. Pharmacopeia (USP) General Chapter <71>, "Sterility Testing" (*United States Pharmacopeia General Chapter* <71>, United States Pharmacopeial Convention: Rockville, MD, December 2012, 35$^{th}$ revision). The SCD cultures were incubated for ≤5 days at 20-25° C. and the FTM cultures were incubated for ≤5 days at 30-35° C. The cultures were then compared visually to a positive to control for growth. If the levels of growth were comparable or greater than positive control, then the material was not considered to have bacteriostatic or fungistatic characteristics. The BRP passed the validation criteria and is not bacteriostatic or fungistatic.

D. Freezing and Packaging of Bone Repair Product

After antibiotic treatment, BRP was rinsed twice in saline and 5% Cryoserv® (Mylan Teoranta, Cat. No. 67457-178-50)/95% saline solution was added at a ratio of about 1 part BRP (1 g BRP=1 mL of volume for determination) to 2 parts cryopreservation solution. BRP covered in cryoprotectant solution was allowed to incubate for 60 minutes at 2-8° C. After 60 minutes, the excess cryopreservation solution was decanted, but BRP remained submerged in the cryopreservation solution. As shown in Example 14 below, the varying treatment length of BRP with the cryopreservation solution did not affect cell viability in the product.

Multi-well tissue culture plates were used to approximate BRP volume for purposes of preparing aliquots of the product for cryopreservation. After portioning BRP product into product units, BRP product was removed from the plate in a manner to maintain the ball shape of the product formed by packing in the well. The "ball-shaped" product was transferred into a 15 mL straight sided jar (ThermoFisher, Cat. No. 2116-0015) using a sterile spatula. BRP was chosen to be packed as a round ball for packing in the 15 mL straight sided jar, instead of shaped flat, since a "ball-shaped" product is easier to remove from the jar. After placing BRP into the 15 mL straight sided jar, the lid was tightened using a Torque Wrench to 22 to 31 lbs., which is the manufacture's recommended pressure for this container. After tightening, the jar was sealed in a 4×7 inch mangar pouch (Mangar Industries, Cat. No. FP0008427) to ensure sterility. BRP was placed at −80±5° C. in a Styrofoam container for a minimum of 12 hours, then transferred to −80±5° C. freezer.

Example 4

Assessing Packability and Shapeability of Bone Repair Product

The BRP was assessed to determine if altering the amount of the periosteum, relative to cancellous bone and DBM, in the product could affect the handling properties of BRP. BRP was prepared as described in Example 3, except the product was prepared containing a ratio of cancellous bone/DBM to periosteum of about 20:1 (5% periosteum), about 6.67:1 (15% periosteum) or about 5:1 (about 20% periosteum). As a control, a product containing cancellous bone and DBM, but not periosteum, also was prepared. The resulting samples were evaluated blindly and independently by three analysts for shapeability, which was defined as the ability for the material to hold together without any loss of bone chips and to mold into different shapes.

The results are set forth in Table 9. The results show that control samples, composed of cancellous bone and DBM, but lacking periosteum, were not shapeable. In contrast, there was no difference in the shapeability of the product containing different amounts of periosteium relative to cancellous bone/DBM. Thus, the results confirm that a combination of periosteum, cancellous bone, and DBM is necessary to provide a shapeable product, and that even a product containing only 5% periosteum is sufficient to produce a shapeable product.

TABLE 9

Shapability of Samples Containing Different Amounts of Periosteum

| | Sample Composition | | | Shapability test results by analysts | | |
|---|---|---|---|---|---|---|
| Sample | Cancellous/ DBM (g) | Periosteum (g) | Periosteum (%) | #1 | #2 | #3 |
| Control | 2 | 0 | 0 | No | No | No |
| 1 | 2 | 0.1 | 5 | Yes | Yes | Yes |
| 2 | 1.1 | 0.2 | 15 | Yes | Yes | Yes |
| 3 | 1.5 | 0.4 | 21** | Yes | Yes | Yes |

**Represents 20% periosteum

Example 5

Evaluating Thawing Time of Bone Repair Product Under Different Conditions

Exposure to warm temperatures and freeze-thaw cycles can significantly impact cell viability. Different thawing conditions were assessed for their impact on the handling properties of BRP and on cell viability.

A. Assessing Thaw Time on Product Malleability

BRP was prepared and cryopreserved as detailed in Example 3. Jars of 5 cc units of BRP, cryopreserved and stored at −80±5° C., were evaluated for the time required to thaw, which was defined as the time for BRP to become malleable. Briefly, 5 mL of BRP was removed from −80±5° C. storage and thawed by placement of the sealed jar: 1) on a bench at room temperature, 2) in a bowl containing room temperature water or saline to a level just below the jar lid, 3) in a 37±2° C. water bath, or 4) by adding room temperature saline to the jar containing BRP until it covered BRP (fast thaw). Starting at 5 minutes, BRP was checked every 5 minutes for malleability. Once the product was able to be shaped, it was considered thawed and ready to use.

The results are set forth in Table 10. The results show that the product is sufficiently thawed to result in a malleable product after a minimum of 15 minutes in room temperature saline, 30 minutes on a bench at room temperature, or 8 minutes in a 37±2° C. water bath. Also, adding room temperature saline directly to the product thaws the product quickly, but caused the bone chips to separate from the periosteum and each other.

TABLE 10

Evaluation of BRP Thaw Time

| Evaluation Time Points (in Min) | Thawing Condition | | | |
|---|---|---|---|---|
| | Room Temperature on a bench | in Room Temperature Saline Bath | in 37° Water Bath | submerged in Room Temperature Saline "Fast Thaw" |
| 5 | Frozen | Frozen | Frozen | thawed, not malleable |
| 10 | Frozen | Edges thawed, free from jar | Thawed | thawed, not malleable |
| 15 | Frozen | Thawed | Thawed | thawed, not malleable |
| 20 | Frozen | Thawed | Thawed | thawed, not malleable |
| 25 | Edges thawed, free from jar | Thawed | Thawed | thawed, not malleable |
| 30 | Thawed | Thawed | Thawed | thawed, not malleable |

B. Assessing the Effect of BRP Thawing Conditions on Cell Viability

1. Effect of Thaw Method on Cell Viability at Room Temperature

BRP was prepared and cryopreserved as detailed in Example 3. Jars containing 5 cc units of BRP were removed from −80±5° C. storage and thawed by placement of the sealed jar: 1) in a bowl containing room temperature saline for 20 minutes; 2) in a 37±2° C. water bath for 8 minutes, or 3) by adding room temperature saline to the jar containing BRP until it covered BRP (fast thaw).

After thawing, cell viability was assessed on samples by trypan blue staining. About 2.5 cc of a 5 cc BRP (half of the material in the jar) was utilized for cell viability testing. To prepare samples for trypan blue staining, after thawing, BRP was first washed with Dulbecco's Modified Eagle Medium (DMEM). Next, 3 mg/mL of Worthington Type 2 collagenase was added to the BRP (2 mL of collagenase per 1 mL of BRP) to gently digest the tissue and BRP was incubated at 37±2° C. with 5% $CO_2$ for 90 to 120 minutes on a rocker. After collagenase treatment, BRP was removed from the 37° C. incubator, and passed through a 70 μm cell strainer. The digested tissue was rinsed in DMEM to further release cells and decanted through the same cell strainer for a final volume of 45 mL of strained solution. The cell solution was pelleted by centrifugation (1800±200 rpm for 10±5 minutes), and the cell pellet was resuspended in DMEM in the same starting volume as the starting material, typically in 1-5 mL DMEM. The cell suspension was then diluted 1:2 in 0.4% trypan blue (Sigma, Cat. No. T8154) and cells were loaded onto a hemacytometer to count the total numbers of live and dead cells and calculate percent viability, using an inverted microscope. Bone cells were identified by their irregular shape and dark spot in the middle. Four large squares from one chamber were counted, then the number of cells per mL were calculated according to the following formula:

the number of cells per mL=((number of cells)/4)× $2×10^4$

The results are set forth in Table 11. The results demonstrate that cell viability was not compromised by the cryopreservation or any of the thaw procedures. Nevertheless, since the "fast thaw" procedure does not yield a malleable product when thawed as discussed above, the fast thaw procedure is not recommended for thawing BRP.

TABLE 11

Effect of Thaw Method on BRP Cell Number and Viability

| Thaw Method | Cell Count and Viability | | | | |
|---|---|---|---|---|---|
| | Live | Dead | Total | Cells/cc | % Viability |
| Room Temperature Bath | 88 | 5 | 93 | $4.4 \times 10^5$ | 94.62% |
| 37° C. Bath Thaw | 80 | 4 | 84 | $4.0 \times 10^5$ | 95.24% |
| "Fast Thaw" | 76 | 4 | 80 | $3.8 \times 10^5$ | 95.00% |

2. Post-Thaw Time Course of Cell Viability

The cell viability was assessed over time after thaw of jars containing 1 cc or 5 cc units of BRP in: 1) room temperature saline (RT Saline) for 20 minutes, or 2) the 37±2° C. water bath for 8 minutes (37° C. bath). Two 5 cc units or four 1 cc units were used for each thaw condition. After the initial thaw, units were kept on a bench at room temperature and cell viability was evaluated at 0 (baseline thaw), 1, 2 and 3 hour time points post-thaw. Cell viability was assessed by trypan blue staining as described above.

Table 12 sets forth the results of post-thaw cell viability of 5 cc samples and Table 13 sets forth the results of post-thaw cell viability of 1 cc samples. Cell viability of ≥70% was used as an acceptance criterion. The cell viability of BRP was not impacted by the thaw method, since cell viability was greater than 86% in all conditions tested. Because cell viability was 70% or greater through the three hours post-thaw at room temperature, the results show that BRP is stable for up to 3 hours or more post-thaw at room temperature.

TABLE 12

5 cc BRP Post-Thaw Stability Results

| Post-Thaw Evaluation time point (hr) | Thaw Method | Cell Count and Viability | | | | |
|---|---|---|---|---|---|---|
| | | Live | Dead | Total | Cells/cc | % Viability |
| Baseline, 0 | RT Saline | 88 | 5 | 93 | $4.4 \times 10^5$ | 94.62% |
| | 37° C. Bath | 80 | 4 | 84 | $4.0 \times 10^5$ | 95.24% |
| 1 | RT Saline | 107 | 9 | 116 | $5.4 \times 10^5$ | 92.24% |
| | 37° C. Bath | 96 | 6 | 102 | $4.8 \times 10^5$ | 94.12% |
| 2 | RT Saline | 85 | 6 | 91 | $4.25 \times 10^5$ | 93.41% |
| | 37° C. Bath | 71 | 4 | 75 | $3.6 \times 10^5$ | 94.67% |
| 3 | RT Saline | 57 | 9 | 66 | $2.8 \times 10^5$ | 86.36% |
| | 37° C. Bath | 65 | 4 | 69 | $3.3 \times 10^5$ | 94.20% |

TABLE 13

1 cc BRP Post-Thaw Stability Results

| Post-Thaw Evaluation time point (hr) | Thaw Method | Cell Count and Viability | | | | |
|---|---|---|---|---|---|---|
| | | Live | Dead | Total | Cells/cc | % Viability |
| Baseline, 0 | RT Saline | 71 | 6 | 77 | $3.6 \times 10^5$ | 92% |
| | 37° C. Bath | 63 | 4 | 67 | $3.2 \times 10^5$ | 94% |
| 1 | RT Saline | 81 | 4 | 76 | $3.6 \times 10^5$ | 95% |
| | 37° C. Bath | 89 | 6 | 85 | $4.0 \times 10^5$ | 93% |
| 2 | RT Saline | 85 | 6 | 81 | $3.8 \times 10^5$ | 93% |
| | 37° C. Bath | 62 | 5 | 67 | $3.1 \times 10^5$ | 93% |
| 3 | RT Saline | 59 | 7 | 68 | $3.0 \times 10^5$ | 87% |
| | 37° C. Bath | 56 | 7 | 63 | $2.8 \times 10^5$ | 89% |

For subsequent characterization experiments described below, BRP was routinely thawed by placing a jar containing BRP in a 37±2° C. water bath for 10-15 minutes. BRP was malleable and shapeable, and characterized as thawed, after 8 minutes.

Example 6

Comparison of Cell Viability of Bone Repair Product Preparations

The viability of cells in preparations of BRP prepared from different donors was quantitatively compared using trypan blue staining. Since cells in BRP are embedded within the bone extracellular matrix, enzymatic treatment with collagenase was required to release cells from the matrix before staining with trypan blue to determine cell number and viability as described above in Example 5. To confirm that the collagenase treatment itself was not affecting viability or cell number, viability and cell number was compared after treatment with collagenase for 1 or 2 hours.

Briefly, cryopreserved units of BRP prepared from different donors were thawed in a 37±2° C. water bath for 10-15 minutes. As set forth in Table 14, either 2-5 cc of BRP product was washed by addition of DMEM, and then 3 mg/mL collagenase was added to the preparation as described in Example 5. BRP was incubated with collagenase at 37±2° C. with 5% $CO_2$ for 1 or 2 hours (±15 minutes). After collagenase treatment, cells were isolated as described above in Example 5 and the cell suspension resuspended in 2-5 mL of DMEM so that the starting volume did not influence the results and the ratio between starting product and collagenase was maintained. Cells were diluted 1:2 in 0.4% trypan blue and viability determined as described in Example 5.

The results are set forth in Table 14. The results show that incubation with collagenase for 2 hours results in continued cell release, such that a greater number of cells were isolated from the bone chips after enzymatic treatment with collagenase for 2 hours compared to 1 hour. Further, incubation with collagenase for 2 hours did not compromise cell viability. In all samples tested, the viability was greater than 94%, which is far greater than the minimal of 70% cell viability used as an acceptance criterion for BRP. The results also show some variability in the number of cells isolated from the different donors.

On average, BRP from a sampling of the research donors contains on average 600,000 viable cells per cc with 94.7±1.2% cell viability (n=3). Similar experiments were performed to assess the cells per cc in BRP prepared from clinical grade donors. From a sample size of 65 clinical grade donors, the results showed an average cell number of 1,811,815±785,492 cells/cc with a range of 792,000 cell/cc to 4,320,000 cells/cc present in BRP.

TABLE 14

Evaluation of Cell Number and Viability for BRP Lots

| Donor # | Collagenase Digestion Time | Volume of BRP (cc) | Cell Count and Viability | | |
|---|---|---|---|---|---|
| | | | Total Cell Number | Cell Number/cc | % Viability |
| 66 | 1 hr. | 5 | 9.40E+05 | 188000 | 95.80% |
| 67 | 1 hr. | 5 | 1.07E+06 | 214000 | 94.50% |
| 68 | 2 hr. | 3 | 8.48E+06 | 2826667 | 95.30% |
| 69 | 2 hr. | 5 | 1.43E+07 | 2860000 | 96.10% |
| 69 | 1 hr. | 2 | 2.06E+06 | 1030000 | 96.00% |
| 69 | 2 hr. | 2 | 8.65E+06 | 4325000 | 95.20% |
| 70 | 2 hr. | 2 | 1.14E+06 | 570000 | 96.60% |

Example 7

Assessing Cell Types of Bone Repair Product

The cellular composition of the viable cells present in BRP was characterized via fluorescence activated cell sorting (FACS) using cell surface markers specific for various cell types. Staining for CD105 and CD166 were used to detect mesenchymal stem cells (MSCs; Pittenger and Martin 2004, Circ. Res., 95:9-20), tissue nonspecific alkaline phosphatase (TNAP) was used to detect osteogenic cells (Kim et al. 2012 Stem Cells Dev., 21:2958-2968), CD45 was used to detect hematopoietic cells (Koretzky 1993 FASEB J., 7:420-426; Taylor and Bank, 1988 Cryobiology, 25:1-17) and CD31 was used to detect endothelial cells (Suarez et al. 2007, J. Immunol., 179:7488-7496).

FACS analysis to assess BRP cell surface markers was performed on cells that were isolated from BRP using collagenase treatment as described in Example 5. The collagenase-extracted cells were immediately processed for FACS analysis. Briefly, the cells were incubated in FACS buffer (dPBS+5% BSA and 0.001% sodium azide) with antibodies to CD105 (Invitrogen, Cat. No. MHCD10504), CD166 (BD Biosciences, Cat. No. 559263), TNAP (Santa Cruz, Cat. No. SC-81754), CD45 (BD Biosciences, Cat. No. 555483), CD31 (BD Biosciences, Cat. No. 560983) or isotype control (BD Biosciences, Cat. No. 559320). The cells were then fixed with 1% Paraformaldehyde (1 mL of 4% paraformaldahyde and 3 mL of DPBS) and labeled with 7-Aminoactinomycin D (7-AAD) staining solution (Supplied by BD Biosciences, Cat. No. 559925) according to the manufacturer's instructions. FACS was performed utilizing single-color analysis on a FACSCalibur System (Manufactured by Becton-Dickinson) and analyzed using CELLQuest Software.

The results are summarized in Table 15. When analyzed by FACS, using a variety of cell-type-specific markers, BRP was shown to have a cellular profile consistent with MSCs and osteogenic cells. Immunogenic CD45 (hematopoietic) and CD31 (endothelial)-positive cells were not detected in BRP cells.

TABLE 15

Cell Composition of BRP

| Cell Marker | FACS Results | Marker Specificity |
|---|---|---|
| CD105 | Present | MSC |
| CD155 | Present | MSC |

TABLE 15-continued

Cell Composition of BRP

| Cell Marker | FACS Results | Marker Specificity |
|---|---|---|
| TNAP | Present | Osteogenic Cells |
| CD45 | Absent | Hematopoietic |
| CD31 | Absent | Endothelial |

Example 8

Assessing Properties of Bone Cells in Culture

To confirm the viability of cells in BRP and the presence of osteogenic cells in bone chips, cells from BRP were isolated and cultured. BRP, prepared as described in Example 3, was removed from storage at −80° C. and was thawed in a 37±2° C. water bath for 10-15 minutes. Thawed BRP was then washed in DMEM and incubated in a 3 mg/mL collagenase solution (Worthington Type II) for either 60 minutes (when bone chips were plated) or 120 minutes (when released cells were plated) on a rocker at 37±2° C. The collagenase solution was decanted over a 70 µm cell strainer, digested tissue rinsed in DMEM and decanted through the same cell strainer, and the resulting cell solution centrifuged as described in Example 5. Bone chips or isolated cells were obtained.

A. Culture of Collagenase Isolated Cells

The cell pellet, obtained from samples collected and treated after 120 minutes of collagenase treatment, was resuspended in 20 mL DMEM and cells were seeded in two T75 flasks and cultured at 37±2° C. and 5% $CO_2$. Cells were assessed for their ability to adhere and proliferate. The results show that cells were seen adhering and expanding from the plated cell pellets after 4 days. Proliferation and viability was observed for up to two weeks in culture.

B. Culture of Collagenase-Treated Bone Chips

Bone chips, collected and treated after 60 minutes of collagenase treatment, were washed and seeded into 6 well plates, and cultured at 37±2° C. and 5% $CO_2$. Cells were assessed for their ability to migrate. Visual assessment of cells in culture showed that cells migrated from bone chips and were able to proliferate in culture.

The cultured BRP bone chips also were assessed for the presence of osteogenic cells using the BCIP/NBT Alkaline Phosphatase Color Development Kit (Vector Technologies, Cat. No. SK-5400) to detect the presence of alkaline phosphatase positive (i.e. osteogenic) cells. The combination of NBT (nitro-blue tetrazolium chloride) and BCIP (5-bromo-4-chloro-3'-indolyphosphate p-toluidine salt) substrates yields an intense, insoluble black-purple precipitate when reacted with alkaline phosphatase. Alkaline Phosphatase is a marker for osteoblasts, and cells that stained positive for Alkaline Phosphatase are characterized as osteogenic cells.

After the cells were allowed to grow out from the bone chips, cells were labeled for the presence of alkaline phosphatase using BCIP/NTB substrate according to the manufacturer's instructions. Briefly, after culture for 10 days, bone chips and cells were fixed in 10% formalin stained for alkaline phosphatase for 30 minutes at 37° C., and washed. Cells were assessed visually for a purple color. The results showed that cells were alkaline phosphatase positive, and confirm the presence of osteogenic cells in BRP.

Example 9

Analysis of Growth Factors in Bone Repair Product

BRP prepared as described in Example 3 was assessed for the presence of various growth factors, including vascular endothelial growth factor (VEGF), basic fibroblast growth factor (bFGF), insulin-like growth factor-1 (IGF-1), transforming growth factor-β1 (TGF-β1), bone morphogenetic proteins 2 and 7 (BMP-2, BMP-7) and platelet-derived growth factor-BB (PDGF-BB).

BRP from different donors, prepared as described in Example 3, was thawed for 10-15 minutes in a 37±2° C. water bath, and then rinsed with PBS. The sample was weighed on a pan balance and about 0.3 g to 0.5 g (e.g. 0.4 g±1 g) of measured mass material used to prepare samples to assess the presence of growth factors.

To assess VEGF, bFGF, IGF-1 and TGF-β1, the measured mass of BRP was snap frozen in a homogenization tube in liquid nitrogen. Once the samples were pre-cooled, for at least 5 minutes on dry ice, a 5 mm steel bead was added to each tube and samples were homogenized using a Qiagen Tissue Lyser (Qiagen, Cat. No. 85600) in 1 mL of PBS, according to the manufacturer's instructions.

To assess BMP-2, BMP-7, and PDGF, BRP material was first demineralized in 0.5N HCl for 70±10 minutes at 2-8° C. The HCl was decanted and the demineralized bone was neutralized with 20 mL of 0.5% Sodium Phosphate Buffer (in PBS). The demineralized material was then washed twice in saline and was incubated in 4M Guanadine Hydrochloride (GuHCl) (Pierce, Cat. No. 24115) for 14-18 hours at 2-8° C., while rotating. Samples treated with GuHCl were processed using a Zeba Spin Desalting Column (Pierce, Cat. No. 89891) to exchange the GuHCl for PBS, prior to use.

BRP tissue extracts were analyzed using an antibody sandwich enzyme-linked immunosorbent assay (ELISA) using commercially available DuoSet ELISA Development Kit or Quantikine ELISA kit (Manufactured by R&D Systems) to quantitatively assess the presence of growth factors in the components of BRP. Homogenates for all assays were spun down at 18,000±1000 rpm for 10±2 minutes using a microcentrifuge. Supernatants were collected and analyzed for specific growth factors via ELISA using either R&D System Duoset (VEGF, Cat. No. DY293; bFGF, Cat. No. DY233; IGF-1, Cat. No. DY291; PDGF-BB, Cat. No. DY220) or Quantikine kit (TGF-β1, Cat. No. DB100B; BMP-7, Cat. No. DBP700; BMP-2, Cat. No. DBP200) according to the manufacturer's instructions, as described below.

A. Vascular Endothelial Growth Factor (VEGF)

1. Assessing Levels of VEGF

For measuring VEGF in samples, either 0.3 g or 0.5 g BRP material was lysed in 1 ml PBS, and prepared as detailed above. VEGF was measured using the VEGF R&D Quantikine ELISA kit (Cat. No. DY293) according to manufacturer's instructions. Briefly, BRP lysates were diluted 1:2 prior to the assay (1 part lysate to 1 part Qiagen calibrator diluent, RD6U) per the manufacturer's recommendation. BRP lysates were added to wells of a 96-well plate pre-coated with anti-VEGF antibody and incubated for 2 hours at room temperature. Standards were diluted according to the manufacturer instructions and also added to wells.

After washing, 100 µl of VEGF conjugate (detection antibody) was added to each well and the plates were incubated for 2 hours at room temperature. The wells were washed twice, and then 100 µl of Substrate Solution was added to each well and the plates were incubated at room temperature for 20 minutes. The reaction was stopped after the addition of 50 µl of Stop Solution. The optical density at 450 nm was measured using a microplate reader. VEGF levels (pg/ml) were determined by comparing the optical density of samples to known standards. Experimental values were considered valid if they were above the lower level of detection (i.e. 3 fold greater than the background absorbance). The results are set forth in Table 16. The results show that VEGF is present in BRP. Further experiments performed on BRP prepared from 58 clinical grade donors showed an average VEGF level of 209±72 pg/mL from 0.4 g±0.1 g of tissue in PBS.

TABLE 16

VEGF Levels in BRP

| Sample | Amount of BRP tissue used for extraction (g) | VEGF levels pg/mL | Std Dev | pg/mL/gram Tissue |
|---|---|---|---|---|
| 66 | 0.3 | 236.85 | 17.17 | 789.50 |
| 66 | 0.5 | 282.08 | 31.25 | 564.17 |
| 68 | 0.3 | 250.81 | 2.48 | 836.02 |
| 68 | 0.5 | 309.70 | 11.15 | 619.39 |

2. Assessing Accuracy of Quantitation

In order to determine the accuracy of VEGF quantitation in tested tissue extracts, the percent of VEGF recovered from samples spiked with 125 pg/mL of VEGF standard was assessed. Specifically, tissue extract samples were prepared as described above, and each sample divided into two. To one of the samples, 125 pg/mL of VEGF was added. Then the samples (not spiked or spiked with 125 pg/mL VEGF) were added to wells of a 96-well plate, and VEGF was measured in samples using the ELISA assay described above. VEGF levels (pg/mL) were determined by comparing the optical density of samples to known standards. Percent recovery was calculated using the following formula:

Percent Recovery=1−[(Experimental Value of "Spiked" Sample−Expected Value)/Expected Value]

The expected value was calculated by adding 125 pg/mL to the pg/mL of the "not spiked" sample. The results are set forth in Table 17. The results show that there was a greater than 80% recovery of VEGF in the "spiked" sample, which indicates that VEGF is present in BRP and can be accurately quantified.

TABLE 17

VEGF Spike Recovery from BRP Tissue Extracts

| Sample | Amount of BRP tissue used for extraction (g) | VEGF levels pg/mL | pg/mL + 125 pg/ml VEGF | % Recovery |
|---|---|---|---|---|
| 66 | 0.3 | 118.43 | 237.28 | 92.00 |
| 66 | 0.5 | 141.04 | 256.00 | 88.50 |
| 68 | 0.3 | 125.40 | 258.83 | 91.60 |
| 68 | 0.5 | 154.85 | 204.71 | 98.50 |

3. Comparison of Lysis Methods on Quantified Growth Factor

Reports indicate that the lysis methods used to extract proteins can vary quantification of growth factors in bone allograft (Wildemann et al. (2007) *Cell Tissue Banking*, 8:107-114). To assess if there was a difference in quantified levels of VEGF using different lysis methods, lysis using either phosphate buffered saline (PBS) or Guanidine HCl (GuHCl) was employed. Briefly, BRP samples were processed as described above using a Qiagen Tissue Lyser, except that homogenization was performed either in the presence of PBS or 4M GuHCl. VEGF was detected in samples using the ELISA assay described above.

The results are set forth in Table 18. The results show that the levels of quantified VEGF are approximately 5-fold higher when GuHCl was employed in the lysis buffer. Table 19 depicts the levels of VEGF in BRP prepared from various donors when GuHCl is used as lysis buffer.

TABLE 18

Lysis of BRP with PBS v. Guanidine HCl

| Lysis Buffer | VEGF (pg/mL) | Std. Dev. |
|---|---|---|
| PBS | 111.7 | 6.2 |
| GuHCl | 550.5 | 43.3 |

TABLE 19

VEGF in BRP of Multiple Donors Lysed with Guanidine HCl

| Donor | VEGF (pg/mL) |
|---|---|
| 80 | 550.5 |
| 81 | 519.9 |
| 82 | 697.4 |
| Avg. | 589.3 |
| Std Dev. | 94.9 |

B. Other Growth Factors

For measuring bFGF and IGF-1 in samples, 0.4±0.1 g BRP material was lysed in 1 ml PBS, and prepared as detailed above. For measuring TGF-β1 in samples, 0.4±0.1 g BRP material was lysed in 1 ml GuHCl, and prepared as detailed above. For measuring PDGF, BMP-2, and BMP-7 in samples, 0.4±0.1 g demineralized BRP material was lysed in 1 ml GuHCl, and prepared as detailed above. PDGF, bFGF, and IGF-1 were tested using a DualSet ELISA kit, see above, according to manufacture instructions. Briefly, 100 µl of BRP lysates were added to wells of a 96-well plate coated with detection antibody. Standards were diluted according to the manufacturer and also added to wells.

After washing, 100 µl of detection antibody was added to each well and the plates were incubated for 2 hours at room temperature. The wells were washed twice, and then incubated for 20 minutes at room temperature with a Streptavidin-HRP conjugated secondary antibody. 100 µl of Substrate Solution was then added to each well and the plates were incubated at room temperature for 20 minutes. The reaction was stopped after the addition of 50 µl of Stop Solution. The optical density at 450 nm was measured using a microplate reader. Growth factor levels (pg/ml) were determined by comparing the optical density of samples to known standards.

TGF-β1, BMP-2, and BMP-7 were tested using a Quantikine ELISA kit, see above, according to manufacture instructions. Briefly, BRP lysates were diluted 1:2 prior to the assay (1 part lysate to 1 part Qiagen calibrator dilutent, RD6U) per the manufacturer's recommendation. BRP lysates were added to wells of a 96-well plates pre-coated with anti-growth factor antibody and incubated for 2 hours at room temperature. Standards were diluted according to the manufacturer and also added to wells.

After washing, 100 μl of conjugate (detection antibody) was added to each well and the plates were incubated for 2 hours at room temperature. The wells were washed twice, and then 100 μl of Substrate Solution was added to each well and the plates were incubated at room temperature for 20 minutes. The reaction was stopped after the addition of 50 μl of Stop Solution. The optical density at 450 nm was measured using a microplate reader.

Experimental values were considered valid if they were above the lower level of detection (i.e. 3 fold greater than the background absorbance). The results are set forth in Table 20, and are corrected for the amount of starting tissue. The results show that angiogenic and osteogenic growth factors are present in BRP.

TABLE 20

Angiogenic and Osteogenic Growth Factor Levels in BRP

| Growth Factor | pg/mL/g tissue | SEM |
|---|---|---|
| bFGF | 221.4 | 132.5 |
| PDGF | 147.4 | 5.04 |
| IGF-1 | 2822.0 | 1000.6 |
| BMP-2 | 1040.3 | 379.7 |
| BMP-7 | 1512.6 | 576.2 |
| TGF-β1 | 415.3 | 121.5 |

C. Comparison of Growth Factor Levels in Bone Repair Product Versus Viable Bone Allografts The presence of angiogenic growth factors VEGF, bFGF, and PDGF in tissue extracts of BRP was compared to the amount of the growth factors in viable bone allograft control extracts. The viable bone allograft control was prepared in the same manner as BRP, except it lacks periosteum. It is composed of viable cancellous bone and DBM. Tissue extracts of BRP and viable bone allograft control were prepared from the same donor and in the identical process, as described above.

Tissue extracts were analyzed for the levels of angiogenic growth factors using commercially available ELISA kits as described above. The results are set forth in Table 21. The quantification results show that the levels of growth factors VEGF, bFGF, and PDGF-BB as assessed by ELISA (n=3) are on average, 2-, 4- and 5-fold, respectively, more in tissue extracts from BRP than from viable bone allograft.

TABLE 21

Percentage of Angiogenic Growth Factors in BRP Relative to Viable Bone Allograft Control

| Growth Factor | Viable Bone Allograft Control | BRP |
|---|---|---|
| VEGF | 100 | 170.5 |
| bFGF | 100 | 405.8 |
| PDGF | 100 | 508.3 |
| IGF-1 | 100 | 241.0 |

Example 10

Assessing Osteoinductive, Osteoconductive, and Osteogenic Activity of the Bone Repair Product The osteoinductive and osteoconductive properties of BRP product were determined by assessing the ability of extracts of BRP to induce cell migration or cell attachment of human mesenchymal stem cells (MSCs). Expanded human bone marrow-derived MSCs were fluorescently labeled with Calcein-AM (1:1000 dilution). In the assays, BRP extracts were prepared as described in Example 9, except the lysates were prepared in DMEM and tested for activity. As a control, extracts of viable bone allograft, prepared in an identical manner as BRP except without periosteum, also were prepared. DMEM medium containing either 10% or 20% fetal bovine serum (FBS) was used as a positive control for the presence of growth factors (assay dependent) and DMEM alone was used as a negative control.

A. Assessing MSC Migration In Vitro

Both growth factors and ECM, which are present in BRP, have been shown to be involved in recruiting cells (e.g. osteoblasts and osteoprogenitor cells, endothelial cells and fibroblasts and mesenchymal stem cells (MSCs)) to the site of injury (Albreksson et al. 2001 Euro Spine J., 10:S96-S101). To test the ability of BRP to recruit cells, an in vitro transwell experimental model was utilized. 50,000 MSCs in DMEM were placed in 8 μm PET membrane transwell in a 24-well plate (BD (Corning) FluoroBlok™, Cat. No. 351152). Medium containing DMEM supplemented with either: 1) BRP extracts, 2) viable bone allograft extract, 3) 20% FBS (positive control) or 4) no supplement (negative control), was added to the lower compartment of the transwell plate. The assay was maintained at 37±2° C. and 5% $CO_2$ for 18-24 hours. The cells were then fluorescently labeled by immersion of the transwells in a 0.1% Calcein AM solution for 20 min. at 37° C. The transwells were then washed in PBS and imaged using a fluorescent microscope.

The number of cells that migrated to the underside of the insert's porous membrane, and toward the supplemented medium, or control medium, was evaluated microscopically. The results showed that BRP extract promoted migration of MSCs. The magnitude of the effect of BRP was similar to the FBS positive control, and was approximately 5-10 fold higher than extracts from the viable bone allograft control. Therefore, BRP extracts have the ability to recruit MSCs, which evidences that BRP is osteoinductive.

B. Assessing MSC Attachment In Vitro

Osteoconductivity of BRP matrix was assessed by evaluating MSC attachment in vitro. For this experiment, 0.4 g of thawed cryopreserved BRP and 1 mL of DMEM was added to a well of a 12-well cell culture plate after it had been blocked with 1% BSA for 1 hour. The BRP was submerged in DMEM and placed at 37° C. in 5% $CO_2$ overnight. The next day 100,000 human MSCs, fluorescently labeled with 0.1% Calcein-AM, in DMEM were added to each well. BRP was returned to 37° C., 5% $CO_2$ for 1 hour. The material was then washed twice with dPBS to remove non-adherent cells. The presence of attached cells was determined by fluorescent microscopy. The results showed that MSCs attached to BRP. The retention of MSC on BRP matrix after washing demonstrates that BRP can act as an osteoconductive matrix.

C. Assessing MSC Differentiation In Vitro

Once MSCs and osteoprogenitor cells have been recruited to an injury site and attached, the microenvironment and osteogenic growth factors trigger differentiation of these cells into osteoblasts. To demonstrate the ability of BRP to induce MSC differentiation, 6000 MSCs were cultured in a 24-well plate for seven days in DMEM with 10% FBS without osteoinductive growth factors (negative control), in DMEM with 10% FBS media supplemented with 10 mM β-glycerol 2-phosphate, 50 μM L-ascorbic acid 2-phospate, and 100 nM dexamethasone (positive control containing osteogenic growth factors), or DMEM supplemented with BRP lysate. The MSCs were cultured for seven days at 37±2° C. and 5% $CO_2$.

After culture, culture monolayers were fixed in 10% formalin and stained with BCIP/NBT Alkaline Phosphatase Substrate according to the manufacturer's instructions as described in Example 8. Osteogenic cells were identified as purple or alkaline phosphatase positive. The results showed that a low level background signal was detected in cells treated without growth factors (negative control). In contrast, the numbers and extent of purple stain was increased in cells treated with BRP extract or positive control complete growth medium. The extent of purple signal was similar between cells treated with BRP extract or positive control, indicating that BRP extract induced differentiation at levels similar to those with the positive control osteoinduction medium. Therefore, medium supplemented with BRP extract induced differentiation of MSCs into osteoblasts and BRP supplies functional osteogenic growth factors that induce MSC differentiation.

Example 11

Evaluation of Bone Repair Product to Induce Blood Vessel Formation

To assess if BRP can induce angiogenesis, an endothelial cell tube formation assay was performed. The endothelial cell tube formation assay evaluates the formation of 3-dimensional tube structures by endothelial cells and is a specific demonstration of angiogenesis (Auerbach et al. 2003 Clin. Chem., 49:32-40).

Ninety six-well plates were coated with 75 µL Matrigel® (BD (Corning), Cat. No. 356231), and allowed to gel for 1 hour at 37±2° C. Human umbilical vein endothelial cells (HUVEC) were used as the source of endothelial cells in the assay. BRP extract or allograft control extract was prepared as described in Example 9, except EBM-2 medium (Lonza, Cat. No. cc-3156) was used to prepare extracts. Human umbilical vein endothelial cells (HUVEC) (Lonza, Cat. No. C2517A) were resuspended to a density of $1 \times 10^5$ cells/mL in either basal media (EBM-2, negative control), BRP extract in EBM-2, allograft control extract in EBM-2, or EBM-2 complete growth medium. 10,000 cells were seeded on a basement membrane extract, Matrigel®. The plate was incubated for 4-6 hours at 37±2° C. and 5% $CO_2$.

After incubation, to visualize tube formation in the assay, HUVEC cells were labeled with the cell-permeable dye calcein AM by adding the dye a 0.3% solution of the dye in EMB-2 to each well for a final concentration of 0.1%. The plate was incubated at 30 minutes at 37±2° C. and 5% $CO_2$. The assay was then visually assessed using a fluorescent microscope.

The results showed that after 4-6 hours BRP supplemented medium induced vessel formation similar to that seen in complete growth medium (positive control), while viable bone allograft control supplemented medium had a negligible effect in this assay. Likewise, no tube formation was seen in the negative control. Therefore, the results indicate that the addition of BRP led to an increase in tube formation, which is an assay for angiogenesis. The higher amounts of angiogenic growth factors in BRP, as detailed in Example 9, and the ability to induce tube formation supports that BRP has angiogenic properties.

Example 12

Assessing Immunogenicity of Bone Repair Product

The immunogenicity of allograft tissues is mediated by macrophages and its presence can be detected by stimulating the allograft with bacterial lipopolysaccharide (LPS) and monitoring TNF-α release. Data from published reports correlate TNF-α levels of less than 100 pg/mL to an absence of significant immune response, in a variety of experimental systems (Wang et al. 2002, Transplantation, 74:772-778; Ohashi et al. 2010, Clinical Immunology, 134:345-353; Toungouz et al. 1993 Human Immunology, 38:221-225). To assess whether BRP is immunogenic, an in vitro assay was conducted to test for the presence of macrophages by LPS-induced TNF-α generation.

BRP, prepared as described in Example 3, was thawed in a 37±2° C. water bath for 10-15 minutes and cultured in DMEM+5% fetal bovine serum. As a control, unprocessed product containing a bone plug without articular cartilage was obtained as described in Example 2, and also was similarly processed and cultured in DMEM+5% fetal bovine serum. The cultured samples were exposed to 1 µg/mL bacterial LPS (Sigma-Aldrich) for 24±1 hour at 37±2° C. and 5% $CO_2$. Following incubation with LPS, tissue culture supernatants were collected and tested for the presence of TNF-α via ELISA using a Quantikine kit (Supplied by R&D Systems, Cat. No. DTA00C). Human Peripheral Blood Mononuclear Cells (hPBMCs), which are known to secrete high levels of TNF-α upon LPS stimulation, were used as a positive control in the assay. Additionally, BRP that was not treated with LPS was included as a baseline control in the analysis.

The results are set forth in Table 22. The positive control hPBMCs were strongly induced by the addition of LPS, and expressed TNF-α at approximately 1800 pg/ml. The unprocessed starting material control (n=2) responded to stimulation with LPS by production of TNF-α, to a level that exceeded 100 pg/mL, thereby demonstrating that the unprocessed control product contains immunogenic material. Conversely, TNF-α levels in BRP were below limits of detection of the ELISA assay. Therefore, the final BRP was not responsive to LPS stimulation, and thus does not contain immunogenic cells as assessed by TNF-α generation.

TABLE 22

| LPS induced TNF-α in BRP | | |
|---|---|---|
| Material | TNF-α (pg/mL) with LPS | TNF-α (pg/mL) without LPS |
| Raw Material | 126.1 | 11.42 |
| BRP | 6.1 | 6.24 |
| PBMCs | 1405.6 | 52.05 |

Example 13

Evaluation of Antibiotic Treatment on Cell Viability and Growth Factors in Bone Repair Product Antibiotic Cocktail Solution-D is the antibiotic solution used in BRP as described in Example 3. To ensure that it was appropriate for use in BRP, its affect on cell viability and growth factor level was examined.

A. Assessment of Antibiotic Treatment on Cell Viability

BRP was prepared as detailed in Example 3, except that BRP was treated with Antibiotic Cocktail Solution-D at a 1:2 ratio (1 gram of BRP to 2 mL) of antibiotic) at 37±2° C. and 5% $CO_2$ for 0, 24, 48, 72, 96 hours. Then, antibiotic treated BRP was tested for cell viability using Live/Dead Staining essentially as described in Example 2 by adding 1 µL of Calcein-AM solution and 1 µL of ethidium bromide solution to 1 mL saline and incubating BRP in staining solution. Alternatively, Trypan Blue Staining was performed on a collagenase-extracted cell suspension as described, in Example 5. The results showed that cell viability was maintained in all antibiotic treatment incubation times tested. There was no change in cell viability observed after different lengths of treatment with antibiotic.

B. Assessment of Antibiotic Treatment on Presence of Growth Factors

The retention of growth factors after treatment of BRP with antibiotics was evaluated. A BRP preparation was generated as described in Example 3, except that BRP was treated with Antibiotic Cocktail Solution-D at a 1:2 ratio (1 gram of BRP to 2 mL of antibiotic) at 37±2° C. and 5% $CO_2$ for 24 hours or 96 hours. BRP tissue extracts were prepared, and VEGF levels in extract samples determined substantially as described in Example 9. Three different lysate preparations from each antibiotic treatment were assessed.

The results are set forth in Table 23. The results depict the mean VEGF level (pg/mL), the standard deviation (St. Dev.), and the coefficient of variation (the ratio of the standard deviation to the mean). The results showed that there was no difference in VEGF levels between the 24 hour and 96 hour treatment with Antibiotic Cocktail Solution-D.

TABLE 23

Comparison of VEGF Levels after 24 and 96 Hour Antibiotic Treatment

| Antibiotic Treatment (hours) | VEGF Levels (pg/ml/gram tissue) | | | % of 24 Hours |
|---|---|---|---|---|
| | Mean | St. Dev. | % CV | |
| 24 | 304 | 29.6 | 9.73 | 100 |
| 96 | 317 | 38.8 | 12.2 | 104 |

Example 14

Effect of Cryopreservation Solution Composition and Incubation Time on Cell Viability of Bone Repair Product Experiments were performed to assess different cryopreservation conditions that preserve cell viability, but with a minimal amount of cryopreservation solution, so that BRP is ready to use upon thaw without additional wash steps or preparation. Cryopreservation conditions were evaluated on BRP prepared as described in Example 3, except that different cryopreservation conditions were employed.

A. Cryopreservation Solution Composition

Cryopreservation solutions containing various percentages of Cryoserv® (DMSO), (Mylan Teoranta, Cat. No. 67457-178-50), and with varying amount of Human Serum Albumin (HSA) (Octapharma, Cat. No. 67467-0643-01), PlasmaLyte-A (Baxter Healthcare Corporation, Cat. No. 2B2544), or saline were assessed as summarized in Table 24. To evaluate different cryopreservation solution compositions, BRP product samples were incubated in the cryopreservation solution for 60 minutes at 2-8° C. at a minimal ratio of 1 part BRP (by weight) to 2 parts cryopreservation solution (by volume). For example, for each 100 g of BRP material, 200 mL of cryopreservation solution was required. After 60 minutes, the excess cryopreservation solution was decanted, but BRP remained submerged in the cryopreservation solution. The cryopreservation solution coated BRP was placed in a freezing container; either a conical tube or 15 mL straight sided jar, and then in a room temperature Styrofoam box. The Styrofoam box containing samples of BRP in tubes or jars was transferred to −80±5° C. for cryopreservation. Placing of samples into the Styrofoam box allowed slow cooling and cryopreservation of samples (see below). Samples were thawed after 24 or 96 hours in −80±5° C. and cell viability was assessed using a live/dead staining kit as described in Example 2 and 13.

Table 24 summarizes the different cryopreservation solutions tested and the cell viability results. All tested samples contained viable cells, such that all cryopreservation solutions are suitable for cryopreservation of the product. To confirm cell viability, a collagenase-extracted cell suspension was prepared from BRP that was cryopreserved with 5% Cryoserv/95% Saline using procedures substantially as described in Example 5, and cells stained using trypan blue. Using trypan blue staining, there was an average 93% cell viability in this sample. Therefore a cryopreservation solution of 5% Cryosery (DMSO) in 95% saline is sufficient as a cryopreservation solution for BRP.

TABLE 24

Effect of Cryopreservation Solution Composition on BRP Cell Viability

| Sample | Cryopreservation Solution Composition | | | | Presence of Viable Cells |
|---|---|---|---|---|---|
| | Cryoserv [DMSO] (percent) | HSA (percent) | PlasmaLyte-A (percent) | Saline (percent) | |
| Control (fresh) | N/A | N/A | N/A | N/A | Yes |
| 1 | 5 | 10 | 85 | N/A | Yes |
| 2 | 5 | 5 | 90 | N/A | Yes |
| 3 | 5 | 2.5 | 92.5 | N/A | Yes |
| 4 | 5 | 0 | 95 | N/A | Yes |
| 5 | 5 | 0 | N/A | 95 | Yes |

B. Cryopreservation Solution Immersion Time

To assess the minimum time by which BRP can be incubated with cryopreservation solution, and maintain cell viability, BRP was immersed in cryopreservation solution for various lengths of time. 1 cc and 5 cc BRP samples prepared as described in Example 3, but prior to treatment with cryopreservation solution, were used to evaluate cryopreservation immersion time. A time of 60 minutes immersion time was used as a baseline control, since this time was already determined to maintain cell viability as demonstrated above in Table 24.

Briefly, 1 cc or 5 cc samples were measured and aliquoted into 15 mL straight sided jars as described in Example 3. The samples were incubated at a ratio of 1 part bone (by weight) to 2 parts cryopreservation solution (by volume) for either 30, 45, or 60 minutes at 2-8° C. After incubation, the samples were placed in a styrofoam box for controlled freezing to −80° C. After 12 days, samples were thawed in a 37±2° C. water bath for 10-15 minutes and tested for cell viability by trypan blue staining as described in Example 5.

The results are set forth in Table 25. The results show that cell viability was maintained well above the acceptance criterion of ≥70% for all conditions. The cell viability of multiple donors never dropped below 85% when pre-incubated for 30, 45, or 60 minutes in cryopreservation solution at 2-8° C. Thus, the results show that an incubation time as low as 30 minutes in cryopreservation solution is sufficient to maintain approximately the same percent cell viability as a 60 minutes incubation.

TABLE 25

Effect of Cryopreservation Solution Tissue Immersion Length at 2-8° C. on BRP Cell Viability

| Tissue immersion time in Cryopreservation Solution at 2-8° C. (minutes) | Size of Sample (cc) | Donor # | Cells/ml | Percentage of 60 minute cell number (relative to same tissue volume (cc)) | Percent Viability |
|---|---|---|---|---|---|
| 30 | 1 | 79 | $2.9 \times 10^5$ | 104% | 95 |
| 30 | 5 | 79 | $2.85 \times 10^5$ | 92% | 92 |
| 30 | 5 | 76 | $4.05 \times 10^5$ | 98.80% | 87 |
| 45 | 1 | 79 | $2.9 \times 10^5$ | 104% | 98 |
| 45 | 5 | 79 | $2.7 \times 10^5$ | 87% | 93 |
| 60 | 1 | 79 | $2.8 \times 10^5$ | 100% | 97 |
| 60 | 5 | 79 | $3.1 \times 10^5$ | 100% | 94 |
| 60 | 5 | 76 | $4.05 \times 10^5$ | 100% | 95.2 |

C. Cryopreservation Method (Slow, Solution Decanted, Styrofoam)

The impact of the temperature of the Styrofoam box, which were used to temporarily house the jars of BRP, was evaluated by assessing viability of the cells. BRP was prepared substantially as described in Example 3, except samples of BRP were cryopreserved down after identical treatments in either a room temperature or a pre-chilled to −80±5° C. Styrofoam box. The samples were then stored at −80° C.±5° C. for 12 days. After storage, samples were thawed in a 37±2° C. water bath for 10-15 minutes and tested for cell viability by trypan blue staining as described in Example 5.

The results are set forth in Table 26. Cell viability was at or above 90% for material pre-incubated in a room temperature or in a pre-chilled at −80±5° C. Styrofoam box, when assessed by trypan blue exclusion. Thus, Styrofoam boxes at room temperature or pre-chilled to −80±5° C. can be used for cryopreservation of BRP.

TABLE 26

Effect of Styrofoam Box Temperature on BRP Cell Viability

| Sample/Box Temperature | Viable Cell Count | Dead Cell Count | Cells/ml | Percent Viability |
|---|---|---|---|---|
| Room Temperature #1 | 108 | 12 | $5.4 \times 10^5$ | 90 |
| Room Temperature #2 | 86 | 128 | $4.3 \times 10^5$ | 90.5 |
| −80° C. #1 | 60 | 2 | $3.0 \times 10^5$ | 96.8 |
| −80° C. #2 | 84 | 6 | $4.2 \times 10^5$ | 93.3 |
| −80° C. #3 | 80 | 5 | $4.0 \times 10^5$ | 94.1 |

Since modifications will be apparent to those of skill in this art, it is intended that this invention be limited only by the scope of the appended claims.

What is claimed is:

1. A method of repairing a bone defect, the method comprising administering to the site of the bone defect a bone repair composition comprising:
    (a) cancellous bone chips comprising viable cells, wherein the cancellous bone chips are not processed with a loosening agent,
    (b) 5-20 wt. % devitalized and non-immunogenic periosteum pieces, based on the total weight of the composition, and
    (c) demineralized bone matrix (DBM) chips, wherein one or more growth factors comprised in the composition promote angiogenesis at the site of the bone defect.

2. The method of claim 1, wherein the cancellous bone chips are from long bone.

3. The method of claim 2, wherein the long bone is femur and tibia.

4. The method of claim 1, wherein the cancellous bone chips are less than 4 mm in size.

5. The method of claim 4, wherein the cancellous bone chips are from about 125 µm to 4 mm or from about 125 µm to 3 mm in size.

6. The method of claim 1, wherein the periosteum pieces are from long bone.

7. The method of claim 1, wherein the periosteum pieces adhere to themselves and to the bone chips.

8. The method of claim 1, wherein the DBM chips are from cortical bone.

9. The method of claim 1, wherein the viable cells are osteogenic cells.

10. The method of claim 9, wherein the osteogenic cells comprise one or more of mesenchymal stem cells, osteoprogenitor cells, osteoblasts, or osteocytes.

11. The method of claim 1, wherein the one or more growth factors are angiogenic growth factors.

12. The method of claim 1, wherein the one or more growth factors are osteogenic growth factors.

13. The method of claim 1, wherein the one or more growth factors comprise vascular endothelial growth factor (VEGF), platelet-derived growth factor (PDGF), platelet-derived growth factor-BB (PDGF-BB), basic fibroblast growth factor (bFGF), insulin-like growth factor-I and -II (IGF-I and IGF-II), transforming growth factor-beta (TGF-β), bone morphogenetic protein (BMP), or parathyroid hormone (PTH).

14. The method of claim 13, wherein the transforming growth factor-beta is TGF-β1.

15. The method of claim 13, wherein the bone morphogenetic protein is BMP-2, BMP-4, BMP-6, BMP-7, or BMP-9.

16. The method of claim 1, wherein the composition is sterilized.

17. The method of claim 16, wherein the composition is sterilized by gamma irradiation, electron beam irradiation, or ethylene oxide treatment.

18. The method of claim 1, wherein the composition is preserved.

19. The method of claim 18, wherein the composition is preserved in a preservation medium comprising one or more of polyvinyl pyrrolidone, a polysaccharide, a monosaccharide, an alginate, trehalose, raffinose, dextran, human serum albumin, ficoll, lipoproteins, or hydroxyethyl starch.

20. The method of claim 19, wherein the preservation medium comprises trehalose.

21. The method of claim 18, wherein the composition is preserved by cryopreservation or vitrification.

22. The method of claim 21, wherein the composition is preserved in a cryopreservation or vitrification medium comprising one or more of dimethyl sulfoxide (DMSO), glycerol, a glycol, propylene glycol, ethylene glycol, propanediol, polyethylene glycol (PEG), or 1,2-propanediol.

23. The method of claim 22, wherein the composition is preserved in a cryopreservation or vitrification medium comprising DMSO.

24. The method of claim 1, wherein the repair is associated with hip replacement operations, knee replacement operations, foot and ankle surgeries, spinal fusion procedures, repair of periodontal defects, treatment of osteoporotic fractures, repair of bone tumor defects, repair of cranial maxilla facial defects, general arthroplasty, cup arthroplasty of the hip, femoral and humeral head replacement, temporomandibular joint replacement, total joint replacement, repairs of the vertebral column, alveolar ridge augmentation and reconstruction, inlay bone grafts, implant placement and revision or sinus lifts, or repair of bone fractures or defects.

25. The method of claim 1, wherein the bone defect is a simple fracture, compound fracture, external fixation, internal fixation, joint reconstruction, arthroplasty, degenerative disc disease, avascular osteonecrosis, non-union fracture, osteosarcoma fracture, avascular osteonecrosis, bone fusion, spinal fusion, disc augmentation, or bone regeneration in orthopedic implants.

* * * * *